US010196438B2

(12) United States Patent
Wadia et al.

(10) Patent No.: US 10,196,438 B2
(45) Date of Patent: Feb. 5, 2019

(54) HUMAN ANTIBODIES BINDING TO RSV G PROTEIN

(71) Applicant: Crucell Holland B.V., Leiden (NL)

(72) Inventors: Jehangir Wadia, San Diego, CA (US); Robert Anthony Williamson, London (GB); Johannes P. M. Langedijk, Amsterdam (NL); Gabriel Pascual, San Diego, CA (US); Angelique Van 'T Wout, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 211 days.

(21) Appl. No.: 14/784,937

(22) PCT Filed: Apr. 14, 2014

(86) PCT No.: PCT/EP2014/057499
§ 371 (c)(1),
(2) Date: Oct. 15, 2015

(87) PCT Pub. No.: WO2014/170257
PCT Pub. Date: Oct. 23, 2014

(65) Prior Publication Data

US 2016/0145321 A1 May 26, 2016

Related U.S. Application Data

(60) Provisional application No. 61/812,098, filed on Apr. 15, 2013.

(30) Foreign Application Priority Data

Aug. 5, 2013 (EP) .................................... 13179241

(51) Int. Cl.

| | |
|---|---|
| ***C07K 14/115*** | (2006.01) |
| ***A61K 39/155*** | (2006.01) |
| ***A61K 39/145*** | (2006.01) |
| ***C07K 14/005*** | (2006.01) |
| ***C07K 16/10*** | (2006.01) |
| ***G01N 33/569*** | (2006.01) |
| ***A61K 47/68*** | (2017.01) |
| *A61K 39/00* | (2006.01) |

(52) U.S. Cl.

CPC ........ *C07K 16/1027* (2013.01); *A61K 39/155* (2013.01); *A61K 47/6841* (2017.08); *C07K 14/115* (2013.01); *G01N 33/56983* (2013.01); *A61K 39/145* (2013.01); *A61K 2039/505* (2013.01); *C07K 14/005* (2013.01); *C07K 2317/21* (2013.01); *C07K 2317/24* (2013.01); *C07K 2317/33* (2013.01); *C07K 2317/34* (2013.01); *C07K 2317/50* (2013.01); *C07K 2317/55* (2013.01); *C07K 2317/56* (2013.01); *C07K 2317/565* (2013.01); *C07K 2317/76* (2013.01); *G01N 2333/135* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 2009/0130120 | A1 | 5/2009 | Kauvar |
| 2011/0177117 | A1 | 7/2011 | Blais et al. |
| 2011/0318376 | A1 | 12/2011 | Murata |
| 2013/0034564 | A1 | 2/2013 | Kauvar |
| 2013/0285022 | A1 | 10/2013 | Su |

FOREIGN PATENT DOCUMENTS

| | | | |
|---|---|---|---|
| JP | 2011-528222 | | 11/2011 |
| WO | 0063403 | | 10/2000 |
| WO | 2009055711 | | 4/2009 |
| WO | 2014170257 | A1 | 10/2014 |
| WO | 2014170258 | A1 | 10/2014 |

OTHER PUBLICATIONS

Vajdos et al., Comprehensive Functional Maps of the Antigenbinding Site of an Anti-ErbB2 Antibody Obtained with Shotgun Scanning Mutagenesis, 2002, Journal of Molecular Biology, vol. 320, pp. 415-428.*

Youngjoo Choi et al., Antibodies to the Central Conserved Region of Respiratory Syncytial Virus (RSV) G Protein Block RSV G Protein CX3C-CX3CR1 Binding and Cross-Neutralize RSV A and B Strains, Viral Immunology, May 2, 2012, pp. 193-203, vol. 25, No. 3, Mary Ann Leibert, Inc.

Larry J Anderson et al., Neutralization of Respiratory Syncytial Virus by Individual and Mixtures of F and G Protein Monoclonal Antibodies, Journal of Virology, Nov. 1, 1988, pp. 4232-4238, vol.62, No. 11, The American Society for Microbiology.

Wayne Sullender, Antigenic Analysis of Chimeric and Truncated G Proteins of Respiratory Syncytial Virus, May 1, 1995, pp. 70-79, vol. 209, No. 1.

Ultan F. Power et al., Identification and Characterisation of Multiple linear B Cell Protectopes in the Respiratory syncytial Virus G Protein, Vaccine, Mar. 21, 2001, pp. 2345-2351, vol. 19, No. 17-19, Elseveir LTD, GB.

E.E. Walsh et al., Comparison of Antigenic Sites of Subtype-specific Respiratory Syncytial Virus Attachment Proteins, Journal of General Virology, Nov. 1, 1989, pp. 2953-2961, vol. 70, No. 11.

(Continued)

*Primary Examiner* — Benjamin P Blumel
(74) *Attorney, Agent, or Firm* — Kramer Amado P.C.

(57) ABSTRACT

The disclosure relates to isolated antibodies and antigen-binding fragments that bind to the G protein of RSV and which are capable of neutralizing RSV A and B subtypes, and the use thereof in the diagnosis, prophylaxis, and/or treatment of RSV infections.

8 Claims, 12 Drawing Sheets

Specification includes a Sequence Listing.

(56) References Cited

OTHER PUBLICATIONS

PCT International Search Report, PCT/EP2014/057499, dated Jul. 28, 2014.

PCT International Written Opinion, PCT/EP2014/057499, dated Jul. 28, 2014.

UniProt: the universal protein knowledgebase for Protein: Major surface glycoprotein G; Gene: G; Organism: Human respiratory syncytial virus A (strain Long) at least as early as Oct. 20, 2017.

Langedijk, et al., "A Subtype-Specific Peptide-Based Enzyme Immunoassay for Detection of Antibodies to the G Protein of Human Respiratory Syncytial Virus Is More Sensitive than Routine Serological Tests", Journal of Clinical Microbiology, Jul. 1997, p. 1656-1660 vol. 35, No. 7.

* cited by examiner

FIG. 7

Type A variants | CB003.1 (0.10 μg/mL) | CB010.7 (0.05 μg/mL) | CR9514 (1.0 μg/mL)

FEVFNFVPCSICSNNPTCWAICKRIPNKKPGK
FEVFNFVPCSICNNNPTCWAICKRIPNKKPGK
FEVFNFVPCSICSNNPTCRAICKRIPNKKPGK
FEVFNFVPCSICSNNPTCRAICKRIPSKKPGK
FEVFNFVPCSICSNNPTCWDICKRIPSKKPGK
FEVFNFVPCSICSNNPTCWTICKRIPNKKPGK
FEVFNFVPCSICSNNPTCWAICKKIPNKKPGK
FEVFNFVPCSICSNNPTCWAICKRMPNKKPGK
FEVFNFVPCSICSNNPTCWAICKRISNKKPGK
FEVFNFVPCSICSNNPTCWAICKRIPSKKLGK
FEVFNFVPCSICSNNPTCWAICKRIPSKKPGK
FEVFNFVPCSICSNNPTCWAICKRIPSKKPGR
FEVFNFVPCSICSNNPTCWAICKRIPSKKTGK
FEVFNFVPCSICSNNPTCWAICKRIPNKKLGK
FEVFNFVPCSICSNNPTCWAICKRIPNKKPAK
FEVFNFVPCSICSNNPTCWAICKRIPNKKPEK
FEVFNFVPCSICSNNPTCWAICKRIPNKKPRK
FEVFNFVPCSICSNNPTCWAICKRIPNKKPVK
FEVFNFVPCSICSNNPTCWAICKRIPNKKPGR

Type B variants

FEVFNFVPCSICGNNQLCKSICKTIPSNKPKK
FEVFNFVPCQICGNNQLCKSICKTIPSNKPKK
FEVFNFVPCGICGNNQLCKSICKTIPSNKPKK
FEVFNFVPCSTCGNNQLCKSICKTIPSNKPKK
FEVFNFVPCSYCGNNQLCKSICKTIPSNKPKK
FEVFNFVPCSICGNNKLCKSICKTIPSNKPKK
FEVFNFVPCSICGNNRLCKSICKTIPSNKPKK
FEVFNFVPCSICGNNQLCRSICKTIPSNKPKK
FEVFNFVPCSICGNNQLCKSFCKAIPSNKPKK
FEVFNFVPCSICGNNQLCKSICKKIPSNKPKK
FEVFNFVPCSICGNNQLCKSICKIIPSNKPKK
FEVFNFVPCSICGNNQLCKSICKTIPNNKPKK
FEVFNFVPCSICGNNQLCKSICKTIPSNKLKK 0 1000 2000 3000 | 0 1000 2000 3000 | 0 1000 2000 3000

FIG. 8
A
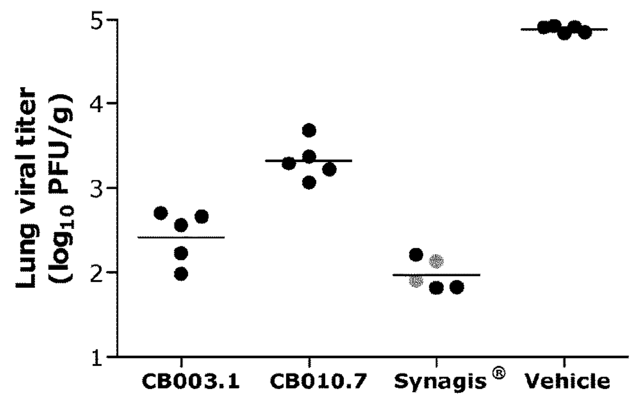
B
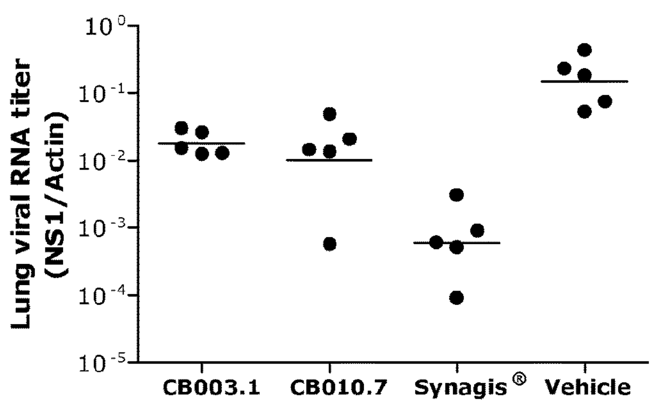
C
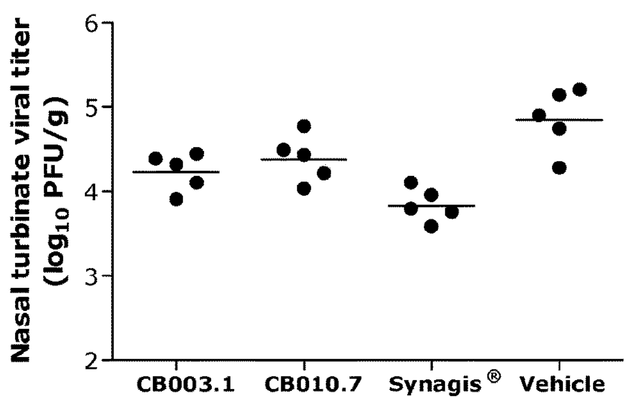

FIG. 9
A
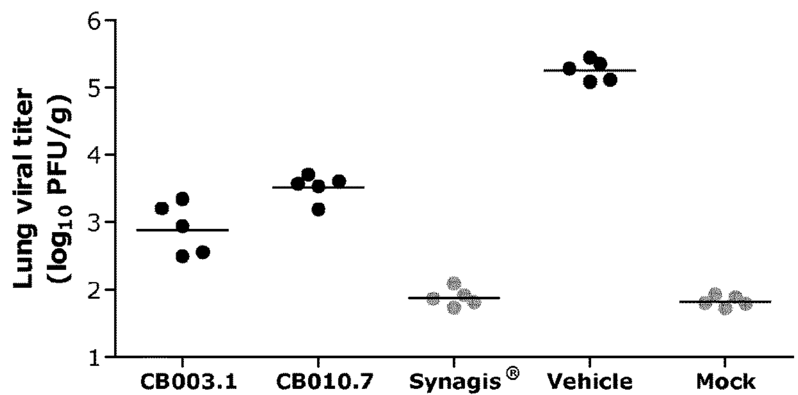
B
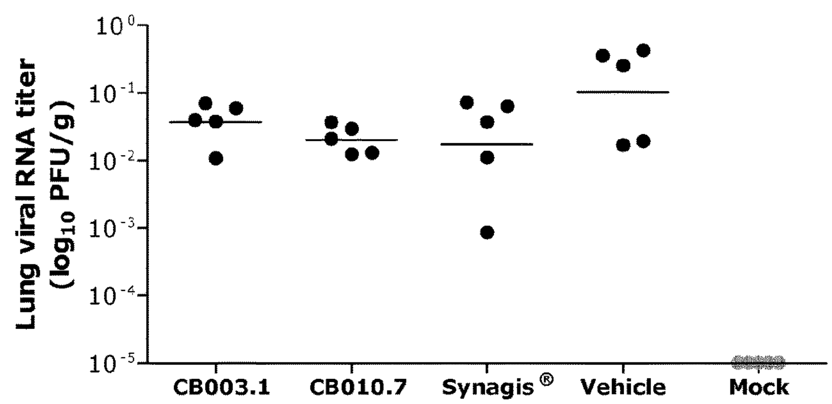
C
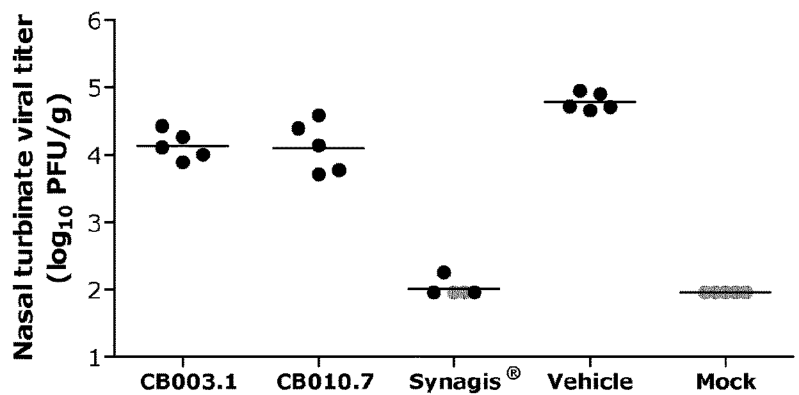

FIG. 10 (continued)
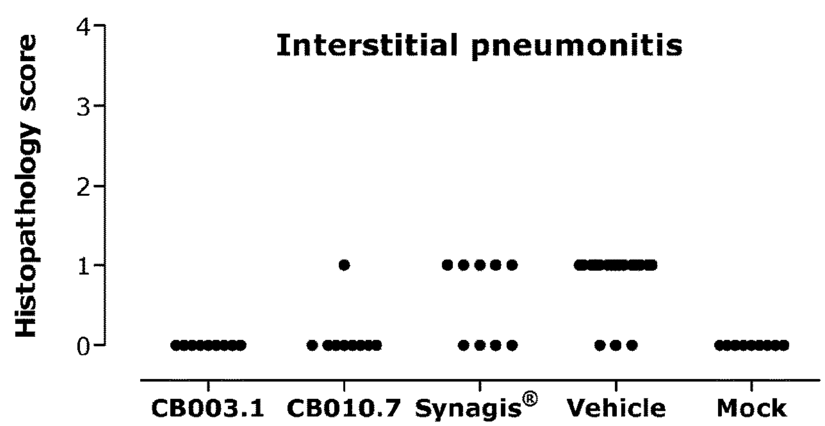
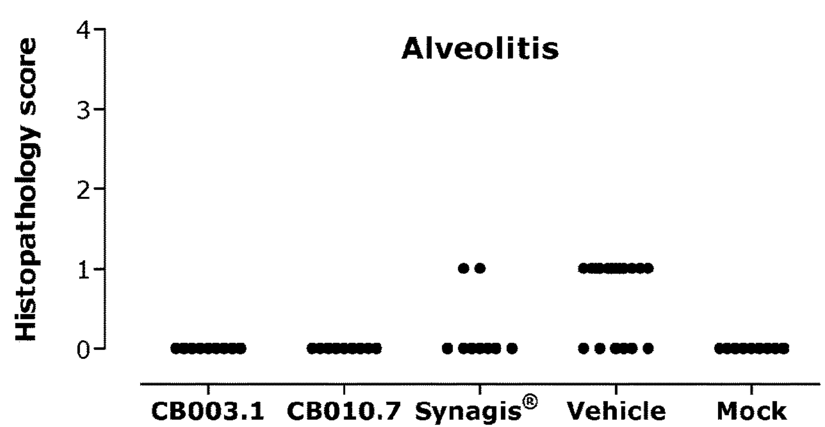

*Table 17. Epitope mapping of RSV G protein specific monoclonal antibodies (PepScan)*

| mAb | Type | Critical residues in central conserved domain | Epitope |
|---|---|---|---|
| | **RSV-A** | **$_{158}$DFHFEVFNFVPCSICSNNPTCWAICKRIPNKKPGK$_{192}$** | |
| | **RSV-B** | **$_{158}$DYHFEVFNFVPCSICGNNQLCKSICKTIPSNKPKK$_{192}$** | |
| 3D3 | RSV-A | -FHFEVFNFVPcs-c--n--c-aick-i----p-- | I |
| | RSV-B | -YHFEVFNFVPcs-c-----c--ic---------- | |
| CB002.1 | RSV-A | -FHFEVFNFVPc--c-nn--c-aick---n--p-- | I |
| | RSV-B | -YHFEVFNFVPcs-c--n--c--ick--------- | |
| CB003.1 | RSV-A | -FHFEVFNFVPCSI----------c---------g- | I |
| | RSV-B | -YHFEVFNFVPCSI----g-----c---------- | |
| CB010.7 | RSV-A | ---FEVFNFVPCSIc-----c-ai----------- | I |
| | RSV-B | ---FEVFNFVPCSIc-----c-------------- | |
| CB028.2 | RSV-A | ---FEVFNFVPc--c-----c---c---------- | I |
| | RSV-B | ---FEVFNFVP---c-----c-------------- | |
| CB048.3 | RSV-A | -FHFEVFNFVP------------------------ | I |
| | RSV-B | -YHFEVFNFVP-si-g-nqlc--ic-t-------- | |
| CB058.1 | RSV-A | --HFEVFNFVP------------------------ | I |
| | RSV-B | --HFEVFNFVPcsicgnnqlck-ic-tip------ | |

*Legend:* CAPS = *minimal epitope (shortest reactive peptide),* *ITALIC CAPS* = *additional residues that contribute to binding,* BOLD WHITE = *critical residues identified using full substitution analysis,* bold black = *(additional) critical residues identified using alanine scanning,* underline = *(additional) critical residues identified using available central region variant peptides.*

FIG. 11

HUMAN ANTIBODIES BINDING TO RSV G PROTEIN

CROSS-REFERENCE TO RELATED APPLICATIONS

This application is a national phase entry under 35 U.S.C. § 371 of International Patent Application PCT/EP2014/057499, filed Apr. 14, 2014, designating the United States of America and published in English as International Patent Publication WO 2014/170257 A1 on Oct. 23, 2014, which claims the benefit under Article 8 of the Patent Cooperation Treaty and under 35 U.S.C. § 119(e) to U.S. Provisional Patent Application Ser. No. 61/812,098, filed Apr. 15, 2013, and under Article 8 of the Patent Cooperation Treaty to European Patent Application Serial No. 13179241.8, filed Aug. 5, 2013.

STATEMENT ACCORDING TO 37 C.F.R. § 1.821(C) OR (E)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

TECHNICAL FIELD

The disclosure relates to biotechnology and medicine. The disclosure in particular relates to antibodies and antigen-binding fragments that specifically bind to the attachment glycoprotein (G protein) of Respiratory Syncytial Virus (RSV) and that neutralize RSV. The disclosure also relates to diagnostic, prophylactic and therapeutic methods using anti-RSV antibodies.

BACKGROUND

Human respiratory syncytial virus (RSV) is a negative-sense, single-stranded RNA virus of the family Paramyxoviridae, which also includes common respiratory viruses such as those causing measles and mumps. There are two primary RSV subtypes: subtype A and subtype B. RSV replicates in the upper respiratory track and then spreads to the lower airways leading to bronchiolitis or pneumonia. The virus causes inflammation, edema of the airways, increased mucus production, and breakdown of respiratory epithelium.

An estimated 64 million cases of respiratory illness and 160,000 deaths worldwide are attributable to RSV-induced disease. Severe RSV infection occurs most often in children and infants, especially in premature infants. Underlying health problems such as chronic lung disease or congenital heart disease can significantly increase the risk of serious illness. RSV infections also can cause serious illness in the elderly, individuals with chronic pulmonary disease and in immunocompromised adults, such as bone marrow transplant recipients.

Several approaches to the prevention and treatment of RSV infection have been investigated. Intravenous immunoglobulin (RSV-IGIV; RespiGam®) isolated from donors, and the monoclonal antibody palivizumab (SYNAGIS®) have been approved for RSV prophylaxis in high-risk premature infants. A vaccine or commercially available treatment for RSV, however, is not yet available. Only ribavirin, a RNA inhibitor, is approved for treatment of RSV infection. In order to be effective for treatment of RSV infection, high doses, repeated administrations and/or large volumes of antibody products, such as palivizumab, are required due to low effectivity.

RSV has two major surface glycoproteins, F and G. The F protein mediates fusion, allowing entry of the virus into the cell cytoplasm and facilitating the formation of syncytia in vitro. The F protein sequence is well (~90%) conserved among RSV strains (Johnson and Collins, J Gen Virol. (1988) 69: 2623-2628). The sole marketed monoclonal antibody palivizumab is directed against the F protein of RSV.

The G protein of RSV is a surface protein that is heavily glycosylated and functions as the attachment protein. In contrast to the F protein, the G protein is quite variable across strains except for a central conserved domain (CCD), comprising amino acid residues 153-184 of the G protein of the RSV A2 strain, or corresponding amino acid residues in other strains. Both the central conserved domain and adjacent regions (residues 145-193) are bounded by rigid and heavy O-glycosylated mucin-like regions. The N-terminal half of the central conserved domain contains a small region that is conserved among more than 700 strains. The C-terminal half contains 4 conserved cysteines that are connected in a 1-4, 2-3 topology and folds into a cystine noose.

Although passive immunization using antibodies directed to the G protein has generally been considered impractical due to the lack of sequence conservation across strains, neutralizing monoclonal antibodies binding to the RSV G protein are known. Anderson, L. J. et al (J. Virol. (1988) 62:4232-4238) describe the neutralization ability of mixtures of F and G murine monoclonal antibodies, one of which binds to the RSV G protein (i.e., 131-2G). The antigenic site of this antibody was later defined by Sullender (Virol. (1995) 209:70-79). This antibody was found to bind both RSV groups A and B, representing the major strains of RSV. In addition, WO 2009/055711 discloses antibodies, such as 3D3 and 3G12, which are immunoreactive with a conserved motif within the G protein of RSV A2 and have neutralizing activity against RSV A and B subtypes. These antibodies have been shown to recognize linear epitopes in the central conserved domain, but have not been tested in the preferred animal model (i.e., cotton rats) for evaluating RSV antibodies and vaccines.

In view of the severity of the respiratory illness caused by RSV, in particular in young children and in the elderly, there is an ongoing need for effective means to prevent and treat RSV infection.

BRIEF SUMMARY

The disclosure provides isolated antibodies, and antigen-binding fragments thereof, that bind specifically to the RSV G protein and that are capable of neutralizing RSV. The antibodies and antigen-binding fragments are preferably capable of specifically binding to and neutralizing RSV of both subtype A and B. Preferably, the antibodies are human antibodies. The antibodies bind to epitopes in the central conserved unglycosylated region (also referred to as central conserved domain, CCD) of the RSV G protein.

The antibodies and antigen-binding fragments have high affinity for the G protein and have potent neutralizing ability. The antibodies and antigen-binding fragments of the disclosure are useful as diagnostic, prophylactic and/or therapeutic agents, both alone and in combination with other diagnostic, prophylactic and/or therapeutic agents.

The disclosure further provides compositions which comprise one or more antibodies of the disclosure and/or antigen binding fragments thereof. The disclosure also provides diagnostic, prophylactic and therapeutic methods that employ the anti-RSV antibodies. Prophylactic and therapeutic methods include administering to human subjects the anti-RSV antibodies and/or antigen-binding fragments thereof for the prevention or treatment of a RSV infection and RSV-mediated diseases or conditions, and/or amelioration of one or more symptoms of a RSV infection. Combinations of a plurality of different anti-RSV antibodies and/or antigen-binding fragments thereof and/or with other anti-RSV antibodies can be used for combination therapy. Compositions comprising the anti-RSV antibodies and/or antigen-binding fragments thereof in combination with other prophylactic or therapeutic agents are also provided.

The disclosure also provides nucleic acid molecules encoding the antibodies or antigen-binding fragments thereof.

The antibodies of the disclosure are unique in that the antibodies are more potent against RSV type A and B than any known anti-RSV G antibody, in particular than the known anti-RSV G monoclonal antibody 3D3, at least in an in vitro neutralization assay.

The antibodies of the disclosure bind to unique epitopes on the RSV G protein.

In certain embodiments, the antibodies comprise a heavy chain CDR3 comprising a CXXXXC motif in its amino acid sequence (SEQ ID NO:133).

In certain embodiments, the antibodies and antigen-binding fragments thereof are unique in that they work additively and/or synergistically with anti-RSV F antibodies.

BRIEF DESCRIPTION OF THE DRAWINGS

FIG. 7 shows binding of the monoclonal antibodies to naturally occurring variants of the RSV G protein central region (e.g., SEQ ID NO:136 and SEQ ID NO:137). Binding of mAbs CB003.1 and CB010.7 with different peptides corresponding to available type A (top panel, SEQ ID NO:136) and type B (bottom panel, SEQ ID NO:137) variants. The reactivity of the wild-type peptide is shown as a grey bar.

FIG. 8 shows the prophylactic efficacy of anti-RSV G mAbs in cotton rat RSV-A/Long model on lung and nasal turbinate virus load at day 4 post challenge.

FIG. 9 shows the therapeutic efficacy of anti-RSV G mAbs in cotton rat RSV-A/Long model on lung and nasal turbinate virus load at day 4 post challenge.

FIG. 11 provides Table 17 which shows epitope mapping of RSV G protein specific monoclonal antibodies.

DETAILED DESCRIPTION

Definitions

Figure 1:
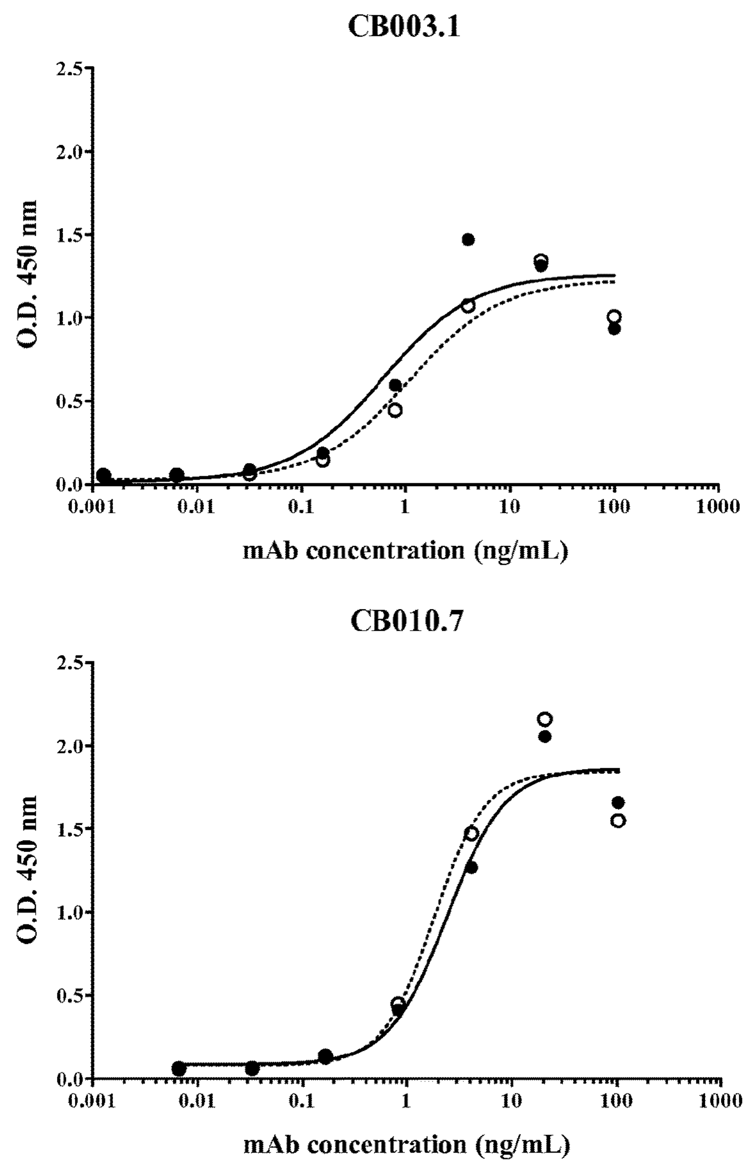
FIG. 1 shows the binding profiles against RSV Ga and RSV Gb protein. IgGs were tested in ELISA assays for their ability to bind to the ectodomain of recombinant RSV Ga and Gb protein. Open circles (dashed lined) denote binding to Ga (RSV A/Long) and closed circles (solid line) denote binding to Gb (RSV B/B1).
Figure 2:
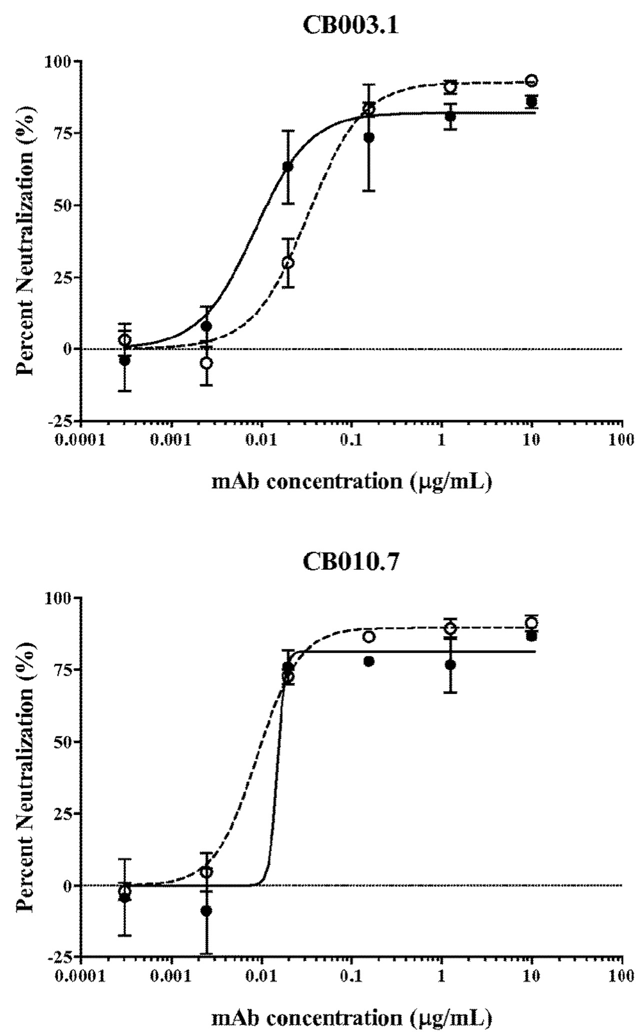
FIG. 2 shows the neutralization profiles against RSV-A and RSV-B strains. IgGs were tested in neutralization assays for their ability to neutralize RSV-A and RSV-B strains. Open circles (dashed line) denote neutralization of RSV-A (RSV A/A2) and closed circles (solid line) denote neutralization of RSV-B (RSV B/18537).

Definitions of terms as used in the disclosure are given below.

The term “included” or “including,” as used herein, is deemed to be followed by the words “without limitation.”

As used herein, the term “antibody” refers to immunoglobulin molecules including monoclonal antibodies, such as chimeric, humanized or human monoclonal antibodies. The term “antibody” includes all immunoglobulin classes and subclasses known in the art. Depending on the amino acid sequence of the constant domain of their heavy chains, antibodies can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

The term antigen-binding fragment refers to antigen-binding and/or variable domain comprising fragments of an immunoglobulin that compete with the intact immunoglobulin for specific binding to the binding partner of the immunoglobulin, i.e., RSV G protein. Regardless of structure, the antigen-binding fragment binds with the same antigen that is recognized by the intact immunoglobulin. Antigen-binding fragments include, inter alia, Fab, F(ab'), F(ab')2, Fv, dAb, Fd, complementarity determining region (CDR) fragments, single-chain antibodies (scFv), bivalent single-chain antibodies, (single) domain antibodies, diabodies, triabodies, tetrabodies, (poly) peptides that contain at least a fragment of an immunoglobulin that is sufficient to confer specific antigen binding to the (poly) peptide, etc. An antigen-binding fragment may comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the antibody. The antigen-binding fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, Edited by: E. Harlow and D, Lane (1988), Cold Spring Harbor Laboratory, Cold Spring Harbor, N.Y., which is incorporated herein by reference. An antibody or antigen-binding fragment thereof may have one or more binding sites. If there is more than one binding site, the binding sites may be identical to one another or they may be different.

The term "monoclonal antibody," as used herein, refers to antibody molecules of single specificity. A monoclonal antibody displays a single binding specificity and affinity for a particular epitope. Accordingly, the term "human monoclonal antibody" refers to an antibody displaying a single binding specificity which has variable and constant regions derived from or based on human germline immunoglobulin sequences or derived from completely synthetic sequences. The method of preparing the monoclonal antibody is not relevant for the binding specificity.

The term "functional variant," as used herein, refers to an antibody that comprises a nucleotide and/or amino acid sequence that is altered by one or more nucleotides and/or amino acids compared to the nucleotide and/or amino acid sequences of a reference antibody and that is capable of competing for specific binding to the binding partner, i.e., the RSV, with the reference antibody. In other words, the modifications in the amino acid and/or nucleotide sequence of the reference antibody do not significantly affect or alter the binding characteristics of the antibody encoded by the nucleotide sequence or containing the amino acid sequence, i.e., the antibody is still able to specifically recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

The term "neutralizing," as used herein, in relation to the antibodies of the disclosure refers to antibodies that are capable of preventing or inhibiting infection of a cell by the virus, by neutralizing or inhibiting its biological effect and/or reducing the infectious titer of RSV, regardless of the mechanism by which neutralization is achieved. Neutralization can, e.g., be achieved by inhibiting the attachment or adhesion of the virus to the cell surface, or by inhibition of the fusion of viral and cellular membranes following attachment of the virus to the target cell, and the like.

The term "specifically binding," as used herein, in reference to the interaction of an antibody and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means that the antibody is specifically immunoreactive with an antigenic determinant or epitope and is not immunoreactive with other antigenic determinants or epitopes. An antibody that (immuno)specifically binds to an antigen may bind to other peptides or polypeptides with lower affinity as determined by, e.g., radioimmunoassays (RIA), enzyme-linked immunosorbent assays (ELISA), BIACORE, or other assays known in the art. Antibodies or fragments thereof that specifically bind to an antigen may be cross-reactive with related antigens, carrying the same epitope. Preferably, antibodies or fragments thereof that specifically bind to an antigen do not cross-react with other antigens.

In a first aspect the disclosure provides antibodies and antigen-binding fragments capable of specifically binding to the G protein of respiratory syncytial virus (RSV) and that are capable of neutralizing RSV. The antibodies are preferably capable of specifically binding to and neutralizing RSV of both subtype A and B. Preferably, the antibodies are human monoclonal antibodies.

According to the disclosure, the antibodies and antigen-binding fragments bind to epitopes in the central conserved domain (CCD) of the RSV G protein. The central conserved domain spans the amino acid sequence comprising the amino acids 153-184 of the G protein of the RSV A2 strain, Accession No. P20895 (or corresponding amino acid residues in other strains). In certain embodiments, the antibodies and antigen-binding fragments bind to an epitope comprising one or more amino acid residues within the amino acid sequence comprising amino acid residues 161-169, in particular one or more amino acids within the amino acid sequence comprising the amino acid residues 162-168 of the G protein of the RSV A2 strain (numbering according to RSV A2 strain).

Antibodies and antigen-binding fragments thus are provided that bind to an epitope in the G protein that is located at a site that is N-terminal of the cystine noose. According to the disclosure, it has been shown that despite the fact that at least some of the neutralizing antibodies of the disclosure bind to a similar, but not identical linear epitope as, e.g., the previously described monoclonal antibody 3D3 (WO2009/055711), the antibodies of the disclosure have a higher neutralizing potency, as measured in an in vitro neutralization assay. According to the disclosure, it has been shown that the antibodies of the disclosure bind this linear epitope in a unique manner. Thus, according to the disclosure it has been shown that these antibodies have different side chain specificity for the 161-169 epitope of RSV type A and B (numbering according to RSV strain A2). This is, e.g., reflected by the substitution analysis (see Example 11) which shows that the epitope of the antibodies of the disclosure has different essential residues, as compared to, e.g., 3D3.

The antibodies and antigen-binding fragments of the disclosure have been shown to be more potent against RSV type A and B than any of the known anti-RSV G antibodies, in particular more potent than the known anti-RSV G monoclonal antibody 3D3, in an in vitro neutralization assay, in particular an in vitro assay as described in Example 7.

In certain embodiments, the IC50 (effective dilution for 50% neutralization of plaque formation) of the antibodies and antigen-binding fragments for RSV strain A/A2 (ATCC Cat. No. VR-1540) was below 40 ng/ml and/or the IC50 for RSV strains B/18537 (ATCC Cat. No. VR-1589) was below 30 ng/ml.

In an embodiment, the antibody is not an antibody selected from the group consisting of 1F12, 3G12, 1A5, 3D3, 1G1, 2B11, 5D8, 2D10, 3F9, 1D4, 1G8, 6A12, 10C6 (as described in WO 2009/055711).

In certain embodiments, the antibody or antibody fragment of the disclosure competes for binding to the RSV G protein with an antibody selected from the group consisting of 1F12, 3G12, 1A5, 3D3, 1G1, 2B11, 5D8, 2D10, 3F9, 1D4, 1G8, 6A12, and 10C6 (as described in WO 2009/055711).

In certain embodiments, the antibodies comprise a heavy chain CDR3 comprising a CXXXXC motif in its amino acid sequence (SEQ ID NO:133).

In certain embodiments, the antibody comprises a heavy chain comprising:

a) a heavy chain CDR1 region of SEQ ID NO:1, a heavy chain CDR2 region of SEQ ID NO:2, and a heavy chain CDR3 region of SEQ ID NO:3, b) a heavy chain CDR1 region of SEQ ID NO:4, a heavy chain CDR2 region of SEQ ID NO:5, and a heavy chain CDR3 region of SEQ ID NO:6, c) a heavy chain CDR1 region of SEQ ID NO:7, a heavy chain CDR2 region of SEQ ID NO:8, and a heavy chain CDR3 region of SEQ ID NO:9, d) a heavy chain CDR1 region of SEQ ID NO:10, a heavy chain CDR2 region of SEQ ID NO:11, and a heavy chain CDR3 region of SEQ ID NO:12, e) a heavy chain CDR1 region of SEQ ID NO:25, a heavy chain CDR2 region of SEQ ID NO:26, and a heavy chain CDR3 region of SEQ ID NO:27, or f) a heavy chain CDR1 region of SEQ ID NO:31, a heavy chain CDR2 region of SEQ ID NO:32, and a heavy chain CDR3 region of SEQ ID NO:33.

In certain embodiments, the antibody comprises a light chain comprising:

a) a light chain CDR1 region of SEQ ID NO:13, a light chain CDR2 region of SEQ ID NO:14, and a light chain CDR3 region of SEQ ID NO:15, b) a light chain CDR1 region of SEQ ID NO:16, a light chain CDR2 region of SEQ ID NO:17, and a light chain CDR3 region of SEQ ID NO:18, c) a light chain CDR1 region of SEQ ID NO:19, a heavy chain CDR2 region of SEQ ID NO:20, and a light chain CDR3 region of SEQ ID NO:21, d) a light chain CDR1 region of SEQ ID NO:22, a light chain CDR2 region of SEQ ID NO:23, and a light chain CDR3 region of SEQ ID NO:24, e) a light chain CDR1 region of SEQ ID NO:28, a light chain CDR2 region of SEQ ID NO:29, and a light chain CDR3 region of SEQ ID NO:30, or f) a light chain CDR1 region of SEQ ID NO:34, a light chain CDR2 region of SEQ ID NO:35, and a light chain CDR3 region of SEQ ID NO:36.

In certain embodiments, the antibody is selected from the group consisting of:

a) an antibody comprising a heavy chain CDR1 region of SEQ ID NO:1, a heavy chain CDR2 region of SEQ ID NO:2, and a heavy chain CDR3 region of SEQ ID NO:3, a light chain CDR1 region of SEQ ID NO:13, a light chain CDR2 region of SEQ ID NO:14, and a light chain CDR3 region of SEQ ID NO:15;

b) a heavy chain CDR1 region of SEQ ID NO:4, a heavy chain CDR2 region of SEQ ID NO:5, and a heavy chain CDR3 region of SEQ ID NO:6 and a light chain CDR1 region of SEQ ID NO:16, a light chain CDR2 region of SEQ ID NO:17, and a light chain CDR3 region of SEQ ID NO:18;

c) an antibody comprising a heavy chain CDR1 region of SEQ ID NO:7, a heavy chain CDR2 region of SEQ ID NO:8, and a heavy chain CDR3 region of SEQ ID NO:9, a light chain CDR1 region of SEQ ID NO:19, a heavy chain CDR2 region of SEQ ID NO:20, and a light chain CDR3 region of SEQ ID NO:21;

d) an antibody comprising a heavy chain CDR1 region of SEQ ID NO:10, a heavy chain CDR2 region of SEQ ID NO:11, and a heavy chain CDR3 region of SEQ ID NO:12, a light chain CDR1 region of SEQ ID NO:22, a light chain CDR2 region of SEQ ID NO:23, and a light chain CDR3 region of SEQ ID NO:24;

e) an antibody comprising a heavy chain CDR1 region of SEQ ID NO:25, a heavy chain CDR2 region of SEQ ID NO:26, and a heavy chain CDR3 region of SEQ ID NO:27, a light chain CDR1 region of SEQ ID NO:28, a light chain CDR2 region of SEQ ID NO:29, and a light chain CDR3 region of SEQ ID NO:30; and f) an antibody comprising a heavy chain CDR1 region of SEQ ID NO:31, a heavy chain CDR2 region of SEQ ID NO:32, and a heavy chain CDR3 region of SEQ ID NO:33, a light chain CDR1 region of SEQ ID NO:34, a light chain CDR2 region of SEQ ID NO:35, and a light chain CDR3 region of SEQ ID NO:36.

In certain embodiments, the antibody comprises a heavy chain variable region comprising the amino acid sequence of SEQ ID NO:37, a heavy chain variable region comprising the amino acid sequence of SEQ ID NO:39, a heavy chain variable region comprising the amino acid sequence of SEQ ID NO:41, a heavy chain variable region comprising the amino acid sequence of SEQ ID NO:43, a heavy chain variable region comprising the amino acid sequence of SEQ ID NO:45 or a heavy chain variable region comprising the amino acid sequence of SEQ ID NO:47.

In certain embodiments, the antibody comprises a light chain variable region comprising the amino acid sequence of SEQ ID NO:38, a light chain variable region comprising the amino acid sequence of SEQ ID NO:40, a light chain variable region comprising the amino acid sequence of SEQ ID NO:42, a light chain variable region comprising the amino acid sequence of SEQ ID NO:44, a light chain variable region comprising the amino acid sequence of SEQ ID NO:46 or a light chain variable region comprising the amino acid sequence of SEQ ID NO:48.

In certain embodiments, the antibody is selected from the group consisting of:

a) an antibody comprising a heavy chain variable region comprising the amino acid sequence of SEQ ID NO:37 and a light chain variable region comprising the amino acid sequence of SEQ ID NO:38;

b) an antibody comprising a heavy chain variable region comprising the amino acid sequence of SEQ ID NO:39 and a light chain variable region comprising the amino acid sequence of SEQ ID NO:40;

c) an antibody comprising a heavy chain variable region comprising the amino acid sequence of SEQ ID NO:41 and a light chain variable region comprising the amino acid sequence of SEQ ID NO:42;

d) an antibody comprising a heavy chain variable region comprising the amino acid sequence of SEQ ID NO:43 and a light chain variable region comprising the amino acid sequence of SEQ ID NO:44;

e) an antibody comprising a heavy chain variable region comprising the amino acid sequence of SEQ ID NO:45 and a light chain variable region comprising the amino acid sequence of SEQ ID NO:46; and f) an antibody comprising a heavy chain variable region comprising the amino acid sequence of SEQ ID NO:47 and a light chain variable region comprising the amino acid sequence of SEQ ID NO:48.

In certain embodiments, antigen-binding fragments of the above described antibodies are provided. The antigen-binding fragments preferably bind to the same epitope.

The antibodies and antigen-binding fragments of the disclosure bind to different epitopes as compared to the epitopes of known anti-RSV G proteins, such as, e.g., the anti-RSV G antibody 3D3, which also has been shown to bind to an epitope in the central conserved domain of the RSV G protein. With binding to a different epitope it is meant that the antibody binds to different critical amino acid residues as compared to known antibodies, such as 3D3. It has furthermore been shown that the antibodies of the disclosure are more potent than any of the known RSV G protein binding antibodies, when measured in an in vitro neutralization assay, in particular an in vitro neutralization assay as described in Example 7.

In certain embodiments, the antibodies act synergistically when used in combination with antibodies binding to RVS F protein. As used herein, the term "synergistic" means that the combined effect of the antibodies or antigen-binding fragments when used in combination is greater than their additive effects when used individually. A way of calculating synergy is by means of the combination index. The concept of the combination index (CI) has been described by Chou and Talalay (Adv Enzyme Regul., 22:27-55, 1984).

In certain embodiments, the antibodies and antigen-binding fragments are for use as a medicament, and preferably for use in the diagnostic, therapeutic and/or prophylactic treatment of RSV infection caused by RSV A and/or B subtypes. As used herein, the term "treat" or "treatment" refers to reducing the viral burden in a subject that is already infected with RSV and/or to ameliorating the symptoms of the disease in such a subject. Such symptoms include, e.g., bronchiolitis, airway inflammation, congestion in the lungs, and difficulty of breathing. "Prevention" or "prophylaxis" encompasses inhibiting or reducing the spread of RSV or inhibiting or reducing the onset, development or progression of one or more of the symptoms associated with infection with RSV.

The disclosure also relates to compositions comprising at least one antibody or antigen-binding fragment of the disclosure. In certain embodiments, the compositions are pharmaceutical compositions comprising at least one antibody or antigen-binding fragment according to the disclosure, and at least a pharmaceutically acceptable excipient. By "pharmaceutically acceptable excipient" is meant any inert substance that is combined with an active molecule, such as an antibody, for preparing a convenient dosage form. The "pharmaceutically acceptable excipient" is an excipient that is non-toxic to recipients at the used dosages and concentrations, and is compatible with other ingredients of the formulation comprising the drug, agent or antibody. Pharmaceutically acceptable excipients are widely applied and known in the art.

In yet another embodiment the disclosure relates to the use of an antibody or antigen-binding fragment of the disclosure in the preparation of a medicament for the diagnosis, prophylaxis, and/or treatment of RSV infection. The disclosure also relates to methods of prevention or treatment of RSV infection by administering a therapeutically effective amount of an antibody according to the disclosure to a subject in need thereof. The term "therapeutically effective amount" refers to an amount of the antibody, as defined herein, that is effective for preventing, ameliorating and/or treating a condition resulting from infection with RSV. Amelioration, as used herein, may refer to the reduction of visible or perceptible disease symptoms, viremia, or any other measurable manifestation of RSV infection.

For use in therapy, the antibodies or fragments thereof are formulated into pharmaceutical compositions using suitable excipients and administered according to standard protocols. The pharmaceutical compositions may comprise one or more antibodies or antigen-binding fragments according to the disclosure. Additional therapeutic agents may be present, including one or more antibodies that are immunoreactive with the F protein of RSV or other therapeutic agents that are effective against RSV or inflammation. Thus, anti-inflammatory agents such as both steroidal and non-steroidal anti-inflammatory compounds may be included in the compositions.

In certain embodiments, complete antibodies, i.e., containing the complement-containing Fc region are used.

In certain embodiments, e.g., in order to reduce the inflammatory response in the lungs, only the antigen-binding fragments of the antibodies are used. Administration of mixtures of immunospecific fragments and entire antibodies is also included within the scope of the disclosure.

Treatment may be targeted at patient groups that are susceptible to RSV infection. Such patient groups include, but are not limited to, e.g., the elderly (e.g., ≥50 years old, ≥60 years old, and preferably ≥65 years old), the young (e.g., ≤5 years old, ≤1 year old), hospitalized patients, immunocompromised patients and patients who have been treated with an antiviral compound but have shown an inadequate antiviral response.

Administration of the antibody compositions of the disclosure is typically by injection, generally intramuscular or intravenous injection. The formulations are prepared in ways generally known in the art for administering antibody compositions. Suitable formulations may be found in standard formularies, such as Remington's Pharmaceutical Sciences, latest edition, Mack Publishing Co., Easton, Pa., incorporated herein by reference. The formulations are typically those suitable for parenteral administration including isotonic solutions, which include buffers, antioxidants and the like, as well as emulsions that include delivery vehicles such as liposomes, micelles and nanoparticles.

The desired protocols and formulations are dependent on the judgment of the attending practitioner as well as the specific condition of the subject. Dosage levels will depend on the age, general health and severity of infection, if appropriate, of the subject.

Another aspect of the disclosure includes functional variants of the antibodies as defined herein. Molecules are considered to be functional variants of an antibody, according to the disclosure, if the variants are capable of competing for specifically binding to RSV or a fragment thereof with the "parental" or "reference" antibodies. In other words, molecules are considered to be functional variants of an antibody, according to the disclosure when the functional variants are still capable of binding to the same or overlapping epitope of RSV or a fragment thereof. Functional variants include, but are not limited to, derivatives that are substantially similar in primary structural sequence, including those that have modifications in the Fc receptor or other regions involved with effector functions, and/or which contain, e.g., in vitro or in vivo modifications, chemical and/or biochemical, that are not found in the parental antibody. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, PEGylation, proteolytic processing, phosphorylation, and the like.

Alternatively, functional variants can be antibodies, as defined in the disclosure, comprising an amino acid sequence containing substitutions, insertions, deletions or combinations thereof of one or more amino acids compared to the amino acid sequences of the parental antibodies. Furthermore, functional variants can comprise truncations of the amino acid sequence at either or both the amino or carboxyl termini. Functional variants, according to the disclosure, may have the same or different, either higher or lower, binding affinities compared to the parental antibody but are still capable of binding to RSV or a fragment thereof. For instance, functional variants, according to the disclosure, may have increased or decreased binding affinities for RSV or a fragment thereof compared to the parental antibodies. Functional variants intended to fall within the scope of the disclosure have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and in particular at least about 97% to about 99% amino acid sequence identity and/or homology with the parental antibodies as defined herein. Computer algorithms such as inter alia Gap or Bestfit known to a person skilled in the art can be used to optimally align amino acid sequences to be compared and to define similar or identical amino acid residues. Functional variants can be obtained by altering the parental antibodies or parts thereof by general molecular biology methods known in the art including, but not limited to, error-prone PCR, oligonucleotide-directed mutagenesis, site-directed mutagenesis and heavy and/or light chain shuffling.

The disclosure also provides immunoconjugates, i.e., molecules comprising at least one antibody, antigen-binding fragment or functional variant and further comprising at least one tag, such as inter alia a detectable moiety/agent. Also contemplated in the disclosure are mixtures of immunoconjugates, according to the disclosure, or mixtures of at least one immunoconjugate, according to the disclosure, and another molecule, such as a therapeutic agent or another antibody or immunoconjugate. In a further embodiment, the immunoconjugates of the disclosure may comprise more than one tag. These tags can be the same or distinct from each other and can be joined/conjugated non-covalently to the antibodies. The tag(s) can also be joined/conjugated directly to the human antibodies through covalent bonding. Alternatively, the tag(s) can be joined/conjugated to the antibodies by means of one or more linking compounds. Techniques for conjugating tags to antibodies are well known to the skilled artisan. The tags of the immunoconjugates of the disclosure may be therapeutic agents, but they can also be detectable moieties/agents. Tags suitable in therapy and/or prevention may be toxins or functional parts thereof, antibiotics, enzymes, other antibodies that enhance phagocytosis or immune stimulation. Immunoconjugates comprising a detectable agent can be used diagnostically to, for example, assess if a subject has been infected with RSV or to monitor the development or progression of RSV infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the antibodies for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

Furthermore, the human antibodies or immunoconjugates of the disclosure can also be attached to solid supports, which are particularly useful for in vitro immunoassays or purification of RSV or fragments thereof. The antibodies of the disclosure can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect, the antibodies of the disclosure may be conjugated/attached to one or more antigens. Preferably, these antigens are antigens which are recognized by the immune system of a subject to which the antibody-antigen conjugate is administered. The antigens may be identical, but may also differ from each other. Conjugation methods for attaching the antigens and antibodies are well known in the art and include, but are not limited to, the use of cross-linking agents.

Next to producing immunoconjugates chemically by conjugating, directly or indirectly, via, for instance, a linker, the immunoconjugates can be produced as fusion proteins comprising the antibodies of the disclosure and a suitable tag. Fusion proteins can be produced by methods known in the art such as, e.g., recombinantly by constructing nucleic acid molecules comprising nucleotide sequences encoding the antibodies in frame with nucleotide sequences encoding the suitable tag(s) and then expressing the nucleic acid molecules.

The disclosure furthermore provides nucleic acid molecules encoding an antibody, antigen-binding fragment, or functional variant, according to the disclosure. Such nucleic acid molecules can be used as intermediates for cloning purposes, e.g., in the process of affinity maturation, as described above. In a preferred embodiment, the nucleic acid molecules are isolated or purified. The skilled artisan will appreciate that functional variants of these nucleic acid molecules are also intended to be a part of the disclosure. Functional variants are nucleic acid sequences that can be directly translated, using the standard genetic code, to provide an amino acid sequence identical to that translated from the parental nucleic acid molecules. Preferably, the nucleic acid molecules encode antibodies comprising the CDR regions, as described above. In a further embodiment, the nucleic acid molecules encode antibodies comprising two, three, four, five or even all six CDR regions of the antibodies of the disclosure.

It is another aspect of the disclosure to provide vectors, i.e., nucleic acid constructs, comprising one or more nucleic acid molecules, according to the disclosure. Vectors can be derived from plasmids such as inter alia F, R1, RP1, Col, pBR322, TOL, Ti, etc.; cosmids; phages such as lambda, lambdoid, M13, Mu, P1, P22, Qβ, T-even, T-odd, T2, T4, T7, etc.; plant viruses. Vectors can be used for cloning and/or for expression of the antibodies of the disclosure and might even be used for gene therapy purposes. Vectors comprising one or more nucleic acid molecules, according to the disclosure, operably linked to one or more expression-regulating nucleic acid molecules are also covered by the disclosure. The choice of the vector is dependent on the recombinant procedures followed and the host used. Introduction of vectors in host cells can be effected by inter alia calcium phosphate transfection, virus infection, DEAE-dextran mediated transfection, lipofectamine transfection or electroporation. Vectors may be autonomously replicating or may replicate together with the chromosome into which they have been integrated. Preferably, the vectors contain one or more selection markers. The choice of the markers may depend on the host cells of choice, although this is not critical to the disclosure as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the human antibodies, as described above, operably linked to one or more nucleic acid molecules encoding proteins or peptides that can be used to isolate the human antibodies are also covered by the disclosure. These proteins or peptides include, but are not limited to, glutathione-S-transferase, maltose binding protein, metal-binding polyhistidine, green fluorescent protein, luciferase and beta-galactosidase.

The disclosure also provides host cells containing one or more copies of the vectors mentioned above. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or ballistic gene transfer. Additionally, a suitable expression system can be a baculovirus system. Expression systems using mammalian cells, such as Chinese Hamster Ovary (CHO) cells, COS cells, BHK cells, NSO cells or Bowes melanoma cells are preferred in the disclosure. Mammalian cells provide expressed proteins with posttranslational modifications that are most similar to natural molecules of mammalian origin. Since the disclosure deals with molecules that may have to be administered to humans, a completely human expression system would be particularly preferred. Therefore, even more preferably, the host cells are human cells. Examples of human cells are inter alia HeLa, 911, AT1080, A549, 293 and HEK293 cells. In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on Feb. 29, 1996 under number 96022940 and marketed under the trademark PER.C6® (PER.C6 is a registered trademark of Crucell Holland B.V.). For the purposes of this application "PER.C6 cells" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403, the disclosure of which is incorporated herein by reference in its entirety.

The antibodies of the disclosure can be prepared by various means. A method of producing an antibody, according to the disclosure, is an additional part of the disclosure. The method comprises the steps of a) culturing a host cell, according to the disclosure, under conditions conducive to the expression of the antibody, and b) optionally, recovering the expressed antibody. The expressed antibodies can be recovered from the cell free extract, but preferably they are recovered from the culture medium. The above method of producing can also be used to make functional variants of the antibodies and/or immunoconjugates of the disclosure. Methods to recover proteins, such as antibodies, from cell free extracts or culture medium are well known to the artisan skilled in the art.

Alternatively, next to the expression in hosts, such as host cells, the antibodies and immunoconjugates of the disclosure can be produced synthetically by conventional peptide synthesizers or in cell-free translation systems using RNA nucleic acid derived from DNA molecules, according to the disclosure. The antibodies, according to the disclosure, may also be generated by transgenic non-human mammals, such as, for instance, transgenic mice or rabbits that express human immunoglobulin genes. Preferably, the transgenic non-human mammals have a genome comprising a human heavy chain transgene and a human light chain transgene encoding all or a portion of the human antibodies, as described above. The transgenic non-human mammals can be immunized with a purified or enriched preparation of RSV or a fragment thereof. Protocols for immunizing non-human mammals are well established in the art. See Using Antibodies: A Laboratory Manual, Edited by: E. Harlow, D. Lane (1998), Cold Spring Harbor Laboratory, Cold Spring Harbor, N.Y. and Current Protocols in Immunology, Edited by: J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In other embodiments, the human antibodies are produced by B-cells, plasma and/or memory cells derived from the transgenic animals. In yet another embodiment, the human antibodies are produced by hybridomas, which are prepared by fusion of B-cells obtained from the above-described transgenic non-human mammals to immortalized cells. B-cells, plasma cells and hybridomas as obtainable from the above-described transgenic non-human mammals and human antibodies as obtainable from the above-described transgenic non-human mammals, B-cells, plasma and/or memory cells and hybridomas are also a part of the disclosure.

The disclosure further provides kits comprising at least an antibody, an antigen-binding fragment, an immunoconjugate, a functional variant, and/or at least a nucleic acid, according to the disclosure. Optionally, the above-described components of the kits of the disclosure are packed in suitable containers and labeled for diagnosis, prophylaxis and/or treatment of the indicated conditions. The above-mentioned components may be stored in unit or multi-dose containers as an aqueous, preferably sterile, solution or as a lyophilised, preferably sterile, formulation for reconstitution. The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products, that contain information about, for example, the indications, usage, dosage, manufacture, administration, contra-indications and/or warnings concerning the use of such therapeutic, prophylactic or diagnostic products.

The antibodies, according to the disclosure, can also be advantageously used as a diagnostic agent in an in vitro method for the detection of RSV. The disclosure, thus, further provides a method of detecting RSV in a sample, wherein the method comprises the steps of (a) assaying the level of RSV antigen in a sample, e.g., by contacting a sample with a diagnostically effective amount of an antibody (or fragments thereof) or an immunoconjugate, according to the disclosure, and (b) comparing the assayed level of RSV antigen with a control level, whereby an increase in the assayed level of RSV antigen compared to the control level is indicative of RSV infection. The sample may be a biological sample including, but not limited to blood, serum, stool, sputum, nasophargyal aspirates, bronchial lavages, urine, tissue or other biological material from (potentially) infected subjects, or a non-biological sample such as water, drink, etc. The sample may first be manipulated to make it more suitable for the method of detection. Manipulation means inter alia treating the sample suspected to contain and/or containing the virus in such a way that the virus will disintegrate into antigenic components such as proteins, (poly) peptides or other antigenic fragments. Preferably, the antibodies or immunoconjugates of the disclosure are contacted with the sample under conditions which allow the formation of an immunological complex between the antibody and the virus or antigenic components thereof that may be present in the sample. The formation of an immunological complex, if any, indicating the presence of the virus in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses. Preferred assay techniques, especially for large-scale clinical screening of patient sera and blood and blood-derived products are ELISA and Western blot techniques. ELISA tests are particularly preferred.

The disclosure is further illustrated in the following examples which are not intended to limit the disclosure.

EXAMPLES

Example 1

Antigen Production and Labelling

Unlike the fusion protein (RSV F) expressed on the surface of the viral membrane, the attachment protein (RSV G) is highly variable, thus defining the two broad subtypes of RSV (i.e., subtypes A and B). Despite the sequence variability, RSV G contains a central and highly conserved region. In an effort to obtain broadly neutralizing monoclonal antibodies, RSV G corresponding to a representative subgroup A (RSV A/Long) and subgroup B strain (RSV B/B1) were expressed recombinantly in 293 freestyle cells, purified, and labeled for use in single cell sorting experiments.

Expression of RSV Ga and Gb

Recombinant RSV attachment protein (G protein) corresponding to RSV A/Long (Accession No. P20895, SEQ ID NO:49) and RSV B/B1 (Accession No. NP 056862, SEQ ID NO:50), herein referred to RSV Ga and Gb, were expressed from a CMV-based promoter mammalian expression vector (Invitrogen Corp., pcDNA3.1) with both a Myc (EQKLISEEDL (residues 239-248 of SEQ ID NO:49)) and 6× histidine tag (Table 1). Leader sequence corresponding to human V kappa I signal peptide was introduced at amino terminus to promote secretion. Both RSV Ga and Gb were expressed lacking the transmembrane domain and included amino acids 65-288 and 65-299 of RSV Ga (SEQ ID NO:49) and Gb (SEQ ID NO:50), respectively.

RSV Ga and Gb were transfected, according to manufacturer guidelines. Recombinantly expressed RSV Ga and Gb proteins were purified using Nickel NTA chromatography. Seventy-two hours after transfection the supernatant was harvested and dialyzed overnight against 20 mM Tris-HCL pH8 and 300 mM NaCl. The following day, the dialysis was repeated with fresh buffer and for an additional 6 hours. The dialyzed supernatant was then supplemented with 5% glycerol and 10 mM imidazole (VWR, Cat. No. EM-5720) and loaded onto a column packed with 2 mL of Ni-NTA agarose beads (Qiagen, Cat. No. 30310). The bound protein was subsequently washed with 2 column volumes of wash buffer consisting of 20 mM Tris-HCl, pH8, 300 mM NaCl, 5% glycerol, and 20 mM imidazole. The proteins were then eluted with 5 mL of elution buffer containing 20 mM Tris-HCl, pH8, 300 mM NaCl, 5% glycerol, and 50 mM imidazole. Finally, the eluate was dialyzed against four liters of phosphate buffered saline (PBS) at 4° C. overnight. The dialyzed protein was then concentrated to 0.5-1.0 mL in a 30K MWCO concentrator (Millipore, Amicon Ultracel concentrator) and quantitated by bicinchoninic acid assay (BCA assay; Thermo Fisher, per manufacturer instructions). In addition, the purified proteins were each quality-controlled by SDS-PAGE/Coomassie.

RSV Ga was fluorescently labeled with Alexa Fluor 647 (AF 647) using the Alexa Fluor 647 microscale protein labelling kit (Invitrogen Cat. No. A30009) according to manufacturer's instructions. After purification, the degree of labelling was determined to be 1.2 moles of AF 647 per mole of protein using a NANODROP® UV spectrophotometer (manufacturer). Similarly, the RSV Gb protein was labeled with Alexa Fluor 488 (AF 488) using a microscale protein labelling kit (Invitrogen Cat. No. A30006) according to manufacturer's instructions and after final purification, the degree of labelling was determined using a NANODROP® spectrophotometer to be about 2 moles of AF 488 per mole of protein.

TABLE 1

| Recombinant RSV G protein sequences used | |
|---|---|
| Protein (Accession No.) | Amino Acid Sequence |
| RSV G A/Long (P20895) | ANHKVTLTTAIIQDATSQIKNTTPTYLTQDPQL GISFSNLSEITSQTTTILASTTPGVKSNLQPTT VKTKNTTTTQTQPSKPTTKQRQNKPPNKPNNDF HFEVFNFVPCSICSNNPTCWAICKRIPNKKPGK KTTTKPTKKPTFKTTKKDLKPQTTKPKEVPTTK PTEEPTINTTKTNITTTLLTNNTTGNPKLTSQM ETFHSTSSEGNLSPSQVSTTSEHPSQPSSPPNT TRQQAYVEQKLISEEDLNSAVDHHHHHH (SEQ ID NO: 49) |
| RSV G B/B1 (NP_056862) | ANHKVTLTTVTVQTIKNHTEKNITTYLTQVPPE RVSSSKQPTTTSPIHTNSATTSPNTKSETHHTT AQTKGRTTTSTQTNKPSTKPRLKNPPKKPKDDY HFEVFNFVPCSICGNNQLCKSICKTIPSNKPKK KPTIKPTNKPTTKTTNKRDPKTPAKTTKKETTT NPTKKPTLTTTERDTSTSQSTVLDTTTLEHTIQ QQSLHSTTPENTPNSTQTPTASEPSTSNSTQNT QSHAQAYVEQKLISEEDLNSAVDHHHHHH (SEQ ID NO: 50) |

Example 2

Identification of Anti-RSV G-Specific Antibodies

Broadly neutralizing monoclonal antibodies against RSV G protein were recovered from memory B-cells (CD19+ CD27+IgG+) isolated from peripheral blood mononuclear cells (PBMCs) obtained through the San Diego Blood Bank. In short, CD22+ enriched B-cells were stained with fluorescently labeled antibodies to memory B cell surface markers and incubated with RSV Ga, Gb (labeled with Alexa Fluor 647 and 488, respectively, as described in Example 1), or the RSV G central conserved domain (CCD) biotin-conjugated peptide (SYM-1706). CD19/CD27/IgG/RSVGa/RSVGb or CD19/CD27/IgG/SYM-1706 (used in certain sorting experiments). Positive cells were sorted and single cells deposited into individual wells of a 96-well plate using a FACSAria II (BD Biosciences) or MoFlo XDP (Beckman Coulter). Plates were stored at −80° C. until processed. On average, approximately 10-25×10$^6$ B-cells per donor were surveyed.

Example 3

Recovery of Heavy and Light Chain Genes from Single B-Cells Specific to RSV Ga and Gb As described in Example 2, broadly neutralizing monoclonal antibodies against RSV were isolated from memory B-cells (CD19+CD27+IgG+) with reactivity to RSV Ga and Gb protein or the RSV G central conserved domain (CCD) biotin-conjugated peptide (SYM-1706). Heavy and light chain genes were then recovered by a two-step PCR approach from individual B-cells, cloned, and expressed in vitro as Fab antibodies.

First Strand cDNA Synthesis

Complementary DNA (cDNA) was generated from individually sorted cells using Invitrogen's Superscript III First Strand Synthesis kit (Superscript III kit, Cat No. 18080-051).

IgG Heavy and Light Chain Amplification by Nested PCR

IgG heavy and light chain variable regions (both kappa and lambda chains) were amplified from freshly prepared cDNA using a two-step, nested PCR approach. Subsequently, heavy and light chain PCR fragments were assembled into a single cassette to facilitate downstream cloning using an overlap extension PCR.

Step I Amplification

For Step I, 2.5 μL of freshly prepared cDNA generated, as mentioned above, was used as template to amplify heavy, kappa, and lambda light chains. A pool of primers specifically designed to the leader regions of antibody heavy chain (CB-5'LVH primers), kappa light chain (CB-5'LVk primers), and lambda light chain (CB-5' LVlam primers) were used (Table 2-4). A single reverse primer specifically designed to the CHI region, Ck, and CL region of the heavy chain, kappa light chain, and lambda light chain, respectively, were used in the Step I PCR reaction.

TABLE 2

| VH Step I forward primers (5'-3') | |
|---|---|
| Name | Sequence |
| CB-5'LVH1a | ATGGACTGGACCTGGAGGTTCCTC (SEQ ID NO: 51) |
| CB-5'LVH1b | ATGGACTGGACCTGGAGGATCCTC (SEQ ID NO: 52) |
| CB-5'LVH1c | ATGGACTGGACCTGGAGGGTCTTC (SEQ ID NO: 53) |
| CB-5'LVH1d | ATGGACTGGACCTGGAGCATCC (SEQ ID NO: 54) |
| CB-5'LVH2 | GGACATACTTTGTTCCACGCTCCTGC (SEQ ID NO: 55) |
| CB-5'LVH3a | AGGTGTCCAGTGTCAGGTGCAGC (SEQ ID NO: 56) |
| CB-5'LVH3b | AGGTGTCCAGTGTGAGGTGCAGC (SEQ ID NO: 57) |
| CB-5'LVH3c | AGGTGTCCAGTGTCAGGTACAGC (SEQ ID NO: 58) |
| CB-5'LVH4 | GCAGCTCCCAGATGGGTCCTG (SEQ ID NO: 59) |
| CB-5'LVH5 | TCAACCGCCATCCTCGCCCTC (SEQ ID NO: 60) |
| CB-5'LVH6 | GTCTGTCTCCTTCCTCATCTTCCTGC (SEQ ID NO: 61) |
| 3'CgCH1 | GGAAGGTGTGCACGCCGCTGGTC (SEQ ID NO: 62) |

TABLE 3

| Vk Step I forward primers (5'-3') | |
|---|---|
| Name | Sequence |
| CB-5'LVk1a | ATGAGGGTCCCCGCTCAGCTC (SEQ ID NO: 63) |
| CB-5'LVk1b | ATGAGGGTCCCTGCTCAGCTC (SEQ ID NO: 64) |
| CB-5'LVk1c | ATGAGAGTCCTCGCTCAGCTC (SEQ ID NO: 65) |
| CB-5'LVk2 | TGGGGCTGCTAATGCTCTGG (SEQ ID NO: 66) |
| CB-5'LVk3 | CCTCCTGCTACTCTGGCTCCCAG (SEQ ID NO: 67) |

TABLE 3-continued

| Vk Step I forward primers (5'-3') | |
|---|---|
| Name | Sequence |
| CB-5'LVk4 | TCTCTGTTGCTCTGGATCTCTGGTGC (SEQ ID NO: 68) |
| CB-5'LVk5 | CTCCTCAGCTTCCTCCTCCTTTGG (SEQ ID NO: 69) |
| CB-5'LVk6 | AACTCATTGGGTTTCTGCTGCTCTGG (SEQ ID NO: 70) |
| 3'Ck-Rev494 | GTGCTGTCCTTGCTGTCCTGCTC (SEQ ID NO: 71) |

TABLE 4

| VL Step I forward primers (5'-3') | |
|---|---|
| Name | Sequence |
| CB-5' LVlam1 | CTCCTCGCTCACTGCACAGG (SEQ ID NO: 72) |
| CB-5' LVlam2 | CTCCTCTCTCACTGCACAGG (SEQ ID NO: 73) |
| CB-5' LVlam3 | CTCCTCACTCGGGACACAGG (SEQ ID NO: 74) |
| CB-5' LVlam4 | ATGGCCTGGACCCCTCTCTG (SEQ ID NO: 75) |
| CB-5' LVlam5 | ATGGCATGGATCCCTCTCTTCCTC (SEQ ID NO: 76) |
| 3'Clam-Rev | CAAGCCAACAAGGCCACACTAGTG (SEQ ID NO: 77) |

Step II Amplification

1) For Step II, 2.5 μL of Step I PCR product generated from the reaction above was used as a template to amplify heavy, kappa, and lambda light chain genes. A pool of forward primers specifically designed to the framework 1 region of antibody heavy chain, kappa light chain, and lambda light chain were used (Table 5-7). A pool of reverse primers specifically designed to the heavy chain junction (3'SalIJH primers), kappa light chain junction (3'Jk primers), and a 5' region-specific primer corresponding to the lambda light chain (CB-VL primers) were used. Furthermore, Step II forward primers were engineered to introduce an SfiI restriction site, while the Step II heavy chain reverse primers were designed to introduce a SalI restriction site

TABLE 5

| VH Step II primers (5'-3') | |
|---|---|
| Name | Sequence |
| CB-VH1a | GCTCGCAGCATAGCCGGCCATGGCCCAGGTGCAGCTG GTGCAGTC (SEQ ID NO: 78) |
| CB-VH1b | GCTCGCAGCATAGCCGGCCATGGCCCAGGTCCAGCTG GTGCAGTC (SEQ ID NO: 79) |
| CB-VH1c | GCTCGCAGCATAGCCGGCCATGGCCCAGGTTCAGCTG GTGCAGTC (SEQ ID NO: 80) |
| CB-VH1d | GCTCGCAGCATAGCCGGCCATGGCCCAGGTCCAGCTT GTGCAGTC (SEQ ID NO: 81) |

TABLE 5-continued

| VH Step II primers (5'-3') | |
|---|---|
| Name | Sequence |
| CB-VH2a | GCTCGCAGCATAGCCGGCCATGGCCCAGGTCACCTTG AGGGAGTCTGG (SEQ ID NO: 82) |
| CB-VH2b | GCTCGCAGCATAGCCGGCCATGGCCCAGGTCACCTTG AAGGAGTCTGG (SEQ ID NO: 83) |
| CB-VH3a | GCTCGCAGCATAGCCGGCCATGGCCCAGGTGCAGCTG GTGGAGTC (SEQ ID NO: 84) |
| CB-VH3b | GCTCGCAGCATAGCCGGCCATGGCCGAGGTGCAGCTG TTGGAGTC (SEQ ID NO: 85) |
| CB-VH3c | GCTCGCAGCATAGCCGGCCATGGCCGAGGTGCAGCTG GTGGAGTC (SEQ ID NO: 86) |
| CB-VH3d | GCTCGCAGCATAGCCGGCCATGGCCCAGGTACAGCTG GTGGAGTCTG (SEQ ID NO: 87) |
| CB-VH4a | GCTCGCAGCATAGCCGGCCATGGCCCAGSTGCAGCTG (CAGGAG SEQ ID NO: 88) |
| CB-VH4b | GCTCGCAGCATAGCCGGCCATGGCCCAGGTGCAGCTA CAGCAGTGG (SEQ ID NO: 89) |
| CB-VH5 | GCTCGCAGCATAGCCGGCCATGGCCGAGGTGCAGCTG GTGCAGTC (SEQ ID NO: 90) |
| CB-VH6 | GCTCGCAGCATAGCCGGCCATGGCCCAGGTACAGCTG CAGCAGTCAG (SEQ ID NO: 91) |
| CB-VH7 | GCTCGCAGCATAGCCGGCCATGGCCCAGGTGCAGCTG GTGCAATCTG (SEQ ID NO: 92) |
| 3'SalIJH 1/2/4/5 | TGCGAAGTCGACGCTGAGGAGACGGTGACCAG (SEQ ID NO: 93) |
| 3'SalIJH3 | TGCGAAGTCGACGCTGAAGAGACGGTGACCATTG (SEQ ID NO: 94) |
| 3'SalIJH6 | TGCGAAGTCGACGCTGAGGAGACGGTGACCGTG (SEQ ID NO: 95) |

TABLE 6

| VK Step II primers (5'-3') | |
|---|---|
| Name | Sequence |
| CB-VK1a | CTACCGTGGCCTAGGCGGCCGACATCCAGATGACCCAG TCTCC (SEQ ID NO: 96) |
| CB-VK1b | CTACCGTGGCCTAGGCGGCCGACATCCAGTTGACCCAG TCTCC (SEQ ID NO: 97) |
| CB-VK1c | CTACCGTGGCCTAGGCGGCCGCCATCCAGTTGACCCAG TCTCC (SEQ ID NO: 98) |
| CB-VK2a | CTACCGTGGCCTAGGCGGCCGATRTTGTGATGACTCAG TCTCCACTC (SEQ ID NO: 99) |
| CB-VK3a | CTACCGTGGCCTAGGCGGCCGAAATTGTGTTGACGCAG TCTCCAG (SEQ ID NO: 100) |
| CB-VK3b | CTACCGTGGCCTAGGCGGCCGAAATTGTGTTGACACAG TCTCCAG (SEQ ID NO: 101) |
| CB-VK3c | CTACCGTGGCCTAGGCGGCCGAAATAGTGATGACGCAG TCTCCAG (SEQ ID NO: 102) |
| CB-Vk4 | CTACCGTGGCCTAGGCGGCCGACATCGTGATGACCCAG TCTCC (SEQ ID NO: 103) |

TABLE 6-continued

| VK Step II primers (5'-3') | |
|---|---|
| Name | Sequence |
| CB-Vk5 | CTACCGTGGCCTAGGCGGCCGAAACGACACTCACGCAGTCTCC (SEQ ID NO: 104) |
| CB-Vk6 | CTACCGTGGCCTAGGCGGCCGAAATTGTGCTGACTCAGTCTCCAG (SEQ ID NO: 105) |
| 3'Jk1/4 Rev IIa-L | GAAGACAGATGGTGCAGCCACAGTTCGTTTGATYTCCACCTTGGTC (SEQ ID NO: 106) |
| 3'Jk2 Rev IIb-L | GAAGACAGATGGTGCAGCCACAGTTCGTTTGATCTCCAGCTTGGTC (SEQ ID NO: 107) |
| 3'Jk3 Rev IIc-L | GAAGACAGATGGTGCAGCCACAGTTCGTTTGATATCCACTTTGGTC (SEQ ID NO: 108) |
| 3'Jk5 Rev IId-L | GAAGACAGATGGTGCAGCCACAGTTCGTTTAATCTCCAGTCGTGTC (SEQ ID NO: 109) |

TABLE 7

| VL Step II primers (5'-3') | |
|---|---|
| Name | Sequence |
| CB-VL1 | CTACCGTGGCCTAGGCGGCCAATTTTATGCTGACTCAGCCCCACTC (SEQ ID NO: 110) |
| CB-VL2 | CTACCGTGGCCTAGGCGGCCTCCTATGTGCTGACTCAGCC (SEQ ID NO: 111) |
| CB-VL3 | CTACCGTGGCCTAGGCGGCCCAGTCTGTGCTGACGCAGCC (SEQ ID NO: 112) |
| CB-VL4 | CTACCGTGGCCTAGGCGGCCCAGTCTGTCGTGACGCAGCC (SEQ ID NO: 113) |
| CB-VL5 | CTACCGTGGCCTAGGCGGCCCAGTCTGCCCTGACTCAGCC (SEQ ID NO: 114) |
| CB-VL6 | CTACCGTGGCCTAGGCGGCCTCTTCTGAGCTGACTCAGGACC (SEQ ID NO: 115) |
| CB-VL7 | CTACCGTGGCCTAGGCGGCCTCCTATGAGCTGACTCAGCCACC (SEQ ID NO: 116) |
| 3'Clam-Step II | CTCAGAGGAGGGYGGGAACAGAGTGAC (SEQ ID NO: 117) |

Step III Amplification: Overlap Extension PCR

For Step III, the heavy and light chain DNA fragments (Step II products) were linked into a single cassette via overlap extension PCR using a: 1) Fab linker (kappa or lambda; Table 8) amplified as outlined below which anneals to the 3' end of the light chain Step II fragment and the 5' end of the heavy chain Step II fragment and contains either the kappa or lambda constant region, 2) a forward overlap primer with an SfiI restriction site that anneals to the 5' end of the light chain, and 3) a reverse primer with a SalI restriction site that anneals to the 3' end of the heavy chain step II fragment (Table 9). This reaction results in a 1200 bp fragment (i.e., cassette) consisting of the light chain-linker-heavy chain. Following amplification, the PCR linker reaction product or the overlap extension PCR reaction product was separated on a 1% agarose gel and gel extracted according to manufacturer's instructions (Qiagen Gel Extraction Kit; Cat. No. 28706).

TABLE 8

| Nucleotide Sequence of Kappa and Lambda Linker | |
|---|---|
| Gene | Sequence |
| IGKC | CGAACTGTGGCTGCACCATCTGTCTTCATCTTCCCGCCATCTGATGAGCAGCTTAAATCTGGAACTGCCTCTGTTGTGTGCCTTCTAAATAACTTCTATCCCCGTGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTTACGCTTAGCAAAGCAGACTACGAGAAACACAAAGTCTACGCCTGCGAAGTCACCCATCAGGGCCTCAGCTCGCCCGTCACAAAGAGCTTCAACCGCGGAGAGTGTTAATCTAGAAATAAGGAGGATATAATTATGAAATACCTGCTGCCGACCGCAGCCGCTGGTCTGCTGCTGCTCGCAGCATAGCCGGCCATGGCC (SEQ ID NO: 118) |
| IGLC2 | GTCACTCTGTTCCCGCCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTACCTGAGCCTGACGCCTGAGCAGTGGAAGTCCCACAGAAGCTACAGCTGCCAGGTCACGCATGAAGGGAGCACCGTGGAGAAGACAGTGGCCCCTACAGAATGTTCATAATCTAGAAATAAGGAGGATATAATTATGAAATACCTGCTGCCGACCGCAGCCGCTGGTCTGCTGCTGCTCGCAGCATAGCCGGCCATGGCC (SEQ ID NO: 119) |

TABLE 9

| Linker primers (5'-3') | |
|---|---|
| Name | Sequence |
| FabLinker-F | CGAACTGTGGCTGCACCATCTGTCTTC (SEQ ID NO: 120) |
| FabLinker-R | GGCCATGGCCGGCTATGCTGCGAGC (SEQ ID NO: 121) |
| Lambda-Fab Linker F | GTCACTCTGTTCCCRCCCTCCTCTGAG (SEQ ID NO: 122) |
| Overlap-F | CTACCGTGGCCTAGGCGGCC (SEQ ID NO: 123) |
| Overlap-R | TGCGAAGTCGACGCTGARGAG (SEQ ID NO: 124) |

Digestion and Cloning into Bacterial Expression Vector

Following PCR purification (Qiagen) of the overlap extension PCR, the fragment was digested and the digested overlap product was then separated on a 1% agarose gel. The band corresponding to the overlap cassette (~1.1 kb) was purified by gel extraction (Qiagen). Finally, the digested overlap extension product was ligated and cloned into the pCB-Fab bacterial expression vector. All transformations were carried out using DH5a Max Efficiency cells (Invitrogen Corp., Cat. No. 18258-012). Approximately 100 μl of recovered cells were plated onto a 100 μg/mL carbenicillin plate supplemented with 20 mM glucose. Plates were incubated overnight at 37° C. to allow for colony growth.

Example 4

Fab Binding to RSV G and Monoclonal Antibody Rescue

Fab antibodies cloned in Example 3 were expressed in bacteria and again tested for their ability to bind to RSV Ga, RSV Gb, or the RSV G central conserved domain (CCD) peptide (SYM-1706: amino acid sequence: biotin-KQRQNKPPNKPNNDFHFEVFNFVPCSI CSNNPTCWA-ICKR; SEQ ID NO:125).

Bacterial supernatants were added to RSV Ga, Gb, CCD peptide, negative control actin, and anti-human F(ab)2 coated plates and incubated for 2 hours at 37° C. (except for the CCD peptide which was incubated on a Streptavidin coated plate and incubated for 2 hours at room temperature). CR9514 (an antibody based on 3D3, i.e., comprising the heavy and light chain variable region of 3D3, as disclosed in WO 2009/055711) was used as positive control against RSV Ga, Gb, CCD peptide, and anti-human F(ab)2 coated plates at a dilution of 0.1 μg/mL in 0.4% NFDM/PBS/0.05% Tween20. Mouse anti-actin (Sigma, Cat. No. A3853) was used at 1.25 μg/mL as positive control for bovine actin coated plates. Anti-HA HRP (Roche, Cat. No. 12013819001) was used as secondary antibody for bacterial supernatants. Anti-human Fab (Jackson Labs, Cat. No. 109-036-097) was used for CR9514 (comprising the variable regions of 3D3) control wells. Finally, goat anti-mouse HRP (Jackson Labs, Cat. No. 115-035-072) was used for the actin positive control. Following incubation, plates were washed four times in PBS/0.05% Tween20 and developed with 50 μL 1:1 v/v TMB:peroxide solution (Pierce, Cat No. 34021) for approximately 5 minutes. The reaction was immediately halted by the addition of 50 μL 2N $H_2SO_4$ and the absorbance at 450 nm was measured using an ELISA plate reader. Positive binding was indicated by an $OD_{450}$ greater than 0.5 (0.5-0.9 is moderate binding, >1 is strong binding) and a response that was 3-fold above background.

Based on ELISA results, about six clones on average with reactivity to target antigens were selected. Because each Fab antibody was originally cloned using a pool of framework 1-specific and junction-specific primers, the potential for cross-priming, especially for highly related primers, was high. For this reason, several bacterial clones representing each overlapped product were selected to sequence. Plasmid miniprep DNA was prepared according to manufacturer guidelines (Qiagen Miniprep kit Cat. No. 27106). Heavy and light chains corresponding to each clone selected were sequenced with the primers highlighted in Table 10. Sequences were analyzed, the closest germline identified, and CDR and framework regions determined. This information was subsequently used to design primers to clone and convert candidate antibodies into IgG.

TABLE 10

Sequencing Primers for Bacterial Fabs (5'-3')

| Gene | Sequence |
|---|---|
| SeqpCBFab-HCF | TGAAATACCTGCTGCCGACC (SEQ ID NO; 126) |
| Seq-PelB-Rev | CAGCAGACCAGCGGCTGC (SEQ ID NO: 127) |

Example 5

Cloning, Sequencing, and Purification of IgGs

Fab antibodies reactive to RSV Ga, Gb, and CCD peptide identified in the bacterial ELISA outlined in Example 4 were cloned and expressed as IgGs in the human embryonic kidney cells (293-F cells). IgGs were subsequently purified and quality-controlled by determining concentration, SDS-PAGE, and by size exclusion chromatography.

A. IgG Cloning and Sequencing Information

Fab antibodies identified in the bacterial ELISA (outlined in Example 4) were subsequently converted into IgGs by cloning the variable heavy and light domains (kappa and lambda) by restriction digest into the pCP9-kappa (SEQ ID NO:127) and pCP9-lambda (SEQ ID NO:128) expression vectors. Given the potential for cross-priming (aforementioned in Example 4), the initial amino acids of FR1 and the ending amino acids of the junction region for each bacterial clone selected for conversion into IgG frequently differed to those of its corresponding germline sequence. For this reason, primers specific to each antibody were designed to restore the FR1 and junction regions for both heavy and light chain genes of each bacterial clone selected. Heavy and light chains were amplified using the corresponding bacterial clone (expressed from the pCB-Fab vector in Example 4) and cloned in a sequential manner into the pCP9 expression vectors.

Amplification of the heavy chain resulted in an average sized fragment of 370 bp which was resolved on a 1% agarose gel and gel extracted according to manufacturer's instructions (Qiagen). The heavy chain fragment was then used to attach the HAVT20 leader sequence (5'-ATGGCCT-GCCCTGGCTTTCTCTGGGCACTTGTGATCTCCAC-CTGTCTTGAATTTTC CATGGCT-3' (SEQ ID NO:134); MACPGFLWALVISTCLEFSMA (SEQ ID NO:135)) by overlap extension PCR.

The corresponding overlap HAVT20-heavy chain product was subsequently PCR purified according to manufacturer's instructions (Qiagen). Ligations were carried out sequentially; that is, either the light chain was first digested and ligated or the corresponding heavy chain digested and inserted. Once either the light or heavy chain insertion was sequenced confirmed, a representative bacterial clone was selected, miniprep was prepared and used to clone the second chain (i.e., either light or heavy chain, depending on which was cloned first). For cloning the heavy chain fragment, the pCP9 vector and PCR purified heavy chain overlap product were digested with restriction enzymes BamHI HF (NEB, Cat. No. R3136L) and XhoI (NEB, Cat. No. R0146L). Digested pCP9 vector and heavy chain overlap product were then resolved on a 1% agarose gel and gel extracted (upper ~9.5 kB for pCP9 vector). Ligations were carried out at a 1:3 vector-to-insert ratio and transformed into DH5a Max Efficiency cells (Invitrogen Corp., Cat. No. 18258-012). Upon sequence confirmation, the second chain (e.g., light chain) was cloned. For cloning the light chain fragment, the pCP9 clone containing the corresponding heavy chain and the light chain PCR product were digested with NotI HF (NEB, Cat. No. R3189L) and XbaI (NEB, Cat. No. R0145L. The light chain was then ligated into the pCP9 vector containing the corresponding heavy chain gene and transformed into DH5a Max Efficiency cells. Several colonies were selected for sequencing and analyzed. Tables 11 and 12 show sequences of the antibody heavy and light chains CDR regions.

TABLE 11

Amino acid sequences of heavy chain variable regions (SEQ ID NO:)

| Clone | VH Germmline | CDR1 | CDR2 | CDR3 |
|---|---|---|---|---|
| CB2.1 | IGHV4-59 | SYFWN (25) | YIYGSGSADYNPSLKS (26) | SGFCTNDACYRRGSWFDP (27) |
| CB3.1 | IGHV1-46 | TYYIH (10) | MINTGSGVTSYAQKFQG (11) | MYSGSWYPFDY (12) |
| CB010.7 | IGHV3-30 | THGMH (7) | VMSYDGTKKYHADSVKG (8) | VGELRSFDWLLADGTAYYYYGMDV (9) |
| CB028.2 | IGVH1-18 | TYGIT (31) | WISGDSDNTNYAQNLQG (32) | ALAKWYCSSSSCFCGGGSCYSDY (33) |
| CB048.3 | IGHV3-30 | NHGMH (4) | VISYDGNKKYYADSVKG (5) | TTFYFDDSNYYEYLDY (6) |
| CB058.1 | IGHV3-23 | SYAMS (1) | AIRGSVDNTYYADSVKG (2) | DPALYCSGETCFSDLTD (3) |

TABLE 12

Amino acid sequences of light chain variable regions (SEQ ID NO:)

| Clone | VK/VL Germline | CDR1 | CDR2 | CDR3 |
|---|---|---|---|---|
| CB002.1 | IGKV1-39 | RASQSIDNYLN (28) | AASSLQS (29) | QQSYSTLT (30) |
| CB003.1 | GKV3-20 | RASQNINGNYLA (22) | EASSRAT (23) | QQYGTSPF (24) |
| CB010.7 | IGKV4-1 | KSSQSVLYSSNNKNYLA (19) | WASTREF (20) | HQYYSIP (21) |
| CB028.2 | IGKV1-39 | RASQGMSNYLN (34) | AASTLQS (35) | QQSFSTP (36) |
| CB048.3 | IGKVI-9 | RASQGIRSYLA (16) | AASTLQS (17) | QQLNTSPP (18) |
| CB058.1 | IGKV1-16 | RASQGINNYLA (13) | AASTLPS (14) | QHYIRYP (15) |

IgG Expression and Purification

To express each IgG, midi-preps of the pCP9 vectors containing both heavy and light chain genes of interest were prepared (Qiagen) and used to transfect 293-F cells using 293fectin per manufacturer's instructions (Invitrogen, Cat. No. 51-0031). Following transfection, cells were incubated for 72 hours to allow for sufficient IgG production. Cell media was then harvested and centrifuged to remove the cells. Purification was effected by column chromatography using a Protein A column (Protein A sepharose beads; Amersham, Cat. No. 17-0963-03). The eluate was then dialyzed against 4 liters of 20 mM Tris-HCl pH7.2, 150 mM NaCl twice. Finally, the dialyzed samples were concentrated down to about 1 mL with a 10 kDa Amicon Ultra column (Millipore).

A series of quality control steps were executed for each IgG to determine concentration and purity, and assess size. IgG concentration was determined initially via NANO-DROP® readings using a molar extinction coefficient for IgG of 210,000 M−1 cm−1. In addition, IgG concentration was confirmed by BCA assay (Thermo Fisher) according to supplier's instructions and by measurements using Protein A sensor tips on the Octet Red384 (ForteBio). As an additional quality control step, SDS-PAGE was performed under non-reducing and reducing conditions (i.e., ±DTT) followed by Bio-Safe Coomassie stain (Biorad) to visualize intact IgG or reduced heavy and light polypeptide chains. Finally, IgGs were quality controlled by size exclusion chromatography a Superdex 200 10/300 GL gel filtration column (Pharmacia).

Example 6

IgG Binding Assays

IgGs generated and quality controlled as described in Example 5 above, and anti-RSV G antibody CR9514 (comprising the variable regions of 3D3) were tested in ELISA assays for their ability to bind to recombinant RSV Ga and Gb protein. Briefly, 96 half-well ELISA plates (Costar) were coated with 50 μL of antigen in 1×PBS overnight [RSV Ga: 0.5 μg/mL; RSV Gb: 0.5 μg/mL; bovine actin: 1 μg/mL (Sigma); affinipure goat anti-human F(ab)2: 2 μg/mL (Jackson Immunoresearch). Plates were incubated overnight at 4° C. and blocked on the following day with 135 μL of 4% non-fat dried milk (NFDM, Biorad) in PBS and incubated for 2 hours at 37° C. mAbs were then diluted in 0.4% NFDM/PBS/0.05% Tween20 starting at 100 ng/mL and titrated down in 5-fold dilutions, and added to plates for 2 hours at 37° C. CR9514 (3D3) mAb was used as positive control against RSV Ga and Gb, and was titrated in a similar manner. Additionally, mouse anti-actin (Sigma, Cat. No. A3853) was used at 1.25 μg/mL as positive control for bovine actin coated plates. After incubation, plates were washed four times with PBS/0.05% Tween20. Secondary antibodies were added each at 1:1000 in 0.4% NFDM/PBS/

0.05% Tween20 and incubated for 40 minutes at 37° C. Anti-Fc HRP (Jackson Labs, Cat. No. 109-035-008) was used as secondary antibody for mAbs. Finally, goat anti-mouse HRP (Jackson Labs, Cat. No. 115-035-072) was used for the actin positive control. Following incubation, plates were washed four times in PBS/0.05% Tween20 and developed with 50 μL 1:1 v/v TMB:peroxide solution (Pierce, Cat No. 34021) for approximately 5 minutes. The reaction was immediately halted by the addition of 50 μL 2N $H_2SO_4$ and the absorbance at 450 nm was measured using an ELISA plate reader. The estimated EC50 values for binding (determined by titrating each IgG) for the antibodies, according to the disclosure, ranged between 1.0 and 2.0 ng/ml for RSV strain A/Long and between 0.5 and 2.5 ng/ml for strain B/B1.

Example 7

IgG Neutralization Assays

The anti-RSV antibodies were analyzed for their ability to bind to and neutralize RSV in solution as assessed by a plaque reduction assay. In this experiment, the virus and the antibodies were pre-incubated in the absence of target cells. The mixture was then added to the cells and virus infection was measured by a standard plaque reduction assay described herein. The anti-RSV antibodies were analyzed for their ability to neutralize several strains of RSV, including RSV A/A2 (ATCC Cat. No. VR-1540), RSV B/18537 (ATCC Cat. No. VR-1580) and RSV A/Long (ATCC Cat. No. VR-26). Antibodies CR9514 (3D3) and CR9505 (an antibody based on 131-2G, i.e., comprising the heavy and light chain variable region of 131-2G, as disclosed in WO 2009/055711) were used as reference.

Vero cells (ATCC, cat no: CCL-81; Manassas) were employed for host cell infection. Vero cells were grown in DMEM (HyClone, cat no: SH 30285.01) with 10% fetal bovine serum (FBS) (HyClone, cat no: SH30070.03), supplemented with 1% L-Glutamine (HyClone, cat no: SH30034.01) and 1% Penicillin-Streptomycin solution (HyClone, cat no: SV30010). The Vero cells were maintained in a 37° C. incubator with 5% CO2 and passaged twice per week.

On day 1 of the experiment, Vero cells were cultured in 24-well cell culture plates. The cells were plated at a density (approximately $9\times10^4$ cells per well) which allows formation of a cell monolayers (>80% confluence) by day 2. On day 2, each antibody was serially diluted in plain Eagle's minimal essential medium (EMEM, ATCC, cat no: 30-2003) that contained 10% baby rabbit complement (AbD Serotec, cat no. C12CAX). The final antibody concentrations tested were: 10 μg/mL, 1.3 μg/mL, 156 ng/mL, 19.5 ng/mL, 2.4 ng/mL, and 0.3 ng/mL (with the exception of CB010.7, which used antibody concentrations: 2.5 μg/mL, 312.5 ng/mL, 39.1 ng/mL, 4.9 ng/mL, 0.61 ng/mL, and 0.08 ng/mL). The virus was also diluted in plain EMEM to a concentration of 2000-3000 pfu/mL (100-150 pfu/50 μL) and 85 μL of the diluted RSV was added to 85 μL of each diluted antibody solution and mixed by pipetting. For the virus control sample, 85 μL of the diluted virus was added to 85 μL plain EMEM. The antibody-virus or virus control mixtures were incubated at 37° C. for 2 hours. Following incubation, the culture media was decanted from the 24-well cell culture plates containing the Vero host cells and 150 μL of the pre-incubated virus-antibody or virus-control mixture were then transferred to each well. Each test and control sample was prepared in triplicate. The cells were then incubated at 37° C. for one hour with mixing every 15 min.

Following the incubation period, 1 mL of overlay medium was added to each well (overlay medium contained EMEM, 2% FBS, 1% L-glutamine, 0.75% methylcellulose). The 24-well cell culture plates were then incubated at 37° C. (with 5% $CO_2$) for approximately 96-120 hours. Cell plates were fixed with 10% formalin for 1 hour at room temperature, washed 10 times with $ddH_2O$ and blocked with 5% non-fat dry milk (NFDM) in PBS at 37° C. for one hour. Following incubation, the blocking solution was decanted and 200 μL of HRP-conjugated mouse anti-RSV antibody (ab20686, Abcam, 1:750 dilution in 1% NFDM) was added to each well. The plates were incubated at 37° C. for 2 hours, and washed 10 times with $ddH_2O$. Following washing, 200 μL of TRUEBLUE® peroxidase substrate (KPL Cat. No. 50-78-02) was added to each well. The plates were developed for 10 min at room temperature. The plates were washed twice with $ddH_2O$ and dried on a paper towel and the number of blue plaques was counted.

The IC50 (effective dilution for 50% neutralization of plaque formation) was calculated using SPSS for Windows. The plaque reduction rate was calculated according to the following formula:

Plaque Reduction Rate (percentile)=1−[(average plaque number in each antibody dilution)/(average plaque number in virus control wells)]*100.

Table 13 lists the IC50 for a panel of antibodies for RSV strains A/A2 (ATCC Cat. No. VR-1540) and RSV B/18537 (ATCC Cat. no. VR-1580).

TABLE 13

Neutralization assay results for the top RSV G protein-specific monoclonal antibodies

| Strain Assay | RSV A A/A2 Neutralization IC50 (ng/mL) | RSV B B/18537 Neutralization IC50 (ng/mL) |
|---|---|---|
| CR9514 (3D3) | 40.7 | 33.0 |
| CB002.1 | 35.5 | 23.4 |
| CB003.1 | 31.5 | 24.6 |
| CB010.7 | 16.5 | 14.1 |
| CB028.2 | 11.0 | 19.6 |
| CB048.3 | 16.7 | 8.0 |
| CB058.1 | 14.4 | 4.2 |

Table 13 shows that the IC50 (effective dilution for 50% neutralization of plaque formation) of the antibodies and antigen-binding fragments for RSV strain A/A2 (ATCC Cat. No. VR-1540) was below 40 ng/ml and/or the IC50 for RSV strains B/18537 (ATCC Cat. No. VR-1589) was below 30 ng/ml.

In addition, IC50 for antibodies CB003.1, CB010.7 and control antibodies CR9505 (131-2G) and CR9514 (3D3) for RSV strain A/Long (ATCC Cat. No. VR-26) were 16, 12, 18, and 17 ng/mL, respectively.

Example 8

Construction of Fully Human Immunoglobulin Molecules (Human Monoclonal Antibodies) Including Codon Optimization and De-Risking Analysis The heavy and light chain variable regions (VH and VL) for each antibody clone isolated in Example 5 above were examined for the presence of free cysteines and potential post-translational modification sites including glycosylation, deamidation and oxidation sites. To remove these sites, amino acid mutations consisting of structurally conservative and/or germline-based substitutions are used (Table 14). Non-conserved cysteines in the variable regions were mutated to serine. For glycosylation sites, several mutations can be used, including replacement of asparagine for the conservative glutamine or germline mutations. Modifications to the deamidation sites include replacement of aspartic acid for asparagine and serine or alanine for glycine. Sites of potential oxidation are not modified. The nucleotide and amino acid sequences obtained from each VH and VL of the antibody clones were then codon-optimized for expression in human cells at GeneArt/Invitrogen. The variable regions of these functional variants were subsequently cloned directly by restriction digest for expression in the IgG expression vectors pCP9-kappa (See SEQ ID:127) and pCP9-gamma (See SEQ ID:128). BamHI, XhoI and/or SrfI were used to clone the variable heavy chains and NotI and AscI were used to clone the variable light chains. Nucleotide sequences for all constructs were verified according to standard techniques known to the skilled artisan.

TABLE 14

De-risking of RSV G protein specific monoclonal antibodies

| IgG identification | Variable Chain | Mutation | Reason |
|---|---|---|---|
| CB002.1 | Heavy | C102S C107S | Free cysteine |
| CB003.1 | Light | N30D | Deamidation |
| CB010.7 | NA | NA | NA |
| CB028.2 | Heavy | C105S C110S C112S C117S | Free cysteine |
| CB048.3 | Light | N92D | Glycosylation |
| CB058.1 | Heavy | C104S C109S | Free cysteine |

Example 9

Peptide Binding Studies by ELISA and Octet

Detailed epitope mapping was performed for the RSV G protein specific mAbs identified such as CB010.7 and CB030.1. Peptides were synthesized by Fmoc chemistry and purified by reversed phase high-performance liquid chromatography (HPLC). For the peptide-peptide interaction studies, some peptides were N-terminally biotinylated via an aminohexanoic acid (Ahx) spacer. The peptides were analyzed for identity by electrospray mass spectrometry. Samples were analyzed by ultra-performance liquid chromatography (UPLC, Alliance, Waters, Milford, Mass., USA) with a C18 reversed phase column and were detected with a photodiode array detector and a mass sensitive detector. A gradient at 25%/min for 25-100% acetonitrile (ACN) with solvent A ($H_2O$+0.05% trifluoroacetic acid [TFA]) and solvent B (ACN+0.05% TFA) was used. All reagents were at least HPLC grade.

The mAbs were tested for binding to biotinylated peptides that contain the central conserved region of RSV-G type A and B (Table 15). Avidin-coated 96-well microtiter plates were washed and incubated with 100 μL biotinylated peptide ($2.37\times10^{-7}$ M) in ELISA buffer (PBS+1% FBS+0.05% Tween20) for 1 hr at RT. Next, after washing, 180 μL of blocking buffer (PBS+10% FBS) per well was transferred to the wells and incubated 1 hr at RT. Subsequently, plates were washed and incubated with anti-human-HRP (Jackson ImmunoResearch), for 1 hr at RT. Following washing, 100 μL of o-Phenylenediamine horseradish peroxidase substrate (Thermo Scientific) was added to each well. The reaction was stopped after 10 min with 100 μL 1 M H2SO4. Absorption was read at 490 nm.

TABLE 15

RSV-G peptides used for antibody binding studies

| | |
|---|---|
| **Type A central region** | |
| Sym-1705 | biotin-KQRQNKPPNKPNNDFHFEVFNFVPCSICSNNPTCWAICKRIPNKKPGKKTTTKPTKK (SEQ ID NO: 129) |
| Sym-1706 | biotin-KQRQNKPPNKPNNDFHFEVFNFVPCSICSNNPTCWAICKR (SEQ ID NO: 125) |
| **Type B central region** | |
| Sym-1788 | biotin-KPRPKSPPKKPKDDYHFEVFNFVPCSICGNNQLCKSICKTIPSNKPKKKPTIKPTNK (SEQ ID NO: 130) |
| Sym-1789 | biotin-KPRPKSPPKKPKDDYHFEVFNFVPCSICGNNQLCKSICKT (SEQ ID NO: 131) |

Note:
underlined residues correspond to unglycosylated central conserved domain

Figure 3:
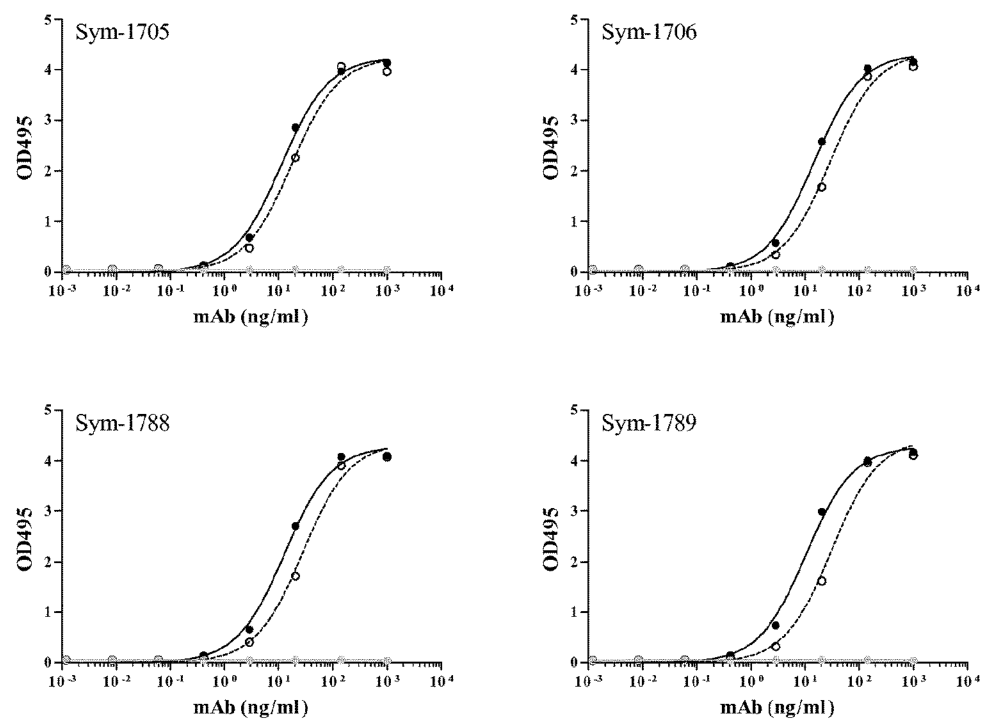
FIG. 3 shows binding of RSV G specific monoclonal antibodies to RSV G peptides (ELISA). Short and long RSV G peptides spanning the central conserved domain (Table 15) were used for binding experiments in an ELISA with varying concentrations of RSV G specific mAbs: CB003.1 (closed black circles, solid line), CB010.7 (open black circles, dashed line), or no monoclonal antibody (closed light grey circles).
Figure 4:
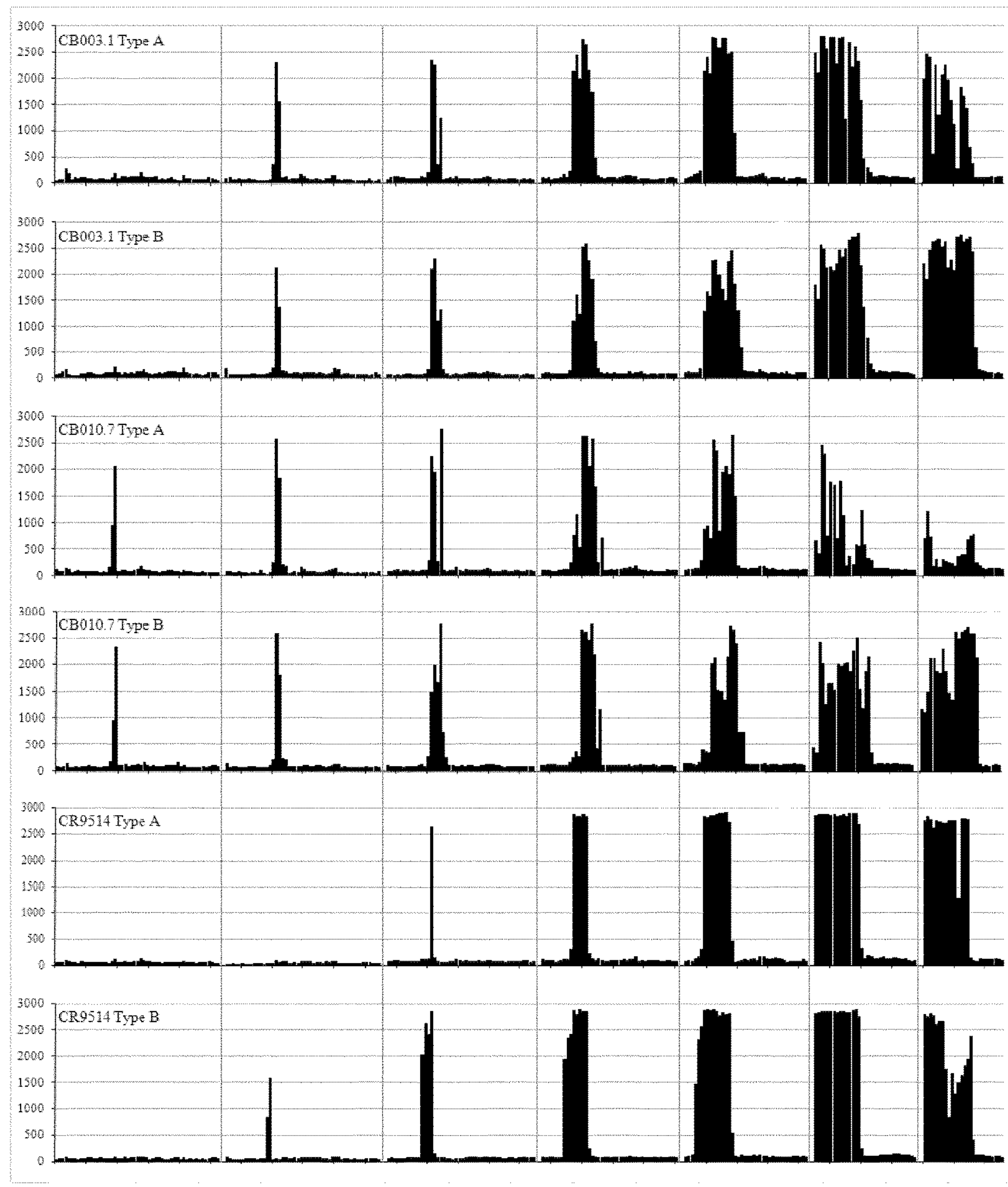
FIG. 4: Minimal epitope mapping by PepScan. The binding activity of RSV G protein specific antibodies to all fully overlapping 5-mer, 8-mer, 10-mer, 14-mer, 18-mer, 25-mer and 32-mer peptides of central region (residues 145-201 of RSV-G type A and type B). The binding activity with a peptide is shown as a vertical line proportional to the PepScan ELISA signal.

All mAbs described above bind to the RSV Ga and Gb protein (Example 6) and to the central region type A and type B peptides (data not shown). Titration of the antibodies CB003.1 and CB010.7 showed that these mAbs have IC50s of ~20 ng/mL for all four peptides (FIG. 3). Binding of the mAbs to the RSV G peptides was also determined using Streptavidin sensor tips on the Octet Red384 (ForteBio). Again, the mAbs showed cross-reactivity to both type A and type B peptides (Table 16). CB003.1 showed the highest response to both type A and type B peptides. CB010.7 showed slightly higher binding to type B, compared to type A peptides.

TABLE 16

Binding of RSV G specific mAbs to RSV-G peptides (Octet) [RU]

| Peptide | CB010.7 | CB003.1 |
|---|---|---|
| Sym-1705 | 1.25 | 3.48 |
| Sym-1706 | 1.74 | 3.36 |
| Sym-1788 | 1.94 | 3.28 |
| Sym-1789 | 2.96 | 3.20 |

RU: responsive units

Example 10

Mapping of Minimal Epitopes (PepScan)

In order to map the minimal epitope recognized by the mAbs, the reactivity was tested for peptides of multiple length (5, 8, 10, 14, 18, 25, or 32-mer) corresponding to the central region of RSV-G type A and B (residues 145-201) using PepScan analysis. The binding of antibodies to peptides was assessed in a PepScan-based ELISA. Each mAb was titrated to ensure that optimal binding was achieved and that nonspecific binding was avoided. Each of the credit-card-format polypropylene plates contained covalently linked peptides that were incubated overnight at 4° C. with mAb, between 1 and 10 ng/mL in PBS containing 5% horse serum (v/v), 5% OVA (w/v), and 1% (v/v) Tween 80, or in an alternative blocking buffer of PBS containing 4% horse serum (v/v), and 1% (v/v) Tween 80. After washing, the plates were incubated with a HRP-linked rabbit anti-mAb (DakoCytomation) for 1 hour at 25° C. After further washing, peroxidase activity was assessed using ABTS substrate and color development quantified using a charge-coupled device camera and an image-processing system.

The analysis shows the minimal peptide that binds the antibody corresponding to the energetic core of the epitope and the peptide with the highest binding that contains extra adjacent residues that also contribute to binding and contains the complete epitope. The reactivity of the antibodies to the peptides is summarized in Table 17 (residues depicted as caps). While all antibodies bind the central conserved domain, the critical residues for their binding are different. For two antibodies (CB003.1 and CB010.7) the minimal epitope is limited to the N-terminal CCD region (similar to 3D3, disclosed in WO2009/055711).

Example 11

Full Substitution Analysis (PepScan)

Figure 5:
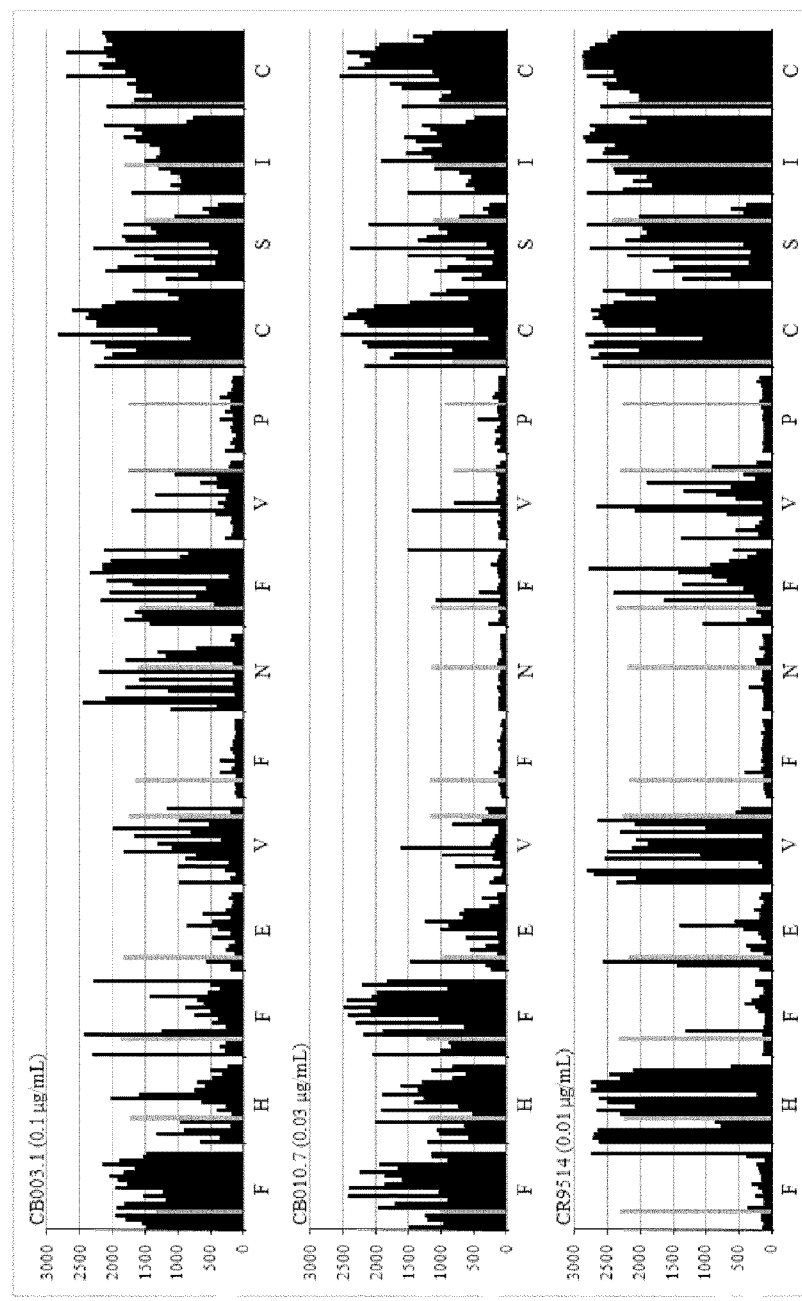
FIG. 5: Full substitution analysis of CB003.1 and CB010.7 epitope by PepScan. The binding activity of monoclonal antibodies CB003.1 and CB010.7 at 100 and 30 ng/mL, respectively, with a peptide is shown as a vertical line proportional to the Pepscan ELISA signal. Each group of 20 lines corresponds to the complete replacement set for each amino acid position in the original 14-mer peptide (FHFEVFNFVPCSIC (residues 99-112 of SEQ ID NO:49)). Within each group of 20 lines, the substitutions are in alphabetical order based on the one-letter amino acid code and the reactivity of the original 14-mer peptide is shown as a grey bar.

In order to identify the side chains critical for binding and to study the broadness of recognition for the known RSV strains, dedicated sets of peptides were synthesized. A full substitution analysis with a dedicated peptide array of 280 single substitution variant peptides for each position of the sequence FHFEVFNFVPCSIC (SEQ ID NO:132) recognized by antibodies CB003.1 and CB010.7 was performed and revealed the residues important for binding to these antibodies (FIG. 5). The epitope of these antibodies is comparable to the 3D3 epitope but recognized in a completely different manner. This is reflected by the substitution analysis which shows that the epitope of our antibodies have completely different essential residues compared to 3D3. Therefore, the recognition and mode of binding is very different. As shown in Example 7, the antibodies of the disclosure have a higher neutralizing capacity than 3D3.

3D3: FHFEVFNFVPCSIC (SEQ ID NO: 132)

CB010.7: FHFEVFNFVPCSIC (SEQ ID. NO: 132)

CB003.1: FHFEVFNFVPCSIC (SEQ ID. NO: 132)

The conserved residues important for binding are also summarized in Table 17 (critical residues depicted in bold).

Example 12

Alanine Scanning (PepScan)

Figure 6:
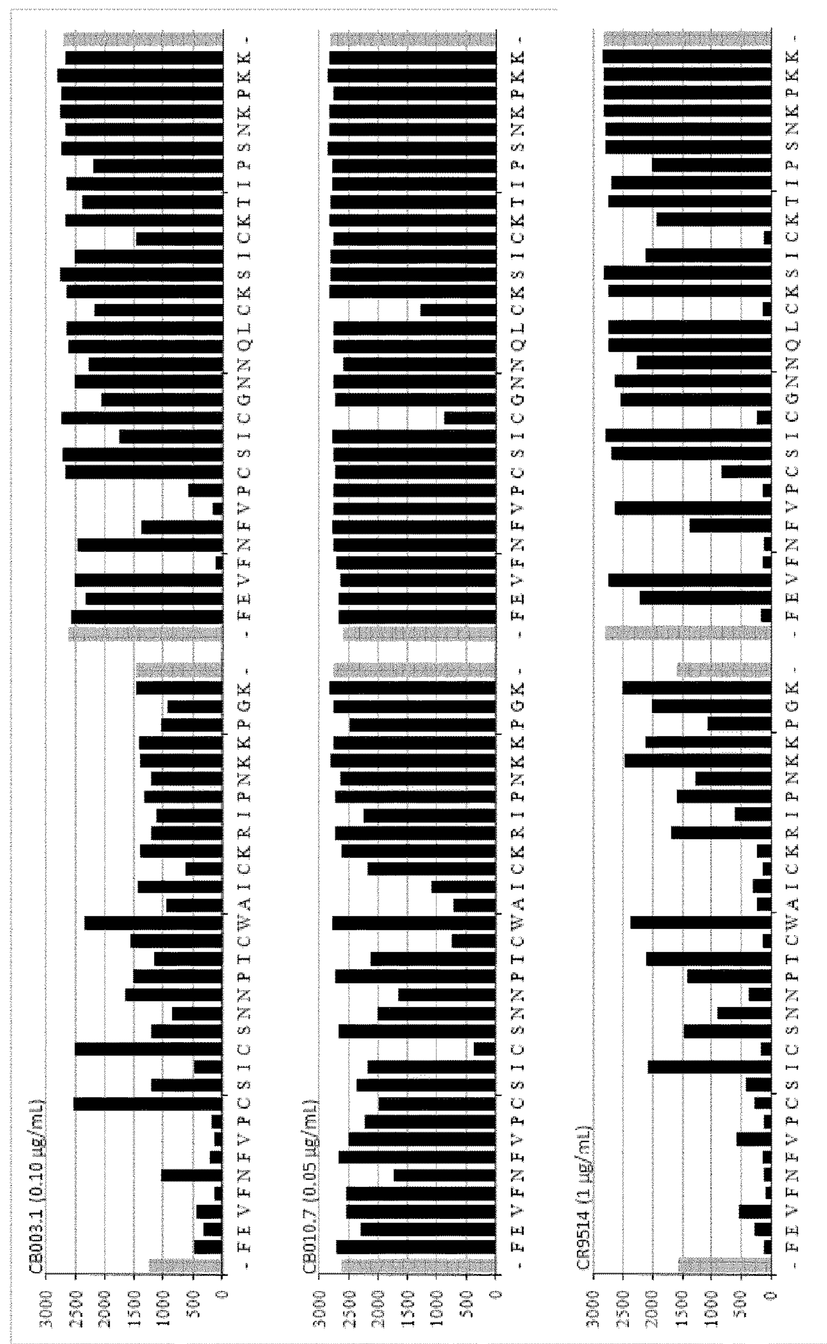
FIG. 6: Alanine scanning of RSV G protein central region (PepScan). Alanine substitutions at all positions of peptides corresponding to residues 161-192 of RSV-G central domain of type A (left panel) and type B (right panel) (residues 101-132 of SEQ ID NO:49 (type A) (residues 101-132 of SEQ ID NO:50, type B)). The alanine at position 180 of type A (residue 120 of SEQ ID NO:49) was substituted with glycine. The reactivity of the original peptide is shown as a grey bar.

A set of peptides were tested in which each position was substituted by an Alanine residue (FIG. 6). The side chains critical for binding antibodies are summarized in Table 17 (indicated in bold black).

Example 13

Binding to Natural Variant Peptides (PepScan)

Next, the antibodies were tested against the panel of 31 peptides that encompass the full diversity of the RSV-G central domain as it occurred in GenBank on Jan. 1, 2012. As shown in FIG. 7, almost all naturally occurring variant peptides of type A and B are recognized. CB003.1 shows lower binding to type A than to type B peptides. CB010.7 binds both type A and type B peptides equally well. The antibodies are critical to mutations at position 180 in the type A variant peptides. Mutation of Ser170Cys was not critical for CB010.7. Ile171Thr mutation was critical for CB003.1 binding, and Gln175Arg mutation was critical for CB003.1. The double mutation Ile181Phe; Ile184Ala was also critical for CB003.1. Naturally occurring variants critical for binding the four antibodies are summarized in Table 17 (indicated by underline).

Example 14

Prophylactic Efficacy of Anti-G mAbs

To determine whether the anti-G mAbs show in vivo prophylactic efficacy, mAbs CB0003.1 and CB010.7 were tested in the RSV-A/Long cotton rat model. At 24 hr before challenge, male cotton rats, inbred, seronegative for paramyxoviruses, 6-8 weeks old, weight range day−1 60-80 g, were injected intramuscularly with 5 mg/kg of CB003.1, CB010.7, SYNAGIS®, or vehicle (n=5 per group) in the upper hind leg (M. quadriceps). At day 0 the cotton rats were challenged with $10^{5.4}$ pfu RSV-A/Long by intranasal instillation with 100 μL (50 μL each nostril). After 96 hr animals were sacrificed to collect lungs and nasal turbinates: the lingual lobe for isolation of total RNA for total viral RNA load determination by qPCR, the remaining lung and the nasal turbinates for infectious viral load determination by pfu test. Blood samples were collected at day 0 before challenge (24 hr after mAb administration) and at study termination (96 hr after challenge) to confirm adequate dosing. The G mAbs reduced lung and nasal turbinate infectious virus titers and lung RNA virus load compared to vehicle (FIG. 8). Lung infectious virus titers ($\log_{10}$ PFU/g) were reduced by 2.456 and 1.559 $\log_{10}$ by antibodies CB003.1 and CB010.7, respectively, while prophylactic treatment with CR9514 (3D3) only resulted in a 0.801 $\log_{10}$ decrease.

Example 15

Therapeutic Efficacy of Anti-G mAbs

Figure 10:
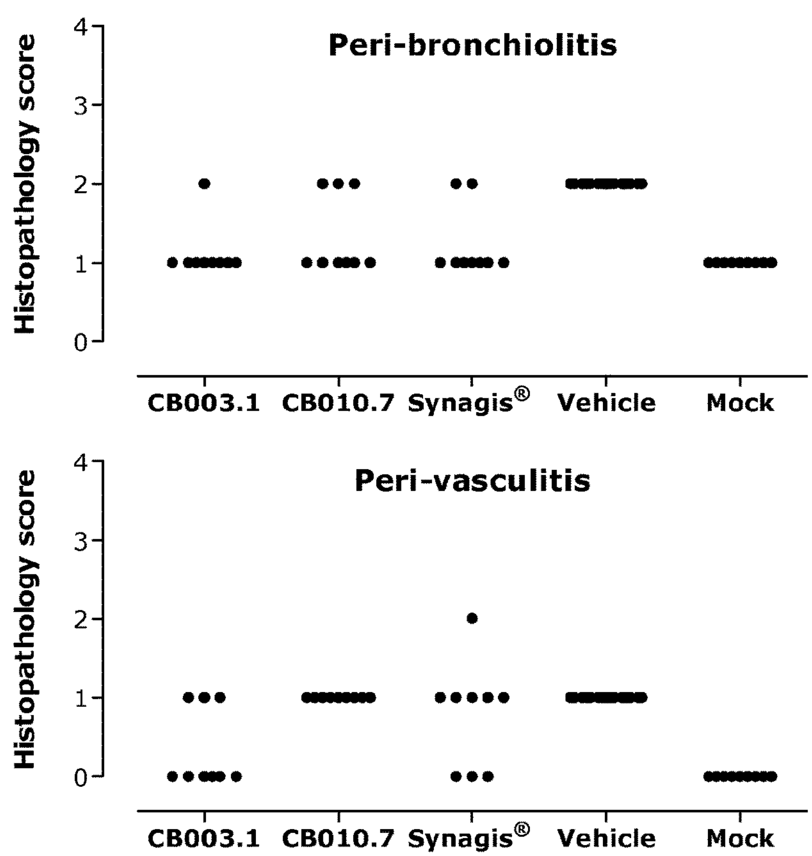
FIG. 10 shows the therapeutic efficacy of anti-RSV G mAbs in cotton rat RSV-A/Long model on histopathology scores at day 6 post challenge.

To determine whether the anti-G mAbs show in vivo therapeutic efficacy, mAbs CB003.1 and CB010.7 were tested in the RSV-A/Long cotton rat model. At day 0, male cotton rats, inbred, seronegative for paramyxoviruses, 6-8 weeks old, weight range day−1 60-80 g, were challenged with $10^{6.1}$ pfu RSV-A/Long by intranasal instillation with 100 μL (50 μL each nostril). After day 1 post challenge 50 mg/kg CB003.1, CB010.7, SYNAGIS® (n=14 per group) or vehicle (n=23 per group) were administered by intra-cardic injection. At day 4, 5 animals per group, randomly picked, were sacrificed to collect lungs and nasal turbinates: the lingual lobe for isolation of total RNA for total viral RNA load determination by qPCR, the remaining lung and the nasal turbinates for infectious viral load determination by pfu test. At day 6, all remaining animals (n=9 or 18 per group) were sacrificed to collect lung for pulmonary histopathology. Blood samples were collected at day 2 post challenge (24 hr after mAb administration), and at study termination (day 4 or day 6 after challenge) to confirm adequate dosing. The G mAbs reduced lung and nasal turbinate infectious virus titers, but not lung RNA virus load, compared to vehicle (FIG. 9). Lung infectious virus titers ($\log_{10}$ PFU/g) were reduced by 2.348 and 1.736 $\log_{10}$ by antibodies CB003.1 and CB010.7, respectively, while therapeutic treatment with CR9514 (3D3) only resulted in a 1.369 $\log_{10}$ decrease. Moreover, the new G mAbs reduced histopathology scores for peri-bronchiolitis, peri-vasculitis, interstitial pneumonitis and alveolitis (FIG. 10), while CR9514 (3D3) only reduced interstitial pneumonitis.

Sequences

```
>CB058.1 VH
                                            SEQ ID NO: 37
EVQLVESGGGLVQPGGSLRLSCVASGFTFSSYAMSWVRQAPGKGLEWVSA
IRGSVDNTYYADSVKGRFTISRDNSKNTLYLQMNSLRVEDTAVYYCAKDP
ALYCSGETCFSDLTDWGQGTLVTVSS
```

-continued

```
>CB058.1 VK
                                              SEQ ID NO: 38
DIQMTQSPSSLSASVGDRVTITCRASQGINNYLAWFQQKPGKAPKSLIYA
ASTLPSGVPSRFSGSGSGTDFTLTISSLQPEDSATYFCQHYIRYPHTFGQ
GTKLEIK

>CB048.3 VH
                                              SEQ ID NO: 39
QVQLVESGGGVVQPGRSLRLSCAASGFTFSNHGMHWVRQAPGKGLEWVAV
ISYDGNKKYYADSVKGRFTVSRDNSKNTLSLQMDSLRAEDTAIYYCAKTT
FYFDDSNYYEYLDYWGQGTLVTVSS

>CB048.3 VK
                                              SEQ ID NO: 40
DIQLTQSPSFLSASVGDRVTITCRASQGIRSYLAWYQQKPGKAPKLLIYA
ASTLQSGVPSRFSGGGSGTEFTLTISSLQPEDSATYYCQQLNTSPPYTFG
QGTKLEIK

>CB010.7 VH
                                              SEQ ID NO: 41
QVQLVESGGGVVQPGRSLRLSCAASGFTFNTHGMHWVRQAPGKGLEWVAV
MSYDGTKKYHADSVKGRFTISRDNSKNTLYLQMNSLRVEDTAIYYCAKVG
ELRSFDWLLADGTAYYYYGMDVWGQGTTVTVSS

>CB010.7 VK
                                              SEQ ID NO: 42
DIVMTQSPDSLAVSLGERATINCKSSQSVLYSSNNKNYLAWFQQKPGQPP
RLLINWASTREFGVPDRFSGSGSGTDFTLTISSLQAEDVAIYYCHQYYSI
PLTFGGGTKVEIK

>CB003.1 VH
                                              SEQ ID NO: 43
QVQLVQSGPELRKPGASVTVSCKASGYTFTTYYIHWVRQAPGGGLDWMGM
INTGSGVTSYAQKFQGRVAMTRDTSTSTVFMELSSLRFEDTALYYCARMY
SGSWYPFDYWGQGALVTVSS

>CB003.1 VK
                                              SEQ ID NO: 44
EIVLTQSPGILSLSPGERATLSCRASQNINGNYLAWYQQKPGLAPRLLIY
EASSRATGIPDRFSGSGSGTDFTLTISSLEPEDFGVYYCQQYGTSPFFTF
GPGTKVDIK

>CB028.2 VH
                                              SEQ ID NO: 45
QVQLVQSGAEVKKPGASVKVSCKASGYTFTTYGITWVRQAPGQGLEWMGW
ISGDSDNTNYAQNLQGRVTLTTDISTRTAYMELRSLKPDDTAMYYCARAL
AKWYCSSSSCFCGGGSCYSDYWGQGTLVTVSS

>CB028.2 VK
                                              SEQ ID NO: 46
DIQMTQSPSSLSASVGDRVTITCRASQGMSNYLNWYQQKPGKAPELLIYA
ASTLQSGVPSRFSGSGSGTDFTLTINSLQPEDFATYFCQQSFSTPLTFGG
GTKVEIK

>CB002.1 VH
                                              SEQ ID NO: 47
QVQLQESGPRLVKPSETLSLTCTVSGGSTSSYFWNWIRQPPGKGLEWIGY
IYGSGSADYNPSLKSRVTISIDTSKTQFSLKLTSVTAADTAVYYCARSGF
CTNDACYRRGSWFDPWGQGTLVTVSS

>CB002.1 VK
                                              SEQ ID NO: 48
DIQMTQSPSSLSASVGDRVTITCRASQSIDNYLNWYQQKPGKAPKLLIYA
ASSLQSGVPSRFSGSGSGTDFTLTVSSLHPEDFATYYCQQSYSTLTWTFG
QGTKVEIK

(pCP9-kappa sequence)
                                             SEQ ID NO: 127
TACTCTTCCTTTTTCAATATTATTGAAGCATTTATCAGGGTTATTGTCTC
ATGAGCGGATACATATTTGAATGTATTTAGAAAAATAAACAAATAGGGGT
TCCGCGCACATTTCCCCGAAAAGTGCCACCTGACGTCGACGGATCGGGAG
ATCTCCCGATCCCCTATGGTGCACTCTCAGTACAATCTGCTCTGATGCCG
CATAGTTAAGCCAGTATCTGCTCCCTGCTTGTGTGTTGGAGGTCGCTGAG
TAGTGCGCGAGCAAAATTTAAGCTACAACAAGGCAAGGCTTGACCGACAA
TTGCATGAAGAATCTGCTTAGGGTTAGGCGTTTTGCGCTGCTTCGCTAGG
TGGTCAATATTGGCCATTAGCCATATTATTCATTGGTTATATAGCATAAA
TCAATATTGGCTATTGGCCATTGCATACGTTGTATCCATATCATAATATG
TACATTTATATTGGCTCATGTCCAACATTACCGCCATGTTGACATTGATT
ATTGACTAGTTATTAATAGTAATCAATTACGGGGTCATTAGTTCATAGCC
CATATATGGAGTTCCGCGTTACATAACTTACGGTAAATGGCCCGCCTGGC
```

-continued

```
TGACCGCCCAACGACCCCCGCCCATTGACGTCAATAATGACGTATGTTCC
CATAGTAACGCCAATAGGGACTTTCCATTGACGTCAATGGGTGGAGTATT
TACGGTAAACTGCCCACTTGGCAGTACATCAAGTGTATCATATGCCAAGT
ACGCCCCCTATTGACGTCAATGACGGTAAATGGCCCGCCTGGCATTATGC
CCAGTACATGACCTTATGGGACTTTCCTACTTGGCAGTACATCTACGTAT
TAGTCATCGCTATTACCATGGTGATGCGGTTTTGGCAGTACATCAATGGG
CGTGGATAGCGGTTTGACTCACGGGGATTTCCAAGTCTCCACCCCATTGA
CGTCAATGGGAGTTTGTTTTGGCACCAAAATCAACGGGACTTTCCAAAAT
GTCGTAACAACTCCGCCCCATTGACGCAAATGGGCGGTAGGCGTGTACGG
TGGGAGGTCTATATAAGCAGAGCTCGTTTAGTGAACCGTCAGATCGCCTG
GAGACGCCATCCACGCTGTTTTGACCTCCATAGAAGACACCGGGACCGAT
CCAGCCTCCGCGGCCGGGAACGGTGCATTGGAAGCTTGGTACCGAGCTCG
GATCCTTAATTAACTCGAGGCCCGAGCCCGGGCGAGCCCAGACACTGGAC
GCTGAACCTCGCGGACAGTTAAGAACCCAGGGGCCTCTGCGCCCTGGGCC
CAGCTCTGTCCCACACCGCGGTCACATGGCACCACCTCTCTTGCAGCCTC
CACCAAGGGCCCATCGGTCTTCCCCCTGGCACCCTCCTCCAAGAGCACCT
CTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGG
TGACCGTGCCCTCCAGCAGCTTGGGCACCCAGACCTACATCTGCAACGTG
AATCACAAGCCCAGCAACACCAAGGTGGACAAGAGAGTTGGTGAGAGGCC
AGCACAGGGAGGGAGGGTGTCTGCTGGAAGCCAGGCTCAGCGCTCCTGCC
TGGACGCATCCCGGCTATGCAGTCCCAGTCCAGGGCAGCAAGGCAGGCCC
CGTCTGCCTCTTCACCCGGAGGCCTCTGCCCGCCCCACTCATGCTCAGGG
AGAGGGTCTTCTGGCTTTTTCCCCAGGCTCTGGGCAGGCACGGGCTAGGT
GCCCCTAACCCAGGCCCTGCACACAAAGGGGCAGGTGCTGGGCTCAGACC
TGCCAAGAGCCATATCCGGGAGGACCCTGCCCCTGACCTAAGCCCACCCC
AAAGGCCAAACTCTCCACTCCCTCAGCTCGGACACCTTCTCTCCTCCCAG
ATTCCAGTAACTCCCAATCTTCTCTCTGCAGAGCCCAAATCTTGTGACAA
AACTCACACATGCCCACCGTGCCCAGGTAAGCCAGCCCAGGCCTCGCCCT
CCAGCTCAAGGCGGGACAGGTGCCCTAGAGTAGCCTGCATCCAGGGACAG
GCCCCAGCCGGGTGCTGACACGTCCACCTCCATCTCTTCCTCAGCACCTG
AACTCCTGGGGGGACCGTCAGTCTTCCTCTTCCCCCCAAAACCCAAGGAC
ACCCTCATGATCTCCCGGACCCCTGAGGTCACATGCGTGGTGGTGGACGT
GAGCCACGAAGACCCTGAGGTCAAGTTCAACTGGTACGTGGACGGCGTGG
AGGTGCATAATGCCAAGACAAAGCCGCGGGAGGAGCAGTACAACAGCACG
TACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCG
AGAAAACCATCTCCAAAGCCAAAGGTGGGACCCGTGGGGTGCGAGGGCCA
CATGGACAGAGGCCGGCTCGGCCCACCCTCTGCCCTGAGAGTGACCGCTG
TACCAACCTCTGTCCCTACAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTATAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAATGAGCTAGC
GAATTCACCGGTACCAAGCTTAAGTTTAAACCGCTGATCAGCCTCGACTG
TGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGA
AATTGCATCGCATTGTCTGAGTAGGTGTCATTCTATTCTGGGGGGTGGGG
TGGGGCAGGACAGCAAGGGGGAGGATTGGGAAGACAATAGCAGGCATGCT
GGGGATGCGGTGGGCTCTATGGCTTCTGAGGCGGAAAGAACCAGCTGGGG
CTCTAGGGGGTATCCCCACGCGCCCTGTAGCGGCGCATTAAGCGCGGCGG
GTGTGGTGGTTACGCGCAGCGTGACCGCTACACTTGCCAGCGCCTAGCGC
CCGCTCCTTTCGCTTTCTTCCCTTCCTTTCTCGCCACGTTCGCCGGCTTT
CCCCGTCAAGCTCTAAATCGGGGGCTCCCTTTAGGGTTCCGATTTAGTGC
TTTACGGCACCTCGACCCCAAAAAACTTGATTAGGGTGATGGTTCACGTA
GTGGGCCATCGCCCTGATAGACGGTTTTTCGCCCTTTGACGTTGGAGTCC
ACGTTCTTTAATAGTGGACTCTTGTTCCAAACTGGAACAACACTCAACCC
TATCTCGGTCTATTCTTTTGATTTATAAGGGATTTTGCCGATTTCGGCCT
ATTGGTTAAAAAATGAGCTGATTTAACAAAAATTTAACGCGAATTAATTC
TGTGGAATGTGTGTCAGTTAGGGTGTGGAAAGTCCCCAGGCTCCCCAGCA
GGCAGAAGTATGCAAAGCATGCATCTCAATTAGTCAGCAACCAGGTGTGG
AAAGTCCCCAGGCTCCCCAGCAGGCAGAAGTATGCAAAGCATGCATCTCA
ATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTT
TATTTATGCAGAGGCCGAGGCCGCCTCTGCCTCTGAGCTATTCCAGAAGT
AGTGAGGAGGCTTTTTTGGAGGCCTAGGCTTTTGCAAAAAGCTCCCGGGA
GCTTGGATATCCATTTTCGGATCTGATCAAGAGACAGGATGAGGATCGTT
TCGCATGATTGAACAAGATGGATTGCACGCAGGTTCTCCGGCCGCTTGGG
TGGAGAGGCTATTCGGCTATGACTGGGCACAACAGACAATCGGCTGCTCT
GATGCCGCCGTGTTCCGGCTGTCAGCGCAGGGGCGCCCGGTTCTTTTTGT
CAAGACCGACCTGTCCGGTGCCCTGAATGAACTGCAGGACGAGGCAGCGC
GGCTATCGTGGCTGGCCACGACGGGCGTTCCTTGCGCAGCTGTGCTCGAC
GTTGTCACTGAAGCGGGAAGGGACTGGCTGCTATTGGGCGAAGTGCCGGG
GCAGGATCTCCTGTCATCTCACCTTGCTCCTGCCGAGAAAGTATCCATCA
TGGCTGATGCAATGCGGCGGCTGCATACGCTTGATCCGGCTACCTGCCCA
TTCGACCACCAAGCGAAACATCGCATCGAGCGAGCACGTACTCGGATGGA
AGCCGGTCTTGTCGATCAGGATGATCTGGACGAAGAGCATCAGGGGCTCG
CGCCAGCCGAACTGTTCGCCAGGCTCAAGGCGCGCATGCCCGACGGCGAG
```

-continued

GATCTCGTCGTGACCCATGGCGATGCCTGCTTGCCGAATATCATGGTGGA
AAATGGCCGCTTTTCTGGATTCATCGACTGTGGCCGGCTGGGTGTGGCGG
ACCGCTATCAGGACATAGCGTTGGCTACCCGTGATATTGCTGAAGAGCTT
GGCGGCGAATGGGCTGACCGCTTCCTCGTGCTTTACGGTATCGCCGCTCC
CGATTCGCAGCGCATCGCCTTCTATCGCCTTCTTGACGAGTTCTTCTGAG
CGGGACTCTGGGGTTCGGTGCTACGAGATTTCGATTCCACCGCCGCCTTC
TATGAAAGGTTGGGCTTCGGAATCGTTTTCCGGGACGCCGGCTGGATGAT
CCTCCAGCGCGGGGATCTCATGCTGGAGTTCTTCGCCCACCCCAACTTGT
TTATTGCAGCTTATAATGGTTACAAATAAAGCAATAGCATCACAAATTTC
ACAAATAAAGCATTTTTTTCACTGCATTCTAGTTGTGGTTTGTCCAAACT
CATCAATGTATCTTATCATGTCTGTATACCGTCGACCTCTAGCTAGAGCT
TGGCGTAATCATGGTCATAGCTGTTTCCTGTGTGAAATTGTTATCCGCTC
ACAATTCCACACAACATACGAGCCGGAAGCATAAAGTGTAAAGCCTGGGG
TGCCTAATGAGTGAGCTAACTCACATTAATTGCGTTGCGCTCACTGCCCG
CTTTCCAGTCGGGAAACCTGTCGTGCCAGAATTGCATGAAGAATCTGCTT
AGGGTTAGGCGTTTTGCGCTGCTTCGCTAGGTGGTCAATATTGGCCATTA
GCCATATTATTCATTGGTTATATAGCATAAATCAATATTGGCTATTGGCC
ATTGCATACGTTGTATCCATATCATAATATGTACATTTATATTGGCTCAT
GTCCAACATTACCGCCATGTTGACATTGATTATTGACTAGTTATTAATAG
TAATCAATTACGGGGTCATTAGTTCATAGCCCATATATGGAGTTCCGCGT
TACATAACTTACGGTAAATGGCCCGCCTGGCTGACCGCCCAACGACCCCC
GCCCATTGACGTCAATAATGACGTATGTTCCCATAGTAACGCCAATAGGG
ACTTTCCATTGACGTCAATGGGTGGAGTATTTACGGTAAACTGCCCACTT
GGCAGTACATCAAGTGTATCATATGCCAAGTACGCCCCCTATTGACGTCA
ATGACGGTAAATGGCCCGCCTGGCATTATGCCCAGTACATGACCTTATGG
GACTTTCCTACTTGGCAGTACATCTACGTATTAGTCATCGCTATTACCAT
GGTGATGCGGTTTTGGCAGTACATCAATGGGCGTGGATAGCGGTTTGACT
CACGGGGATTTCCAAGTCTCCACCCCATTGACGTCAATGGGAGTTTGTTT
TGGCACCAAAATCAACGGGACTTTCCAAAATGTCGTAACAACTCCGCCCC
ATTGACGCAAATGGGCGGTAGGCGTGTACGGTGGGAGGTCTATATAAGCA
GAGCTCGTTTAGTGAACCGTCAGATCGCCTGGAGACGCCATCCACGCTGT
TTTGACCTCCATAGAAGACACCGGGACCGATCCAGCCTCCGCGGCCGGGA
ACGGTGCATTGGAAGCTTGGTACCGGTGAATTCGGCGCGCCAGATCTGCG
GCCGCTAGGAAGAAACTCAAAACATCAAGATTTTAAATACGCTTCTTGGT
CTCCTTGCTATAATTATCTGGGATAAGCATGCTGTTTTCTGTCTGTCCCT
AACATGCCCTGTGATTATCCGCAAACAACACACCCAAGGGCAGAACTTTG
TTACTTAAACACCATCCTGTTTGCTTCTTTCCTCAGGAACTGTGGCTGCA
CCATCTGTCTTCATCTTCCCGCCATCTGATGAGCAGTTGAAATCTGGAAC
TGCCTCTGTTGTGTGCCTGCTGAATAACTTCTATCCCAGAGAGGCCAAAG
TACAGTGGAAGGTGGATAACGCCCTCCAATCGGGTAACTCCCAGGAGAGT
GTCACAGAGCAGGACAGCAAGGACAGCACCTACAGCCTCAGCAGCACCCT
GACGCTGAGCAAAGCAGACTACGAGAAACACAAAGTCTACGCCTGCGAAG
TCACCCATCAGGGCCTGAGCTCGCCCGTCACAAAGAGCTTCAACAGGGGA
GAGTGTTAGTTAACGGATCGATCCGAGCTCGGTACCAAGCTTAAGTTTAA
ACCGCTGATCAGCCTCGACTGTGCCTTCTAGTTGCCAGCCATCTGTTGTT
TGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGG
GAAGACAATAGCAGGCATGCTGGGGATGCGGTGGGCTCTATGGCTTCTGA
GGCGGAAAGAACCAGCTGCATTAATGAATCGGCCAACGCGCGGGGAGAGG
CGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTA
ATACGGTTATCCACAGAATCAGGGGATAACGCAGGAAAGAACATGTGAGC
AAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCA
AGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTA
ACTATCGTCTTGAGTCCAACCCGGTAAGACACGACTTATCGCCACTGGCA
GCAGCCACTGGTAACAGGATTAGCAGAGCGAGGTATGTAGGCGGTGCTAC
AGAGTTCTTGAAGTGGTGGCCTAACTACGGCTACACTAGAAGAACAGTAT
TTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTT
TGATCTTTTCTACGGGGTCTGACGCTCAGTGGAACGAAAACTCACGTTAA
GGGATTTTGGTCATGAGATTATCAAAAAGGATCTTCACCTAGATCCTTTT
AAATTAAAAATGAAGTTTTAAATCAATCTAAAGTATATATGAGTAAACTT
GGTCTGACAGTTACCAATGCTTAATCAGTGAGGCACCTATCTCAGCGATC
TGTCTATTTCGTTCATCCATAGTTGCCTGACTCCCCGTCGTGTAGATAAC
TACGATACGGGAGGGCTTACCATCTGGCCCCAGTGCTGCAATGATACCGC
GAGACCCACGCTCACCGGCTCCAGATTTATCAGCAATAAACCAGCCAGCC
GGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGT
TACATGATCCCCCATGTTGTGCAAAAAAGCGGTTAGCTCCTTCGGTCCTC
CGATCGTTGTCAGAAGTAAGTTGGCCGCAGTGTTATCACTCATGGTTATG
GCAGCACTGCATAATTCTCTTACTGTCATGCCATCCGTAAGATGCTTTTC
TGTGACTGGTGAGTACTCAACCAAGTCATTCTGAGAATAGTGTATGCGGC

-continued

GACCGAGTTGCTCTTGCCCGGCGTCAATACGGGATAATACCGCGCCACAT
AGCAGAACTTTAAAAGTGCTCATCATTGGAAAACGTTCTTCGGGGCGAAA
ACTCTCAAGGATCTTACCGCTGTTGAGATCCAGTTCGATGTAACCCACTC
GTGCACCCAACTGATCTTCAGCATCTTTTACTTTCACCAGCGTTTCTGGG
TGAGCAAAAACAGGAAGGCAAAATGCCGCAAAAAAGGGAATAAGGGCGAC
ACGGAAATGTTGAATACTCA (pCP9-lambda sequence)

SEQ ID NO: 128

TACTCTTCCTTTTTCAATATTATTGAAGCATTTATCAGGGTTATTGTCTC
ATGAGCGGATACATATTTGAATGTATTTAGAAAAATAAACAAATAGGGGT
TCCGCGCACATTTCCCCGAAAAGTGCCACCTGACGTCGACGGATCGGGAG
ATCTCCCGATCCCCTATGGTGCACTCTCAGTACAATCTGCTCTGATGCCG
CATAGTTAAGCCAGTATCTGCTCCCTGCTTGTGTGTTGGAGGTCGCTGAG
TAGTGCGCGAGCAAAATTTAAGCTACAACAAGGCAAGGCTTGACCGACAA
TTGCATGAAGAATCTGCTTAGGGTTAGGCGTTTTGCGCTGCTTCGCTAGG
TGGTCAATATTGGCCATTAGCCATATTATTCATTGGTTATATAGCATAAA
TCAATATTGGCTATTGGCCATTGCATACGTTGTATCCATATCATAATATG
TACATTTATATTGGCTCATGTCCAACATTACCGCCATGTTGACATTGATT
ATTGACTAGTTATTAATAGTAATCAATTACGGGGTCATTAGTTCATAGCC
CATATATGGAGTTCCGCGTTACATAACTTACGGTAAATGGCCCGCCTGGC
TGACCGCCCAACGACCCCCGCCCATTGACGTCAATAATGACGTATGTTCC
CATAGTAACGCCAATAGGGACTTTCCATTGACGTCAATGGGTGGAGTATT
TACGGTAAACTGCCCACTTGGCAGTACATCAAGTGTATCATATGCCAAGT
ACGCCCCCTATTGACGTCAATGACGGTAAATGGCCCGCCTGGCATTATGC
CCAGTACATGACCTTATGGGACTTTCCTACTTGGCAGTACATCTACGTAT
TAGTCATCGCTATTACCATGGTGATGCGGTTTTGGCAGTACATCAATGGG
CGTGGATAGCGGTTTGACTCACGGGGATTTCCAAGTCTCCACCCCATTGA
CGTCAATGGGAGTTTGTTTTGGCACCAAAATCAACGGGACTTTCCAAAAT
GTCGTAACAACTCCGCCCCATTGACGCAAATGGGCGGTAGGCGTGTACGG
TGGGAGGTCTATATAAGCAGAGCTCGTTTAGTGAACCGTCAGATCGCCTG
GAGACGCCATCCACGCTGTTTTGACCTCCATAGAAGACACCGGGACCGAT
CCAGCCTCCGCGGCCGGGAACGGTGCATTGGAAGCTTGGTACCGAGCTCG
GATCCTTAATTAACTCGAGGCCCGAGCCCGGGCGAGCCCAGACACTGGAC
GCTGAACCTCGCGGACAGTTAAGAACCCAGGGGCCTCTGCGCCCTGGGCC
CAGCTCTGTCCCACACCGCGGTCACATGGCACCACCTCTCTTGCAGCCTC
CACCAAGGGCCCATCGGTCTTCCCCCTGGCACCCTCCTCCAAGAGCACCT
CTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGG
TGACCGTGCCCTCCAGCAGCTTGGGCACCCAGACCTACATCTGCAACGTG
AATCACAAGCCCAGCAACACCAAGGTGGACAAGAGAGTTGGTGAGAGGCC
AGCACAGGGAGGGAGGGTGTCTGCTGGAAGCCAGGCTCAGCGCTCCTGCC
TGGACGCATCCCGGCTATGCAGTCCCAGTCCAGGGCAGCAAGGCAGGCCC
CGTCTGCCTCTTCACCCGGAGGCCTCTGCCCGCCCCACTCATGCTCAGGG
AGAGGGTCTTCTGGCTTTTTCCCCAGGCTCTGGGCAGGCACGGGCTAGGT
GCCCCTAACCCAGGCCCTGCACACAAAGGGGCAGGTGCTGGGCTCAGACC
TGCCAAGAGCCATATCCGGGAGGACCCTGCCCCTGACCTAAGCCCACCCC
AAAGGCCAAACTCTCCACTCCCTCAGCTCGGACACCTTCTCTCCTCCCAG
ATTCCAGTAACTCCCAATCTTCTCTCTGCAGAGCCCAAATCTTGTGACAA
AACTCACACATGCCCACCGTGCCCAGGTAAGCCAGCCCAGGCCTCGCCCT
CCAGCTCAAGGCGGGACAGGTGCCCTAGAGTAGCCTGCATCCAGGGACAG
GCCCCAGCCGGGTGCTGACACGTCCACCTCCATCTCTTCCTCAGCACCTG
AACTCCTGGGGGGACCGTCAGTCTTCCTCTTCCCCCCAAAACCCAAGGAC
ACCCTCATGATCTCCCGGACCCCTGAGGTCACATGCGTGGTGGTGGACGT
GAGCCACGAAGACCCTGAGGTCAAGTTCAACTGGTACGTGGACGGCGTGG
AGGTGCATAATGCCAAGACAAAGCCGCGGGAGGAGCAGTACAACAGCACG
TACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCG
AGAAAACCATCTCCAAAGCCAAAGGTGGGACCCGTGGGGTGCGAGGGCCA
CATGGACAGAGGCCGGCTCGGCCCACCCTCTGCCCTGAGAGTGACCGCTG
TACCAACCTCTGTCCCTACAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTATAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAATGAGCTAGC
GAATTCACCGGTACCAAGCTTAAGTTTAAACCGCTGATCAGCCTCGACTG
TGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGA
AATTGCATCGCATTGTCTGAGTAGGTGTCATTCTATTCTGGGGGGTGGGG
TGGGGCAGGACAGCAAGGGGGAGGATTGGGAAGACAATAGCAGGCATGCT
GGGGATGCGGTGGGCTCTATGGCTTCTGAGGCGGAAAGAACCAGCTGGGG
CTCTAGGGGGTATCCCCACGCGCCCTGTAGCGGCGCATTAAGCGCGGCGG
GTGTGGTGGTTACGCGCAGCGTGACCGCTACACTTGCCAGCGCCTAGCGC
CCGCTCCTTTCGCTTTCTTCCCTTCCTTTCTCGCCACGTTCGCCGGCTTT
CCCCGTCAAGCTCTAAATCGGGGGCTCCCTTTAGGGTTCCGATTTAGTGC
TTTACGGCACCTCGACCCCAAAAAACTTGATTAGGGTGATGGTTCACGTA
GTGGGCCATCGCCCTGATAGACGGTTTTTCGCCCTTTGACGTTGGAGTCC
ACGTTCTTTAATAGTGGACTCTTGTTCCAAACTGGAACAACACTCAACCC

-continued

```
TATCTCGGTCTATTCTTTTGATTTATAAGGGATTTTGCCGATTTCGGCCT
ATTGGTTAAAAAATGAGCTGATTTAACAAAAATTTAACGCGAATTAATTC
TGTGGAATGTGTGTCAGTTAGGGTGTGGAAAGTCCCCAGGCTCCCCAGCA
GGCAGAAGTATGCAAAGCATGCATCTCAATTAGTCAGCAACCAGGTGTGG
AAAGTCCCCAGGCTCCCCAGCAGGCAGAAGTATGCAAAGCATGCATCTCA
ATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTT
TATTTATGCAGAGGCCGAGGCCGCCTCTGCCTCTGAGCTATTCCAGAAGT
AGTGAGGAGGCTTTTTTGGAGGCCTAGGCTTTTGCAAAAAGCTCCCGGGA
GCTTGGATATCCATTTTCGGATCTGATCAAGAGACAGGATGAGGATCGTT
TCGCATGATTGAACAAGATGGATTGCACGCAGGTTCTCCGGCCGCTTGGG
TGGAGAGGCTATTCGGCTATGACTGGGCACAACAGACAATCGGCTGCTCT
GATGCCGCCGTGTTCCGGCTGTCAGCGCAGGGGCGCCCGGTTCTTTTTGT
CAAGACCGACCTGTCCGGTGCCCTGAATGAACTGCAGGACGAGGCAGCGC
GGCTATCGTGGCTGGCCACGACGGGCGTTCCTTGCGCAGCTGTGCTCGAC
GTTGTCACTGAAGCGGGAAGGGACTGGCTGCTATTGGGCGAAGTGCCGGG
GCAGGATCTCCTGTCATCTCACCTTGCTCCTGCCGAGAAAGTATCCATCA
TGGCTGATGCAATGCGGCGGCTGCATACGCTTGATCCGGCTACCTGCCCA
TTCGACCACCAAGCGAAACATCGCATCGAGCGAGCACGTACTCGGATGGA
AGCCGGTCTTGTCGATCAGGATGATCTGGACGAAGAGCATCAGGGGCTCG
CGCCAGCCGAACTGTTCGCCAGGCTCAAGGCGCGCATGCCCGACGGCGAG
GATCTCGTCGTGACCCATGGCGATGCCTGCTTGCCGAATATCATGGTGGA
AAATGGCCGCTTTTCTGGATTCATCGACTGTGGCCGGCTGGGTGTGGCGG
ACCGCTATCAGGACATAGCGTTGGCTACCCGTGATATTGCTGAAGAGCTT
GGCGGCGAATGGGCTGACCGCTTCCTCGTGCTTTACGGTATCGCCGCTCC
CGATTCGCAGCGCATCGCCTTCTATCGCCTTCTTGACGAGTTCTTCTGAG
CGGGACTCTGGGGTTCGGTGCTACGAGATTTCGATTCCACCGCCGCCTTC
TATGAAAGGTTGGGCTTCGGAATCGTTTTCCGGGACGCCGGCTGGATGAT
CCTCCAGCGCGGGGATCTCATGCTGGAGTTCTTCGCCCACCCCAACTTGT
TTATTGCAGCTTATAATGGTTACAAATAAAGCAATAGCATCACAAATTTC
ACAAATAAAGCATTTTTTTCACTGCATTCTAGTTGTGGTTTGTCCAAACT
CATCAATGTATCTTATCATGTCTGTATACCGTCGACCTCTAGCTAGAGCT
TGGCGTAATCATGGTCATAGCTGTTTCCTGTGTGAAATTGTTATCCGCTC
ACAATTCCACACAACATACGAGCCGGAAGCATAAAGTGTAAAGCCTGGGG
TGCCTAATGAGTGAGCTAACTCACATTAATTGCGTTGCGCTCACTGCCC
GCTTTCCAGTCGGGAAACCTGTCGTGCCAGAATTGCATGAAGAATCTGCT
TAGGGTTAGGCGTTTTGCGCTGCTTCGCTAGGTGGTCAATATTGGCCATT
AGCCATATTATTCATTGGTTATATAGCATAAATCAATATTGGCTATTGGC
CATTGCATACGTTGTATCCATATCATAATATGTACATTTATATTGGCTCA
TGTCCAACATTACCGCCATGTTGACATTGATTATTGACTAGTTATTAATA
GTAATCAATTACGGGGTCATTAGTTCATAGCCCATATATGGAGTTCCGCG
TTACATAACTTACGGTAAATGGCCCGCCTGGCTGACCGCCCAACGACCCC
CGCCCATTGACGTCAATAATGACGTATGTTCCCATAGTAACGCCAATAGG
GACTTTCCATTGACGTCAATGGGTGGAGTATTTACGGTAAACTGCCCACT
TGGCAGTACATCAAGTGTATCATATGCCAAGTACGCCCCCTATTGACGTC
AATGACGGTAAATGGCCCGCCTGGCATTATGCCCAGTACATGACCTTATG
GGACTTTCCTACTTGGCAGTACATCTACGTATTAGTCATCGCTATTACCA
TGGTGATGCGGTTTTGGCAGTACATCAATGGGCGTGGATAGCGGTTTGAC
TCACGGGGATTTCCAAGTCTCCACCCCATTGACGTCAATGGGAGTTTGTT
TTGGCACCAAAATCAACGGGACTTTCCAAAATGTCGTAACAACTCCGCCC
CATTGACGCAAATGGGCGGTAGGCGTGTACGGTGGGAGGTCTATATAAGC
AGAGCTCGTTTAGTGAACCGTCAGATCGCCTGGAGACGCCATCCACGCTG
TTTTGACCTCCATAGAAGACACCGGGACCGATCCAGCCTCCGCGGCCGGG
AACGGTGCATTGGAAGCTTGGTACCGGTGAATTCGGCGCGCCAGATCTGC
GGCCGCTAGGAAGAAACTCAAAACATCAAGATTTTAAATACGCTTCTTGG
TCTCCTTGCTATAATTATCTGGGATAAGCATGCTGTTTTCTGTCTGTCCC
TAACATGCCCTGTGATTATCCGCAAACAACACACCCAAGGGCAGAACTTT
GTTACTTAAACACCATCCTGTTTGCTTCTTTCCTCAGGTCAGCCCAAGGC
TGCCCCCTCGGTCACTCTGTTCCCGCCCTCCTCTGAGGAGCTTCAAGCCA
ACAAGGCCACACTGGTGTGTCTCATAAGTGACTTCTACCCGGGAGCCGTG
ACAGTGGCCTGGAAGGCAGATAGCAGCCCCGTCAAGGCGGGAGTGGAGAC
CACCACACCCTCCAAACAAAGCAACAACAAGTACGCGGCCAGCAGCTACC
TGAGCCTGACGCCTGAGCAGTGGAAGTCCCACAGAAGCTACAGCTGCCAG
GTCACGCATGAAGGGAGCACCGTGGAGAAGACAGTGGCCCCTACAGAATG
TTCATAGAGTTAACGGATCGATCCGAGCTCGGTACCAAGCTTAAGTTTAA
ACCGCTGATCAGCCTCGACTGTGCCTTCTAGTTGCCAGCCATCTGTTGTT
TGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGG
GAAGACAATAGCAGGCATGCTGGGGATGCGGTGGGCTCTATGGCTTCTGA
GGCGGAAAGAACCAGCTGCATTAATGAATCGGCCAACGCGCGGGGAGAGG
CGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTA
ATACGGTTATCCACAGAATCAGGGGATAACGCAGGAAAGAACATGTGAGC
AAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCA
AGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTA
ACTATCGTCTTGAGTCCAACCCGGTAAGACACGACTTATCGCCACTGGCA
GCAGCCACTGGTAACAGGATTAGCAGAGCGAGGTATGTAGGCGGTGCTAC
AGAGTTCTTGAAGTGGTGGCCTAACTACGGCTACACTAGAAGAACAGTAT
TTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTT
TGATCTTTTCTACGGGGTCTGACGCTCAGTGGAACGAAAACTCACGTTAA
GGGATTTTGGTCATGAGATTATCAAAAAGGATCTTCACCTAGATCCTTTT
AAATTAAAAATGAAGTTTTAAATCAATCTAAAGTATATATGAGTAAACTT
GGTCTGACAGTTACCAATGCTTAATCAGTGAGGCACCTATCTCAGCGATC
TGTCTATTTCGTTCATCCATAGTTGCCTGACTCCCCGTCGTGTAGATAAC
TACGATACGGGAGGGCTTACCATCTGGCCCCAGTGCTGCAATGATACCGC
GAGACCCACGCTCACCGGCTCCAGATTTATCAGCAATAAACCAGCCAGCC
GGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGT
TACATGATCCCCCATGTTGTGCAAAAAAGCGGTTAGCTCCTTCGGTCCTC
CGATCGTTGTCAGAAGTAAGTTGGCCGCAGTGTTATCACTCATGGTTATG
GCAGCACTGCATAATTCTCTTACTGTCATGCCATCCGTAAGATGCTTTTC
TGTGACTGGTGAGTACTCAACCAAGTCATTCTGAGAATAGTGTATGCGGC
GACCGAGTTGCTCTTGCCCGGCGTCAATACGGGATAATACCGCGCCACAT
AGCAGAACTTTAAAAGTGCTCATCATTGGAAAACGTTCTTCGGGGCGAAA
ACTCTCAAGGATCTTACCGCTGTTGAGATCCAGTTCGATGTAACCCACTC
GTGCACCCAACTGATCTTCAGCATCTTTTACTTTCACCAGCGTTTCTGGG
TGAGCAAAAACAGGAAGGCAAAATGCCGCAAAAAAGGGAATAAGGGCGAC
ACGGAAATGTTGAATACTCA
```

The invention claimed is:

1. An isotonic parenteral composition comprising an antibody able to specifically bind to the attachment glycoprotein (G protein) of a respiratory syncytial virus (RSV) and able to neutralize RSV A and B strains, wherein the antibody is selected from the group consisting of:

a) an antibody comprising a heavy chain CDR1 region of SEQ ID NO:1, a heavy chain CDR2 region of SEQ ID NO:2, and a heavy chain CDR3 region of SEQ ID NO:3, a light chain CDR1 region of SEQ ID NO:13, a light chain CDR2 region of SEQ ID NO:14, and a light chain CDR3 region of SEQ ID NO:15, b) an antibody comprising a heavy chain CDR1 region of SEQ ID NO:4, a heavy chain CDR2 region of SEQ ID NO:5, and a heavy chain CDR3 region of SEQ ID NO:6, a light chain CDR1 region of SEQ ID NO:16, a light chain CDR2 region of SEQ ID NO:17, and a light chain CDR3 region of SEQ ID NO:18, c) an antibody comprising a heavy chain CDR1 region of SEQ ID NO:7, a heavy chain CDR2 region of SEQ ID NO:8, and a heavy chain CDR3 region of SEQ ID NO:9, a light chain CDR1 region of SEQ ID NO:19, a light chain CDR2 region of SEQ ID NO:20, and a light chain CDR3 region of SEQ ID NO: 21, d) an antibody comprising a heavy chain CDR1 region of SEQ ID NO:10, a heavy chain CDR2 region of SEQ ID NO:11, and a heavy chain CDR3 region of SEQ ID NO:12, a light chain CDR1 region of SEQ ID NO:22, a light chain CDR2 region of SEQ ID NO:23, and a light chain CDR3 region of SEQ ID NO:24, e) an antibody comprising a heavy chain CDR1 region of SEQ ID NO:25, a heavy chain CDR2 region of SEQ ID NO:26, and a heavy chain CDR3 region of SEQ ID NO:27, a light chain CDR1 region of SEQ ID NO:28, a light chain CDR2 region of SEQ ID NO:29, and a light chain CDR3 region of SEQ ID NO:30; and f) an antibody comprising a heavy chain CDR1 region of SEQ ID NO:31, a heavy chain CDR2 region of SEQ ID NO:32, and a heavy chain CDR3 region of SEQ ID NO:33, a light chain CDR1 region of SEQ ID NO:34, a light chain CDR2 region of SEQ ID NO:35, and a light chain CDR3 region of SEQ ID NO:36; and at least one pharmaceutically acceptable excipient, wherein the at least one pharmaceutically acceptable excipient is selected from the group consisting of a buffer, an antioxidant, and mixtures thereof; and wherein the composition comprises at least one therapeutic agent and/or detectable agent bonded thereto; or wherein the antibody is lyophilized.

2. The antibody of claim 1, wherein the antibody is a human antibody.

3. An isotonic parenteral composition comprising an antigen-binding fragment able to specifically bind to the attachment glycoprotein (G protein) of a respiratory syncytial virus (RSV) and able to neutralize RSV A and B strains, wherein the antigen-binding fragment binds to an epitope within the central conserved domain of the RSV G protein, wherein the antigen-binding fragment comprises a heavy chain CDR1 region of SEQ ID NO:1, a heavy chain CDR2 region of SEQ ID NO:2, and a heavy chain CDR3 region of SEQ ID NO:3, a light chain CDR1 region of SEQ ID NO:13, a light chain CDR2 region of SEQ ID NO:14, and a light chain CDR3 region of SEQ ID NO:15; and at least one pharmaceutically acceptable excipient, wherein the at least one pharmaceutically acceptable excipient is selected from the group consisting of a buffer, an antioxidant, and mixtures thereof; and wherein the antigen-binding fragment further comprises at least one therapeutic agent and/or detectable agent bonded thereto; or wherein the antigen-binding fragment is lyophilized.

4. An isotonic parenteral composition comprising a functional variant of an antibody that is able to specifically bind to the attachment glycoprotein (G protein) of a respiratory syncytial virus (RSV) and able to neutralize RSV A and B strains, wherein the functional variant binds to an epitope within the central conserved domain of the RSV G protein, wherein the functional variant comprises a heavy chain CDR1 region of SEQ ID NO:1, a heavy chain CDR2 region of SEQ ID NO:2, and a heavy chain CDR3 region of SEQ ID NO:3, a light chain CDR1 region of SEQ ID NO:13, a light chain CDR2 region of SEQ ID NO:14, and a light chain CDR3 region of SEQ ID NO:15; and at least one pharmaceutically acceptable excipient, wherein the at least one pharmaceutically acceptable excipient is selected from the group consisting of a buffer, an antioxidant, and mixtures thereof; and wherein the functional variant further comprises at least one therapeutic agent and/or detectable agent bonded thereto; or wherein the functional variant is lyophilized.

5. A method of inhibiting RSV in a subject, the method comprising:

administering to the subject a therapeutically effective amount of the antibody of claim 2.

6. A kit comprising the isotonic parenteral composition according to claim 1.

7. A method of detecting RSV infection, the method comprising:

assaying the level of RSV antigen in a sample using the antibody of claim 2; and comparing the assayed level of RSV antigen with a control level, wherein an increase in the assayed level of RSV antigen compared to the control level is indicative of RSV infection.

8. A method of detecting RSV infection, the method comprising:

assaying the level of RSV antigen in a sample with the functional variant of claim 6, and comparing the assayed level of RSV antigen with a control level, wherein an increase in the assayed level of RSV antigen compared to the control level is indicative of RSV infection.

* * * * *

SEQUENCE LISTING

```
<160> NUMBER OF SEQ ID NOS: 151

<210> SEQ ID NO 1
<211> LENGTH: 5
<212> TYPE: PRT
<213> ORGANISM: Artificial Sequence
<220> FEATURE:
<223> OTHER INFORMATION: CB058.1 HCDR1

<400> SEQUENCE: 1

Ser Tyr Ala Met Ser
1               5


<210> SEQ ID NO 2
<211> LENGTH: 17
<212> TYPE: PRT
<213> ORGANISM: Artificial Sequence
```

<220> FEATURE:
<223> OTHER INFORMATION: CB058.1 HCDR2

<400> SEQUENCE: 2

Ala Ile Arg Gly Ser Val Asp Asn Thr Tyr Tyr Ala Asp Ser Val Lys
1 5 10 15

Gly

<210> SEQ ID NO 3
<211> LENGTH: 17
<212> TYPE: PRT
<213> ORGANISM: Artificial Sequence
<220> FEATURE:
<223> OTHER INFORMATION: CB058.1 HCDR3

<400> SEQUENCE: 3

Asp Pro Ala Leu Tyr Cys Ser Gly Glu Thr Cys Phe Ser Asp Leu Thr
1 5 10 15

Asp

<210> SEQ ID NO 4
<211> LENGTH: 5
<212> TYPE: PRT
<213> ORGANISM: Artificial Sequence
<220> FEATURE:
<223> OTHER INFORMATION: CB048.3 HCDR1

<400> SEQUENCE: 4

Asn His Gly Met His
1 5

<210> SEQ ID NO 5
<211> LENGTH: 17
<212> TYPE: PRT
<213> ORGANISM: Artificial Sequence
<220> FEATURE:
<223> OTHER INFORMATION: CB048.3 HCDR2

<400> SEQUENCE: 5

Val Ile Ser Tyr Asp Gly Asn Lys Lys Tyr Tyr Ala Asp Ser Val Lys
1 5 10 15

Gly

<210> SEQ ID NO 6
<211> LENGTH: 16
<212> TYPE: PRT
<213> ORGANISM: Artificial Sequence
<220> FEATURE:
<223> OTHER INFORMATION: CB048.3 HCDR3

<400> SEQUENCE: 6

Thr Thr Phe Tyr Phe Asp Asp Ser Asn Tyr Tyr Glu Tyr Leu Asp Tyr
1 5 10 15

<210> SEQ ID NO 7
<211> LENGTH: 5
<212> TYPE: PRT
<213> ORGANISM: Artificial Sequence
<220> FEATURE:
<223> OTHER INFORMATION: CB010.7 HCDR1

<400> SEQUENCE: 7

Thr His Gly Met His
1 5

<210> SEQ ID NO 8
<211> LENGTH: 17
<212> TYPE: PRT
<213> ORGANISM: Artificial Sequence
<220> FEATURE:
<223> OTHER INFORMATION: CB010.7 HCDR2

<400> SEQUENCE: 8

Val Met Ser Tyr Asp Gly Thr Lys Lys Tyr His Ala Asp Ser Val Lys
1 5 10 15

Gly

<210> SEQ ID NO 9
<211> LENGTH: 24
<212> TYPE: PRT
<213> ORGANISM: Artificial Sequence
<220> FEATURE:
<223> OTHER INFORMATION: CB010.7 HCDR3

<400> SEQUENCE: 9

Val Gly Glu Leu Arg Ser Phe Asp Trp Leu Leu Ala Asp Gly Thr Ala
1 5 10 15

Tyr Tyr Tyr Tyr Gly Met Asp Val
20

<210> SEQ ID NO 10
<211> LENGTH: 5
<212> TYPE: PRT
<213> ORGANISM: Artificial Sequence
<220> FEATURE:
<223> OTHER INFORMATION: CB003.1 HCDR1

<400> SEQUENCE: 10

Thr Tyr Tyr Ile His
1 5

<210> SEQ ID NO 11
<211> LENGTH: 17
<212> TYPE: PRT
<213> ORGANISM: Artificial Sequence
<220> FEATURE:
<223> OTHER INFORMATION: CB003.1 HCDR2

<400> SEQUENCE: 11

Met Ile Asn Thr Gly Ser Gly Val Thr Ser Tyr Ala Gln Lys Phe Gln
1 5 10 15

Gly

<210> SEQ ID NO 12
<211> LENGTH: 11
<212> TYPE: PRT
<213> ORGANISM: Artificial Sequence
<220> FEATURE:
<223> OTHER INFORMATION: CD003.1 HCDR3

<400> SEQUENCE: 12

Met Tyr Ser Gly Ser Trp Tyr Pro Phe Asp Tyr
1 5 10

<210> SEQ ID NO 13
<211> LENGTH: 11
<212> TYPE: PRT
<213> ORGANISM: Artificial Sequence
<220> FEATURE:
<223> OTHER INFORMATION: CB058.1 LCDR1

<400> SEQUENCE: 13

Arg Ala Ser Gln Gly Ile Asn Asn Tyr Leu Ala
1 5 10

<210> SEQ ID NO 14
<211> LENGTH: 7
<212> TYPE: PRT
<213> ORGANISM: Artificial Sequence
<220> FEATURE:
<223> OTHER INFORMATION: CB058.1 LCDR2

<400> SEQUENCE: 14

Ala Ala Ser Thr Leu Pro Ser
1 5

<210> SEQ ID NO 15
<211> LENGTH: 7
<212> TYPE: PRT
<213> ORGANISM: Artificial Sequence
<220> FEATURE:
<223> OTHER INFORMATION: CB058.1 LCDR3

<400> SEQUENCE: 15

Gln His Tyr Ile Arg Tyr Pro
1 5

<210> SEQ ID NO 16
<211> LENGTH: 11
<212> TYPE: PRT
<213> ORGANISM: Artificial Sequence
<220> FEATURE:
<223> OTHER INFORMATION: CB048.3 LCDR1

<400> SEQUENCE: 16

Arg Ala Ser Gln Gly Ile Arg Ser Tyr Leu Ala
1 5 10

<210> SEQ ID NO 17
<211> LENGTH: 7
<212> TYPE: PRT
<213> ORGANISM: Artificial Sequence
<220> FEATURE:
<223> OTHER INFORMATION: CB048.3 LCDR2

<400> SEQUENCE: 17

Ala Ala Ser Thr Leu Gln Ser
1 5

<210> SEQ ID NO 18
<211> LENGTH: 8
<212> TYPE: PRT
<213> ORGANISM: Artificial Sequence
<220> FEATURE:
<223> OTHER INFORMATION: CB048.3 LCDR3

<400> SEQUENCE: 18

Gln Gln Leu Asn Thr Ser Pro Pro
1 5

<210> SEQ ID NO 19
<211> LENGTH: 17
<212> TYPE: PRT
<213> ORGANISM: Artificial Sequence
<220> FEATURE:
<223> OTHER INFORMATION: CB010.7 LCDR1

<400> SEQUENCE: 19

Lys Ser Ser Gln Ser Val Leu Tyr Ser Ser Asn Asn Lys Asn Tyr Leu
1 5 10 15

Ala

<210> SEQ ID NO 20
<211> LENGTH: 7
<212> TYPE: PRT
<213> ORGANISM: Artificial Sequence
<220> FEATURE:
<223> OTHER INFORMATION: CB010.7 LCDR2

<400> SEQUENCE: 20

Trp Ala Ser Thr Arg Glu Phe
1 5

<210> SEQ ID NO 21
<211> LENGTH: 7
<212> TYPE: PRT
<213> ORGANISM: Artificial Sequence
<220> FEATURE:
<223> OTHER INFORMATION: CB010.7 LCDR3

<400> SEQUENCE: 21

His Gln Tyr Tyr Ser Ile Pro
1 5

<210> SEQ ID NO 22
<211> LENGTH: 12
<212> TYPE: PRT
<213> ORGANISM: Artificial Sequence
<220> FEATURE:
<223> OTHER INFORMATION: CB003.1 LCDR1

<400> SEQUENCE: 22

Arg Ala Ser Gln Asn Ile Asn Gly Asn Tyr Leu Ala
1 5 10

<210> SEQ ID NO 23
<211> LENGTH: 7
<212> TYPE: PRT
<213> ORGANISM: Artificial Sequence
<220> FEATURE:
<223> OTHER INFORMATION: CB003.1 LCDR2

<400> SEQUENCE: 23

Glu Ala Ser Ser Arg Ala Thr
1 5

<210> SEQ ID NO 24
<211> LENGTH: 8
<212> TYPE: PRT
<213> ORGANISM: Artificial Sequence
<220> FEATURE:
<223> OTHER INFORMATION: CB003.1 LCDR3

<400> SEQUENCE: 24

Gln Gln Tyr Gly Thr Ser Pro Phe
1 5

<210> SEQ ID NO 25
<211> LENGTH: 5
<212> TYPE: PRT
<213> ORGANISM: Artificial Sequence
<220> FEATURE:
<223> OTHER INFORMATION: CB002.1 HCDR1

<400> SEQUENCE: 25

Ser Tyr Phe Trp Asn
1 5

<210> SEQ ID NO 26
<211> LENGTH: 16
<212> TYPE: PRT
<213> ORGANISM: Artificial Sequence
<220> FEATURE:
<223> OTHER INFORMATION: CB002.1 HCDR2

<400> SEQUENCE: 26

Tyr Ile Tyr Gly Ser Gly Ser Ala Asp Tyr Asn Pro Ser Leu Lys Ser
1 5 10 15

<210> SEQ ID NO 27
<211> LENGTH: 18
<212> TYPE: PRT
<213> ORGANISM: Artificial Sequence
<220> FEATURE:
<223> OTHER INFORMATION: CB002.1 HCDR3

<400> SEQUENCE: 27

Ser Gly Phe Cys Thr Asn Asp Ala Cys Tyr Arg Arg Gly Ser Trp Phe
1 5 10 15

Asp Pro

<210> SEQ ID NO 28
<211> LENGTH: 11
<212> TYPE: PRT
<213> ORGANISM: Artificial Sequence
<220> FEATURE:
<223> OTHER INFORMATION: CB002.1 LCDR1

<400> SEQUENCE: 28

Arg Ala Ser Gln Ser Ile Asp Asn Tyr Leu Asn
1 5 10

<210> SEQ ID NO 29
<211> LENGTH: 7
<212> TYPE: PRT
<213> ORGANISM: Artificial Sequence
<220> FEATURE:
<223> OTHER INFORMATION: CB002.1 LCDR2

<400> SEQUENCE: 29

Ala Ala Ser Ser Leu Gln Ser
1 5

<210> SEQ ID NO 30
<211> LENGTH: 8
<212> TYPE: PRT
<213> ORGANISM: Artificial Sequence
<220> FEATURE:
<223> OTHER INFORMATION: CB002.1 LCDR3

<400> SEQUENCE: 30

Gln Gln Ser Tyr Ser Thr Leu Thr
1 5

<210> SEQ ID NO 31
<211> LENGTH: 5
<212> TYPE: PRT
<213> ORGANISM: Artificial Sequence
<220> FEATURE:

<223> OTHER INFORMATION: CB028.2 HCDR1

<400> SEQUENCE: 31

```
Thr Tyr Gly Ile Thr
1               5
```

<210> SEQ ID NO 32
<211> LENGTH: 17
<212> TYPE: PRT
<213> ORGANISM: Artificial Sequence
<220> FEATURE:
<223> OTHER INFORMATION: CB028.2 HCDR2

<400> SEQUENCE: 32

```
Trp Ile Ser Gly Asp Ser Asp Asn Thr Asn Tyr Ala Gln Asn Leu Gln
1               5                   10                  15

Gly
```

<210> SEQ ID NO 33
<211> LENGTH: 23
<212> TYPE: PRT
<213> ORGANISM: Artificial Sequence
<220> FEATURE:
<223> OTHER INFORMATION: CB028.2 HCDR3

<400> SEQUENCE: 33

```
Ala Leu Ala Lys Trp Tyr Cys Ser Ser Ser Ser Cys Phe Cys Gly Gly
1               5                   10                  15

Gly Ser Cys Tyr Ser Asp Tyr
            20
```

<210> SEQ ID NO 34
<211> LENGTH: 11
<212> TYPE: PRT
<213> ORGANISM: Artificial Sequence
<220> FEATURE:
<223> OTHER INFORMATION: CB028.2 LCDR1

<400> SEQUENCE: 34

```
Arg Ala Ser Gln Gly Met Ser Asn Tyr Leu Asn
1               5                   10
```

<210> SEQ ID NO 35
<211> LENGTH: 7
<212> TYPE: PRT
<213> ORGANISM: Artificial Sequence
<220> FEATURE:
<223> OTHER INFORMATION: CB028.2 LCDR2

<400> SEQUENCE: 35

```
Ala Ala Ser Thr Leu Gln Ser
1               5
```

<210> SEQ ID NO 36
<211> LENGTH: 7
<212> TYPE: PRT
<213> ORGANISM: Artificial Sequence
<220> FEATURE:
<223> OTHER INFORMATION: CB028.2 LCDR3

<400> SEQUENCE: 36

```
Gln Gln Ser Phe Ser Thr Pro
1               5
```

<210> SEQ ID NO 37

```
<211> LENGTH: 126
<212> TYPE: PRT
<213> ORGANISM: Artificial Sequence
<220> FEATURE:
<223> OTHER INFORMATION: CB058.1 VH

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Arg Gly Ser Val Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Pro Ala Leu Tyr Cys Ser Gly Glu Thr Cys Phe Ser Asp
            100                 105                 110

Leu Thr Asp Trp Gly Gln Gly Thr Leu Val Thr Val Ser Ser
        115                 120                 125


<210> SEQ ID NO 38
<211> LENGTH: 107
<212> TYPE: PRT
<213> ORGANISM: Artificial Sequence
<220> FEATURE:
<223> OTHER INFORMATION: CB058.1 VK

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Ala Pro Lys Ser Leu Ile
        35                  40                  45

Tyr Ala Ala Ser Thr Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Phe Cys Gln His Tyr Ile Arg Tyr Pro His
                85                  90                  95

Thr Phe Gly Gln Gly Thr Lys Leu Glu Ile Lys
            100                 105


<210> SEQ ID NO 39
<211> LENGTH: 125
<212> TYPE: PRT
<213> ORGANISM: Artificial Sequence
<220> FEATURE:
<223> OTHER INFORMATION: CB048.3 VH

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn His
            20                  25                  30
```

```
Gly Met His Trp Val Arg Gln Ala Pro Gly Lys Gly Leu Glu Trp Val
        35                  40                  45

Ala Val Ile Ser Tyr Asp Gly Asn Lys Lys Tyr Tyr Ala Asp Ser Val
    50                  55                  60

Lys Gly Arg Phe Thr Val Ser Arg Asp Asn Ser Lys Asn Thr Leu Ser
65                  70                  75                  80

Leu Gln Met Asp Ser Leu Arg Ala Glu Asp Thr Ala Ile Tyr Tyr Cys
                85                  90                  95

Ala Lys Thr Thr Phe Tyr Phe Asp Asp Ser Asn Tyr Tyr Glu Tyr Leu
            100                 105                 110

Asp Tyr Trp Gly Gln Gly Thr Leu Val Thr Val Ser Ser
        115                 120                 125


<210> SEQ ID NO 40
<211> LENGTH: 108
<212> TYPE: PRT
<213> ORGANISM: Artificial Sequence
<220> FEATURE:
<223> OTHER INFORMATION: CB048.3 VK

<400> SEQUENCE: 40

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Arg Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Ser Ala Thr Tyr Tyr Cys Gln Gln Leu Asn Thr Ser Pro Pro
                85                  90                  95

Tyr Thr Phe Gly Gln Gly Thr Lys Leu Glu Ile Lys
            100                 105


<210> SEQ ID NO 41
<211> LENGTH: 133
<212> TYPE: PRT
<213> ORGANISM: Artificial Sequence
<220> FEATURE:
<223> OTHER INFORMATION: CB010.7 VH

<400> SEQUENCE: 41

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Thr His
            20                  25                  30

Gly Met His Trp Val Arg Gln Ala Pro Gly Lys Gly Leu Glu Trp Val
        35                  40                  45

Ala Val Met Ser Tyr Asp Gly Thr Lys Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Ile Tyr Tyr Cys
                85                  90                  95

Ala Lys Val Gly Glu Leu Arg Ser Phe Asp Trp Leu Leu Ala Asp Gly
            100                 105                 110
```

```
Thr Ala Tyr Tyr Tyr Tyr Gly Met Asp Val Trp Gly Gln Gly Thr Thr
        115                 120                 125

Val Thr Val Ser Ser
    130


<210> SEQ ID NO 42
<211> LENGTH: 113
<212> TYPE: PRT
<213> ORGANISM: Artificial Sequence
<220> FEATURE:
<223> OTHER INFORMATION: CB010.7 VK

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Phe Gln Gln Lys Pro Gly Gln
        35                  40                  45

Pro Pro Arg Leu Leu Ile Asn Trp Ala Ser Thr Arg Glu Phe Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys His Gln
                85                  90                  95

Tyr Tyr Ser Ile Pro Leu Thr Phe Gly Gly Gly Thr Lys Val Glu Ile
            100                 105                 110

Lys


<210> SEQ ID NO 43
<211> LENGTH: 120
<212> TYPE: PRT
<213> ORGANISM: Artificial Sequence
<220> FEATURE:
<223> OTHER INFORMATION: CB003.1 VH

<400> SEQUENCE: 43

Gln Val Gln Leu Val Gln Ser Gly Pro Glu Leu Arg Lys Pro Gly Ala
1               5                   10                  15

Ser Val Thr Val Ser Cys Lys Ala Ser Gly Tyr Thr Phe Thr Thr Tyr
            20                  25                  30

Tyr Ile His Trp Val Arg Gln Ala Pro Gly Gly Gly Leu Asp Trp Met
        35                  40                  45

Gly Met Ile Asn Thr Gly Ser Gly Val Thr Ser Tyr Ala Gln Lys Phe
    50                  55                  60

Gln Gly Arg Val Ala Met Thr Arg Asp Thr Ser Thr Ser Thr Val Phe
65                  70                  75                  80

Met Glu Leu Ser Ser Leu Arg Phe Glu Asp Thr Ala Leu Tyr Tyr Cys
                85                  90                  95

Ala Arg Met Tyr Ser Gly Ser Trp Tyr Pro Phe Asp Tyr Trp Gly Gln
            100                 105                 110

Gly Ala Leu Val Thr Val Ser Ser
        115                 120


<210> SEQ ID NO 44
<211> LENGTH: 109
<212> TYPE: PRT
<213> ORGANISM: Artificial Sequence
```

```
<220> FEATURE:
<223> OTHER INFORMATION: CB003.1 VK

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Ile Asn Gly Asn
            20                  25                  30

Tyr Leu Ala Trp Tyr Gln Gln Lys Pro Gly Leu Ala Pro Arg Leu Leu
        35                  40                  45

Ile Tyr Glu Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Gly Val Tyr Tyr Cys Gln Gln Tyr Gly Thr Ser Pro
                85                  90                  95

Phe Phe Thr Phe Gly Pro Gly Thr Lys Val Asp Ile Lys
            100                 105


<210> SEQ ID NO 45
<211> LENGTH: 132
<212> TYPE: PRT
<213> ORGANISM: Artificial Sequence
<220> FEATURE:
<223> OTHER INFORMATION: CB028.2 VH

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Thr Trp Val Arg Gln Ala Pro Gly Gln Gly Leu Glu Trp Met
        35                  40                  45

Gly Trp Ile Ser Gly Asp Ser Asp Asn Thr Asn Tyr Ala Gln Asn Leu
    50                  55                  60

Gln Gly Arg Val Thr Leu Thr Thr Asp Ile Ser Thr Arg Thr Ala Tyr
65                  70                  75                  80

Met Glu Leu Arg Ser Leu Lys Pro Asp Asp Thr Ala Met Tyr Tyr Cys
                85                  90                  95

Ala Arg Ala Leu Ala Lys Trp Tyr Cys Ser Ser Ser Ser Cys Phe Cys
            100                 105                 110

Gly Gly Gly Ser Cys Tyr Ser Asp Tyr Trp Gly Gln Gly Thr Leu Val
        115                 120                 125

Thr Val Ser Ser
    130


<210> SEQ ID NO 46
<211> LENGTH: 107
<212> TYPE: PRT
<213> ORGANISM: Artificial Sequence
<220> FEATURE:
<223> OTHER INFORMATION: CB028.2 VK

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Met Ser Asn Tyr
            20                  25                  30
```

```
Leu Asn Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Phe Cys Gln Gln Ser Phe Ser Thr Pro Leu
                85                  90                  95

Thr Phe Gly Gly Gly Thr Lys Val Glu Ile Lys
            100                 105


<210> SEQ ID NO 47
<211> LENGTH: 126
<212> TYPE: PRT
<213> ORGANISM: Artificial Sequence
<220> FEATURE:
<223> OTHER INFORMATION: CB002.1 VH

<400> SEQUENCE: 47

Gln Val Gln Leu Gln Glu Ser Gly Pro Arg Leu Val Lys Pro Ser Glu
1               5                   10                  15

Thr Leu Ser Leu Thr Cys Thr Val Ser Gly Gly Ser Thr Ser Ser Tyr
            20                  25                  30

Phe Trp Asn Trp Ile Arg Gln Pro Pro Gly Lys Gly Leu Glu Trp Ile
        35                  40                  45

Gly Tyr Ile Tyr Gly Ser Gly Ser Ala Asp Tyr Asn Pro Ser Leu Lys
    50                  55                  60

Ser Arg Val Thr Ile Ser Ile Asp Thr Ser Lys Thr Gln Phe Ser Leu
65                  70                  75                  80

Lys Leu Thr Ser Val Thr Ala Ala Asp Thr Ala Val Tyr Tyr Cys Ala
                85                  90                  95

Arg Ser Gly Phe Cys Thr Asn Asp Ala Cys Tyr Arg Arg Gly Ser Trp
            100                 105                 110

Phe Asp Pro Trp Gly Gln Gly Thr Leu Val Thr Val Ser Ser
        115                 120                 125


<210> SEQ ID NO 48
<211> LENGTH: 108
<212> TYPE: PRT
<213> ORGANISM: Artificial Sequence
<220> FEATURE:
<223> OTHER INFORMATION: CB002.1 VK

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Val Ser Ser Leu His Pro
65                  70                  75                  80

Glu Asp Phe Ala Thr Tyr Tyr Cys Gln Gln Ser Tyr Ser Thr Leu Thr
                85                  90                  95

Trp Thr Phe Gly Gln Gly Thr Lys Val Glu Ile Lys
            100                 105
```

<210> SEQ ID NO 49
<211> LENGTH: 259
<212> TYPE: PRT
<213> ORGANISM: Artificial Sequence
<220> FEATURE:
<223> OTHER INFORMATION: RSV G A/Long (P20895)

<400> SEQUENCE: 49

```
Ala Asn His Lys Val Thr Leu Thr Thr Ala Ile Ile Gln Asp Ala Thr
1               5                   10                  15

Ser Gln Ile Lys Asn Thr Thr Pro Thr Tyr Leu Thr Gln Asp Pro Gln
            20                  25                  30

Leu Gly Ile Ser Phe Ser Asn Leu Ser Glu Ile Thr Ser Gln Thr Thr
        35                  40                  45

Thr Ile Leu Ala Ser Thr Thr Pro Gly Val Lys Ser Asn Leu Gln Pro
    50                  55                  60

Thr Thr Val Lys Thr Lys Asn Thr Thr Thr Thr Gln Thr Gln Pro Ser
65                  70                  75                  80

Lys Pro Thr Thr Lys Gln Arg Gln Asn Lys Pro Pro Asn Lys Pro Asn
                85                  90                  95

Asn Asp Phe His Phe Glu Val Phe Asn Phe Val Pro Cys Ser Ile Cys
            100                 105                 110

Ser Asn Asn Pro Thr Cys Trp Ala Ile Cys Lys Arg Ile Pro Asn Lys
        115                 120                 125

Lys Pro Gly Lys Lys Thr Thr Thr Lys Pro Thr Lys Lys Pro Thr Phe
    130                 135                 140

Lys Thr Thr Lys Lys Asp Leu Lys Pro Gln Thr Thr Lys Pro Lys Glu
145                 150                 155                 160

Val Pro Thr Thr Lys Pro Thr Glu Glu Pro Thr Ile Asn Thr Thr Lys
                165                 170                 175

Thr Asn Ile Thr Thr Thr Leu Leu Thr Asn Asn Thr Thr Gly Asn Pro
            180                 185                 190

Lys Leu Thr Ser Gln Met Glu Thr Phe His Ser Thr Ser Ser Glu Gly
        195                 200                 205

Asn Leu Ser Pro Ser Gln Val Ser Thr Thr Ser Glu His Pro Ser Gln
    210                 215                 220

Pro Ser Ser Pro Pro Asn Thr Thr Arg Gln Gln Ala Tyr Val Glu Gln
225                 230                 235                 240

Lys Leu Ile Ser Glu Glu Asp Leu Asn Ser Ala Val Asp His His His
                245                 250                 255

His His His
```

<210> SEQ ID NO 50
<211> LENGTH: 260
<212> TYPE: PRT
<213> ORGANISM: Artificial Sequence
<220> FEATURE:
<223> OTHER INFORMATION: RSV G B/B1 (NP_056862)

<400> SEQUENCE: 50

```
Ala Asn His Lys Val Thr Leu Thr Thr Val Thr Val Gln Thr Ile Lys
1               5                   10                  15

Asn His Thr Glu Lys Asn Ile Thr Thr Tyr Leu Thr Gln Val Pro Pro
            20                  25                  30

Glu Arg Val Ser Ser Ser Lys Gln Pro Thr Thr Thr Ser Pro Ile His
        35                  40                  45
```

```
Thr Asn Ser Ala Thr Thr Ser Pro Asn Thr Lys Ser Glu Thr His His
    50                  55                  60

Thr Thr Ala Gln Thr Lys Gly Arg Thr Thr Thr Ser Thr Gln Thr Asn
65                  70                  75                  80

Lys Pro Ser Thr Lys Pro Arg Leu Lys Asn Pro Pro Lys Lys Pro Lys
                85                  90                  95

Asp Asp Tyr His Phe Glu Val Phe Asn Phe Val Pro Cys Ser Ile Cys
            100                 105                 110

Gly Asn Asn Gln Leu Cys Lys Ser Ile Cys Lys Thr Ile Pro Ser Asn
        115                 120                 125

Lys Pro Lys Lys Lys Pro Thr Ile Lys Pro Thr Asn Lys Pro Thr Thr
    130                 135                 140

Lys Thr Thr Asn Lys Arg Asp Pro Lys Thr Pro Ala Lys Thr Thr Lys
145                 150                 155                 160

Lys Glu Thr Thr Thr Asn Pro Thr Lys Lys Pro Thr Leu Thr Thr Thr
                165                 170                 175

Glu Arg Asp Thr Ser Thr Ser Gln Ser Thr Val Leu Asp Thr Thr Thr
            180                 185                 190

Leu Glu His Thr Ile Gln Gln Gln Ser Leu His Ser Thr Thr Pro Glu
        195                 200                 205

Asn Thr Pro Asn Ser Thr Gln Thr Pro Thr Ala Ser Glu Pro Ser Thr
    210                 215                 220

Ser Asn Ser Thr Gln Asn Thr Gln Ser His Ala Gln Ala Tyr Val Glu
225                 230                 235                 240

Gln Lys Leu Ile Ser Glu Glu Asp Leu Asn Ser Ala Val Asp His His
                245                 250                 255

His His His His
            260
```

<210> SEQ ID NO 51
<211> LENGTH: 24
<212> TYPE: DNA
<213> ORGANISM: Artificial Sequence
<220> FEATURE:
<223> OTHER INFORMATION: CB-5?LVH1a

<400> SEQUENCE: 51
atggactgga cctggaggtt cctc 24

<210> SEQ ID NO 52
<211> LENGTH: 24
<212> TYPE: DNA
<213> ORGANISM: Artificial Sequence
<220> FEATURE:
<223> OTHER INFORMATION: CB-5?LVH1b

<400> SEQUENCE: 52
atggactgga cctggaggat cctc 24

<210> SEQ ID NO 53
<211> LENGTH: 24
<212> TYPE: DNA
<213> ORGANISM: Artificial Sequence
<220> FEATURE:
<223> OTHER INFORMATION: CB-5?LVH1c

<400> SEQUENCE: 53
atggactgga cctggagggt cttc 24

<210> SEQ ID NO 54
<211> LENGTH: 22
<212> TYPE: DNA
<213> ORGANISM: Artificial Sequence
<220> FEATURE:
<223> OTHER INFORMATION: CB-5?LVH1d

<400> SEQUENCE: 54
atggactgga cctggagcat cc 22

<210> SEQ ID NO 55
<211> LENGTH: 26
<212> TYPE: DNA
<213> ORGANISM: Artificial Sequence
<220> FEATURE:
<223> OTHER INFORMATION: CB-5?LVH2

<400> SEQUENCE: 55
ggacatactt tgttccacgc tcctgc 26

<210> SEQ ID NO 56
<211> LENGTH: 23
<212> TYPE: DNA
<213> ORGANISM: Artificial Sequence
<220> FEATURE:
<223> OTHER INFORMATION: CB-5?LVH3a

<400> SEQUENCE: 56
aggtgtccag tgtcaggtgc agc 23

<210> SEQ ID NO 57
<211> LENGTH: 23
<212> TYPE: DNA
<213> ORGANISM: Artificial Sequence
<220> FEATURE:
<223> OTHER INFORMATION: CB-5?LVH3b

<400> SEQUENCE: 57
aggtgtccag tgtgaggtgc agc 23

<210> SEQ ID NO 58
<211> LENGTH: 23
<212> TYPE: DNA
<213> ORGANISM: Artificial Sequence
<220> FEATURE:
<223> OTHER INFORMATION: CB-5?LVH3c

<400> SEQUENCE: 58
aggtgtccag tgtcaggtac agc 23

<210> SEQ ID NO 59
<211> LENGTH: 21
<212> TYPE: DNA
<213> ORGANISM: Artificial Sequence
<220> FEATURE:
<223> OTHER INFORMATION: CB-5?LVH4

<400> SEQUENCE: 59
gcagctccca gatgggtcct g 21

<210> SEQ ID NO 60
<211> LENGTH: 21
<212> TYPE: DNA
<213> ORGANISM: Artificial Sequence
<220> FEATURE:
<223> OTHER INFORMATION: CB-5?LVH5

<400> SEQUENCE: 60
tcaaccgcca tcctcgccct c 21

<210> SEQ ID NO 61
<211> LENGTH: 26
<212> TYPE: DNA
<213> ORGANISM: Artificial Sequence
<220> FEATURE:
<223> OTHER INFORMATION: CB-5?LVH6

<400> SEQUENCE: 61
gtctgtctcc ttcctcatct tcctgc 26

<210> SEQ ID NO 62
<211> LENGTH: 23
<212> TYPE: DNA
<213> ORGANISM: Artificial Sequence
<220> FEATURE:
<223> OTHER INFORMATION: 3?CgCH1

<400> SEQUENCE: 62
ggaaggtgtg cacgccgctg gtc 23

<210> SEQ ID NO 63
<211> LENGTH: 21
<212> TYPE: DNA
<213> ORGANISM: Artificial Sequence
<220> FEATURE:
<223> OTHER INFORMATION: CB-5?LVk1a

<400> SEQUENCE: 63
atgagggtcc ccgctcagct c 21

<210> SEQ ID NO 64
<211> LENGTH: 21
<212> TYPE: DNA
<213> ORGANISM: Artificial Sequence
<220> FEATURE:
<223> OTHER INFORMATION: CB-5?LVk1b

<400> SEQUENCE: 64
atgagggtcc ctgctcagct c 21

<210> SEQ ID NO 65
<211> LENGTH: 21
<212> TYPE: DNA
<213> ORGANISM: Artificial Sequence
<220> FEATURE:
<223> OTHER INFORMATION: CB-5?LVk1c

<400> SEQUENCE: 65
atgagagtcc tcgctcagct c 21

<210> SEQ ID NO 66
<211> LENGTH: 20
<212> TYPE: DNA
<213> ORGANISM: Artificial Sequence
<220> FEATURE:
<223> OTHER INFORMATION: CB-5?LVk2

<400> SEQUENCE: 66
tggggctgct aatgctctgg 20

<210> SEQ ID NO 67

<211> LENGTH: 23
<212> TYPE: DNA
<213> ORGANISM: Artificial Sequence
<220> FEATURE:
<223> OTHER INFORMATION: CB-5?LVk3

<400> SEQUENCE: 67
cctcctgcta ctctggctcc cag 23

<210> SEQ ID NO 68
<211> LENGTH: 26
<212> TYPE: DNA
<213> ORGANISM: Artificial Sequence
<220> FEATURE:
<223> OTHER INFORMATION: CB-5?LVk4

<400> SEQUENCE: 68
tctctgttgc tctggatctc tggtgc 26

<210> SEQ ID NO 69
<211> LENGTH: 24
<212> TYPE: DNA
<213> ORGANISM: Artificial Sequence
<220> FEATURE:
<223> OTHER INFORMATION: CB-5?LVk5

<400> SEQUENCE: 69
ctcctcagct tcctcctcct ttgg 24

<210> SEQ ID NO 70
<211> LENGTH: 26
<212> TYPE: DNA
<213> ORGANISM: Artificial Sequence
<220> FEATURE:
<223> OTHER INFORMATION: CB-5?LVk6

<400> SEQUENCE: 70
aactcattgg gtttctgctg ctctgg 26

<210> SEQ ID NO 71
<211> LENGTH: 23
<212> TYPE: DNA
<213> ORGANISM: Artificial Sequence
<220> FEATURE:
<223> OTHER INFORMATION: 3'Ck-Rev494

<400> SEQUENCE: 71
gtgctgtcct tgctgtcctg ctc 23

<210> SEQ ID NO 72
<211> LENGTH: 20
<212> TYPE: DNA
<213> ORGANISM: Artificial Sequence
<220> FEATURE:
<223> OTHER INFORMATION: CB-5? LVlam1

<400> SEQUENCE: 72
ctcctcgctc actgcacagg 20

<210> SEQ ID NO 73
<211> LENGTH: 20
<212> TYPE: DNA
<213> ORGANISM: Artificial Sequence
<220> FEATURE:
<223> OTHER INFORMATION: CB-5? LVlam2

<400> SEQUENCE: 73
ctcctctctc actgcacagg 20

<210> SEQ ID NO 74
<211> LENGTH: 20
<212> TYPE: DNA
<213> ORGANISM: Artificial Sequence
<220> FEATURE:
<223> OTHER INFORMATION: CB-5? LVlam3

<400> SEQUENCE: 74
ctcctcactc gggacacagg 20

<210> SEQ ID NO 75
<211> LENGTH: 20
<212> TYPE: DNA
<213> ORGANISM: Artificial Sequence
<220> FEATURE:
<223> OTHER INFORMATION: CB-5? LVlam4

<400> SEQUENCE: 75
atggcctgga cccctctctg 20

<210> SEQ ID NO 76
<211> LENGTH: 24
<212> TYPE: DNA
<213> ORGANISM: Artificial Sequence
<220> FEATURE:
<223> OTHER INFORMATION: CB-5? LVlam5

<400> SEQUENCE: 76
atggcatgga tccctctctt cctc 24

<210> SEQ ID NO 77
<211> LENGTH: 24
<212> TYPE: DNA
<213> ORGANISM: Artificial Sequence
<220> FEATURE:
<223> OTHER INFORMATION: 3?Clam-Rev

<400> SEQUENCE: 77
caagccaaca aggccacact agtg 24

<210> SEQ ID NO 78
<211> LENGTH: 45
<212> TYPE: DNA
<213> ORGANISM: Artificial Sequence
<220> FEATURE:
<223> OTHER INFORMATION: CB-VH1a

<400> SEQUENCE: 78
gctcgcagca tagccggcca tggcccaggt gcagctggtg cagtc 45

<210> SEQ ID NO 79
<211> LENGTH: 45
<212> TYPE: DNA
<213> ORGANISM: Artificial Sequence
<220> FEATURE:
<223> OTHER INFORMATION: CB-VH1b

<400> SEQUENCE: 79
gctcgcagca tagccggcca tggcccaggt ccagctggtg cagtc 45

<210> SEQ ID NO 80
<211> LENGTH: 45
<212> TYPE: DNA

<213> ORGANISM: Artificial Sequence
<220> FEATURE:
<223> OTHER INFORMATION: CB-VH1c

<400> SEQUENCE: 80
gctcgcagca tagccggcca tggcccaggt tcagctggtg cagtc 45

<210> SEQ ID NO 81
<211> LENGTH: 45
<212> TYPE: DNA
<213> ORGANISM: Artificial Sequence
<220> FEATURE:
<223> OTHER INFORMATION: CB-VH1d

<400> SEQUENCE: 81
gctcgcagca tagccggcca tggcccaggt ccagcttgtg cagtc 45

<210> SEQ ID NO 82
<211> LENGTH: 48
<212> TYPE: DNA
<213> ORGANISM: Artificial Sequence
<220> FEATURE:
<223> OTHER INFORMATION: CB-VH2a

<400> SEQUENCE: 82
gctcgcagca tagccggcca tggcccaggt caccttgagg gagtctgg 48

<210> SEQ ID NO 83
<211> LENGTH: 48
<212> TYPE: DNA
<213> ORGANISM: Artificial Sequence
<220> FEATURE:
<223> OTHER INFORMATION: CB-VH2b

<400> SEQUENCE: 83
gctcgcagca tagccggcca tggcccaggt caccttgaag gagtctgg 48

<210> SEQ ID NO 84
<211> LENGTH: 45
<212> TYPE: DNA
<213> ORGANISM: Artificial Sequence
<220> FEATURE:
<223> OTHER INFORMATION: CB-VH3a

<400> SEQUENCE: 84
gctcgcagca tagccggcca tggcccaggt gcagctggtg gagtc 45

<210> SEQ ID NO 85
<211> LENGTH: 45
<212> TYPE: DNA
<213> ORGANISM: Artificial Sequence
<220> FEATURE:
<223> OTHER INFORMATION: CB-VH3b

<400> SEQUENCE: 85
gctcgcagca tagccggcca tggccgaggt gcagctgttg gagtc 45

<210> SEQ ID NO 86
<211> LENGTH: 45
<212> TYPE: DNA
<213> ORGANISM: Artificial Sequence
<220> FEATURE:
<223> OTHER INFORMATION: CB-VH3c

<400> SEQUENCE: 86
gctcgcagca tagccggcca tggccgaggt gcagctggtg gagtc 45

<210> SEQ ID NO 87
<211> LENGTH: 47
<212> TYPE: DNA
<213> ORGANISM: Artificial Sequence
<220> FEATURE:
<223> OTHER INFORMATION: CB-VH3d

<400> SEQUENCE: 87
gctcgcagca tagccggcca tggcccaggt acagctggtg gagtctg 47

<210> SEQ ID NO 88
<211> LENGTH: 43
<212> TYPE: DNA
<213> ORGANISM: Artificial Sequence
<220> FEATURE:
<223> OTHER INFORMATION: CB-VH4a

<400> SEQUENCE: 88
gctcgcagca tagccggcca tggcccagst gcagctgcag gag 43

<210> SEQ ID NO 89
<211> LENGTH: 46
<212> TYPE: DNA
<213> ORGANISM: Artificial Sequence
<220> FEATURE:
<223> OTHER INFORMATION: CB-VH4b

<400> SEQUENCE: 89
gctcgcagca tagccggcca tggcccaggt gcagctacag cagtgg 46

<210> SEQ ID NO 90
<211> LENGTH: 45
<212> TYPE: DNA
<213> ORGANISM: Artificial Sequence
<220> FEATURE:
<223> OTHER INFORMATION: CB-VH5

<400> SEQUENCE: 90
gctcgcagca tagccggcca tggccgaggt gcagctggtg cagtc 45

<210> SEQ ID NO 91
<211> LENGTH: 47
<212> TYPE: DNA
<213> ORGANISM: Artificial Sequence
<220> FEATURE:
<223> OTHER INFORMATION: CB-VH6

<400> SEQUENCE: 91
gctcgcagca tagccggcca tggcccaggt acagctgcag cagtcag 47

<210> SEQ ID NO 92
<211> LENGTH: 47
<212> TYPE: DNA
<213> ORGANISM: Artificial Sequence
<220> FEATURE:
<223> OTHER INFORMATION: CB-VH7

<400> SEQUENCE: 92
gctcgcagca tagccggcca tggcccaggt gcagctggtg caatctg 47

<210> SEQ ID NO 93
<211> LENGTH: 32
<212> TYPE: DNA
<213> ORGANISM: Artificial Sequence
<220> FEATURE:

<223> OTHER INFORMATION: 3?SalIJH 1/2/4/5

<400> SEQUENCE: 93
tgcgaagtcg acgctgagga gacggtgacc ag 32

<210> SEQ ID NO 94
<211> LENGTH: 34
<212> TYPE: DNA
<213> ORGANISM: Artificial Sequence
<220> FEATURE:
<223> OTHER INFORMATION: 3?SalIJH3

<400> SEQUENCE: 94
tgcgaagtcg acgctgaaga gacggtgacc attg 34

<210> SEQ ID NO 95
<211> LENGTH: 33
<212> TYPE: DNA
<213> ORGANISM: Artificial Sequence
<220> FEATURE:
<223> OTHER INFORMATION: 3?SalIJH6

<400> SEQUENCE: 95
tgcgaagtcg acgctgagga gacggtgacc gtg 33

<210> SEQ ID NO 96
<211> LENGTH: 43
<212> TYPE: DNA
<213> ORGANISM: Artificial Sequence
<220> FEATURE:
<223> OTHER INFORMATION: CB-VK1a

<400> SEQUENCE: 96
ctaccgtggc ctaggcggcc gacatccaga tgacccagtc tcc 43

<210> SEQ ID NO 97
<211> LENGTH: 43
<212> TYPE: DNA
<213> ORGANISM: Artificial Sequence
<220> FEATURE:
<223> OTHER INFORMATION: CB-VK1b

<400> SEQUENCE: 97
ctaccgtggc ctaggcggcc gacatccagt tgacccagtc tcc 43

<210> SEQ ID NO 98
<211> LENGTH: 43
<212> TYPE: DNA
<213> ORGANISM: Artificial Sequence
<220> FEATURE:
<223> OTHER INFORMATION: CB-VK1c

<400> SEQUENCE: 98
ctaccgtggc ctaggcggcc gccatccagt tgacccagtc tcc 43

<210> SEQ ID NO 99
<211> LENGTH: 47
<212> TYPE: DNA
<213> ORGANISM: Artificial Sequence
<220> FEATURE:
<223> OTHER INFORMATION: CB-VK2a

<400> SEQUENCE: 99
ctaccgtggc ctaggcggcc gatrttgtga tgactcagtc tccactc 47

<210> SEQ ID NO 100
<211> LENGTH: 45
<212> TYPE: DNA
<213> ORGANISM: Artificial Sequence
<220> FEATURE:
<223> OTHER INFORMATION: CB-VK3a

<400> SEQUENCE: 100
ctaccgtggc ctaggcggcc gaaattgtgt tgacgcagtc tccag 45

<210> SEQ ID NO 101
<211> LENGTH: 45
<212> TYPE: DNA
<213> ORGANISM: Artificial Sequence
<220> FEATURE:
<223> OTHER INFORMATION: CB-VK3b

<400> SEQUENCE: 101
ctaccgtggc ctaggcggcc gaaattgtgt tgacacagtc tccag 45

<210> SEQ ID NO 102
<211> LENGTH: 45
<212> TYPE: DNA
<213> ORGANISM: Artificial Sequence
<220> FEATURE:
<223> OTHER INFORMATION: CB-VK3c

<400> SEQUENCE: 102
ctaccgtggc ctaggcggcc gaaatagtga tgacgcagtc tccag 45

<210> SEQ ID NO 103
<211> LENGTH: 43
<212> TYPE: DNA
<213> ORGANISM: Artificial Sequence
<220> FEATURE:
<223> OTHER INFORMATION: CB-Vk4

<400> SEQUENCE: 103
ctaccgtggc ctaggcggcc gacatcgtga tgacccagtc tcc 43

<210> SEQ ID NO 104
<211> LENGTH: 43
<212> TYPE: DNA
<213> ORGANISM: Artificial Sequence
<220> FEATURE:
<223> OTHER INFORMATION: CB-Vk5

<400> SEQUENCE: 104
ctaccgtggc ctaggcggcc gaaacgacac tcacgcagtc tcc 43

<210> SEQ ID NO 105
<211> LENGTH: 45
<212> TYPE: DNA
<213> ORGANISM: Artificial Sequence
<220> FEATURE:
<223> OTHER INFORMATION: CB-Vk6

<400> SEQUENCE: 105
ctaccgtggc ctaggcggcc gaaattgtgc tgactcagtc tccag 45

<210> SEQ ID NO 106
<211> LENGTH: 46
<212> TYPE: DNA
<213> ORGANISM: Artificial Sequence
<220> FEATURE:
<223> OTHER INFORMATION: 3'Jk1/4 Rev IIa-L

<400> SEQUENCE: 106
gaagacagat ggtgcagcca cagttcgttt gatytccacc ttggtc 46

<210> SEQ ID NO 107
<211> LENGTH: 46
<212> TYPE: DNA
<213> ORGANISM: Artificial Sequence
<220> FEATURE:
<223> OTHER INFORMATION: 3'Jk2 Rev IIb-L

<400> SEQUENCE: 107
gaagacagat ggtgcagcca cagttcgttt gatctccagc ttggtc 46

<210> SEQ ID NO 108
<211> LENGTH: 46
<212> TYPE: DNA
<213> ORGANISM: Artificial Sequence
<220> FEATURE:
<223> OTHER INFORMATION: 3'Jk3 Rev IIc-L

<400> SEQUENCE: 108
gaagacagat ggtgcagcca cagttcgttt gatatccact ttggtc 46

<210> SEQ ID NO 109
<211> LENGTH: 46
<212> TYPE: DNA
<213> ORGANISM: Artificial Sequence
<220> FEATURE:
<223> OTHER INFORMATION: 3'Jk5 Rev IId-L

<400> SEQUENCE: 109
gaagacagat ggtgcagcca cagttcgttt aatctccagt cgtgtc 46

<210> SEQ ID NO 110
<211> LENGTH: 46
<212> TYPE: DNA
<213> ORGANISM: Artificial Sequence
<220> FEATURE:
<223> OTHER INFORMATION: CB-VL1

<400> SEQUENCE: 110
ctaccgtggc ctaggcggcc aattttatgc tgactcagcc ccactc 46

<210> SEQ ID NO 111
<211> LENGTH: 40
<212> TYPE: DNA
<213> ORGANISM: Artificial Sequence
<220> FEATURE:
<223> OTHER INFORMATION: CB-VL2

<400> SEQUENCE: 111
ctaccgtggc ctaggcggcc tcctatgtgc tgactcagcc 40

<210> SEQ ID NO 112
<211> LENGTH: 40
<212> TYPE: DNA
<213> ORGANISM: Artificial Sequence
<220> FEATURE:
<223> OTHER INFORMATION: CB-VL3

<400> SEQUENCE: 112
ctaccgtggc ctaggcggcc cagtctgtgc tgacgcagcc 40

<210> SEQ ID NO 113
<211> LENGTH: 40

<212> TYPE: DNA
<213> ORGANISM: Artificial Sequence
<220> FEATURE:
<223> OTHER INFORMATION: CB-VL4

<400> SEQUENCE: 113
ctaccgtggc ctaggcggcc cagtctgtcg tgacgcagcc 40

<210> SEQ ID NO 114
<211> LENGTH: 40
<212> TYPE: DNA
<213> ORGANISM: Artificial Sequence
<220> FEATURE:
<223> OTHER INFORMATION: CB-VL5

<400> SEQUENCE: 114
ctaccgtggc ctaggcggcc cagtctgccc tgactcagcc 40

<210> SEQ ID NO 115
<211> LENGTH: 42
<212> TYPE: DNA
<213> ORGANISM: Artificial Sequence
<220> FEATURE:
<223> OTHER INFORMATION: CB-VL6

<400> SEQUENCE: 115
ctaccgtggc ctaggcggcc tcttctgagc tgactcagga cc 42

<210> SEQ ID NO 116
<211> LENGTH: 43
<212> TYPE: DNA
<213> ORGANISM: Artificial Sequence
<220> FEATURE:
<223> OTHER INFORMATION: CB-VL7

<400> SEQUENCE: 116
ctaccgtggc ctaggcggcc tcctatgagc tgactcagcc acc 43

<210> SEQ ID NO 117
<211> LENGTH: 27
<212> TYPE: DNA
<213> ORGANISM: Artificial Sequence
<220> FEATURE:
<223> OTHER INFORMATION: 3'Clam-Step II

<400> SEQUENCE: 117
ctcagaggag ggygggaaca gagtgac 27

<210> SEQ ID NO 118
<211> LENGTH: 414
<212> TYPE: DNA
<213> ORGANISM: Artificial Sequence
<220> FEATURE:
<223> OTHER INFORMATION: IGKC

<400> SEQUENCE: 118
cgaactgtgg ctgcaccatc tgtcttcatc ttcccgccat ctgatgagca gcttaaatct 60
ggaactgcct ctgttgtgtg ccttctaaat aacttctatc cccgtgaggc caaagtacag 120
tggaaggtgg ataacgccct ccaatcgggt aactcccagg agagtgtcac agagcaggac 180
agcaaggaca gcacctacag cctcagcagc acccttacgc ttagcaaagc agactacgag 240
aaacacaaag tctacgcctg cgaagtcacc catcagggcc tcagctcgcc cgtcacaaag 300
agcttcaacc gcggagagtg ttaatctaga aataaggagg atataattat gaaatacctg 360
ctgccgaccg cagccgctgg tctgctgctg ctcgcagcat agccggccat ggcc 414

<210> SEQ ID NO 119
<211> LENGTH: 387
<212> TYPE: DNA
<213> ORGANISM: Artificial Sequence
<220> FEATURE:
<223> OTHER INFORMATION: IGLC2

<400> SEQUENCE: 119
gtcactctgt tcccgccctc ctctgaggag cttcaagcca acaaggccac actggtgtgt 60
ctcataagtg acttctaccc gggagccgtg acagtggcct ggaaggcaga tagcagcccc 120
gtcaaggcgg gagtggagac caccacaccc tccaaacaaa gcaacaacaa gtacgcggcc 180
agcagctacc tgagcctgac gcctgagcag tggaagtccc acagaagcta cagctgccag 240
gtcacgcatg aagggagcac cgtggagaag acagtggccc ctacagaatg ttcataatct 300
agaaataagg aggatataat tatgaaatac ctgctgccga ccgcagccgc tggtctgctg 360
ctgctcgcag catagccggc catggcc 387

<210> SEQ ID NO 120
<211> LENGTH: 27
<212> TYPE: DNA
<213> ORGANISM: Artificial Sequence
<220> FEATURE:
<223> OTHER INFORMATION: FabLinker-F

<400> SEQUENCE: 120
cgaactgtgg ctgcaccatc tgtcttc 27

<210> SEQ ID NO 121
<211> LENGTH: 25
<212> TYPE: DNA
<213> ORGANISM: Artificial Sequence
<220> FEATURE:
<223> OTHER INFORMATION: FabLinker-R

<400> SEQUENCE: 121
ggccatggcc ggctatgctg cgagc 25

<210> SEQ ID NO 122
<211> LENGTH: 27
<212> TYPE: DNA
<213> ORGANISM: Artificial Sequence
<220> FEATURE:
<223> OTHER INFORMATION: Lambda-Fab Linker F

<400> SEQUENCE: 122
gtcactctgt tcccrccctc ctctgag 27

<210> SEQ ID NO 123
<211> LENGTH: 20
<212> TYPE: DNA
<213> ORGANISM: Artificial Sequence
<220> FEATURE:
<223> OTHER INFORMATION: Overlap-F

<400> SEQUENCE: 123
ctaccgtggc ctaggcggcc 20

<210> SEQ ID NO 124
<211> LENGTH: 21
<212> TYPE: DNA
<213> ORGANISM: Artificial Sequence
<220> FEATURE:
<223> OTHER INFORMATION: Overlap-R

<400> SEQUENCE: 124
tgcgaagtcg acgctgarga g 21

<210> SEQ ID NO 125
<211> LENGTH: 40
<212> TYPE: PRT
<213> ORGANISM: Artificial Sequence
<220> FEATURE:
<223> OTHER INFORMATION: SYM-1706

<400> SEQUENCE: 125

Lys Gln Arg Gln Asn Lys Pro Pro Asn Lys Pro Asn Asn Asp Phe His
1 5 10 15

Phe Glu Val Phe Asn Phe Val Pro Cys Ser Ile Cys Ser Asn Asn Pro
20 25 30

Thr Cys Trp Ala Ile Cys Lys Arg
35 40

<210> SEQ ID NO 126
<211> LENGTH: 20
<212> TYPE: DNA
<213> ORGANISM: Artificial Sequence
<220> FEATURE:
<223> OTHER INFORMATION: SeqpCBFab-HCF

<400> SEQUENCE: 126
tgaaatacct gctgccgacc 20

<210> SEQ ID NO 127
<211> LENGTH: 8970
<212> TYPE: DNA
<213> ORGANISM: Artificial Sequence
<220> FEATURE:
<223> OTHER INFORMATION: pCP9-kappa sequence

<400> SEQUENCE: 127
tactcttcct ttttcaatat tattgaagca tttatcaggg ttattgtctc atgagcggat 60
acatatttga atgtatttag aaaaataaac aaataggggt tccgcgcaca tttccccgaa 120
aagtgccacc tgacgtcgac ggatcgggag atctcccgat cccctatggt gcactctcag 180
tacaatctgc tctgatgccg catagttaag ccagtatctg ctccctgctt gtgtgttgga 240
ggtcgctgag tagtgcgcga gcaaaattta agctacaaca aggcaaggct tgaccgacaa 300
ttgcatgaag aatctgctta gggttaggcg ttttgcgctg cttcgctagg tggtcaatat 360
tggccattag ccatattatt cattggttat atagcataaa tcaatattgg ctattggcca 420
ttgcatacgt tgtatccata tcataatatg tacatttata ttggctcatg tccaacatta 480
ccgccatgtt gacattgatt attgactagt tattaatagt aatcaattac ggggtcatta 540
gttcatagcc catatatgga gttccgcgtt acataactta cggtaaatgg cccgcctggc 600
tgaccgccca acgacccccg cccattgacg tcaataatga cgtatgttcc catagtaacg 660
ccaataggga ctttccattg acgtcaatgg gtggagtatt tacggtaaac tgcccacttg 720
gcagtacatc aagtgtatca tatgccaagt acgcccccta ttgacgtcaa tgacggtaaa 780
tggcccgcct ggcattatgc ccagtacatg accttatggg actttcctac ttggcagtac 840
atctacgtat tagtcatcgc tattaccatg gtgatgcggt tttggcagta catcaatggg 900
cgtggatagc ggtttgactc acggggattt ccaagtctcc accccattga cgtcaatggg 960

```
agtttgtttt ggcaccaaaa tcaacgggac tttccaaaat gtcgtaacaa ctccgcccca   1020
ttgacgcaaa tgggcggtag gcgtgtacgg tgggaggtct atataagcag agctcgttta   1080
gtgaaccgtc agatcgcctg gagacgccat ccacgctgtt ttgacctcca tagaagacac   1140
cgggaccgat ccagcctccg cggccgggaa cggtgcattg gaagcttggt accgagctcg   1200
gatccttaat taactcgagg cccgagcccg ggcgagccca gacactggac gctgaacctc   1260
gcggacagtt aagaacccag gggcctctgc gccctgggcc cagctctgtc ccacaccgcg   1320
gtcacatggc accacctctc ttgcagcctc caccaagggc ccatcggtct tccccctggc   1380
accctcctcc aagagcacct ctgggggcac agcggccctg ggctgcctgg tcaaggacta   1440
cttccccgaa ccggtgacgg tgtcgtggaa ctcaggcgcc ctgaccagcg gcgtgcacac   1500
cttcccggct gtcctacagt cctcaggact ctactccctc agcagcgtgg tgaccgtgcc   1560
ctccagcagc ttgggcaccc agacctacat ctgcaacgtg aatcacaagc ccagcaacac   1620
caaggtggac aagagagttg gtgagaggcc agcacaggga gggagggtgt ctgctggaag   1680
ccaggctcag cgctcctgcc tggacgcatc ccggctatgc agtcccagtc cagggcagca   1740
aggcaggccc cgtctgcctc ttcacccgga ggcctctgcc cgccccactc atgctcaggg   1800
agagggtctt ctggcttttt ccccaggctc tgggcaggca cgggctaggt gcccctaacc   1860
caggccctgc acacaaaggg gcaggtgctg ggctcagacc tgccaagagc catatccggg   1920
aggaccctgc ccctgaccta agcccacccc aaaggccaaa ctctccactc cctcagctcg   1980
gacaccttct ctcctcccag attccagtaa ctcccaatct tctctctgca gagcccaaat   2040
cttgtgacaa aactcacaca tgcccaccgt gcccaggtaa gccagcccag gcctcgccct   2100
ccagctcaag gcgggacagg tgccctagag tagcctgcat ccagggacag gccccagccg   2160
ggtgctgaca cgtccacctc catctcttcc tcagcacctg aactcctggg gggaccgtca   2220
gtcttcctct tccccccaaa acccaaggac accctcatga tctcccggac ccctgaggtc   2280
acatgcgtgg tggtggacgt gagccacgaa gaccctgagg tcaagttcaa ctggtacgtg   2340
gacggcgtgg aggtgcataa tgccaagaca aagccgcggg aggagcagta caacagcacg   2400
taccgtgtgg tcagcgtcct caccgtcctg caccaggact ggctgaatgg caaggagtac   2460
aagtgcaagg tctccaacaa agccctccca gcccccatcg agaaaaccat ctccaaagcc   2520
aaaggtggga cccgtggggt gcgagggcca catggacaga ggccggctcg gcccaccctc   2580
tgccctgaga gtgaccgctg taccaacctc tgtccctaca gggcagcccc gagaaccaca   2640
ggtgtacacc ctgcccccat cccgggagga gatgaccaag aaccaggtca gcctgacctg   2700
cctggtcaaa ggcttctatc ccagcgacat cgccgtggag tgggagagca atgggcagcc   2760
ggagaacaac tacaagacca cgcctcccgt gctggactcc gacggctcct tcttcctcta   2820
tagcaagctc accgtggaca agagcaggtg gcagcagggg aacgtcttct catgctccgt   2880
gatgcatgag gctctgcaca accactacac gcagaagagc ctctccctgt ctccgggtaa   2940
atgagctagc gaattcaccg gtaccaagct taagtttaaa ccgctgatca gcctcgactg   3000
tgccttctag ttgccagcca tctgttgttt gcccctcccc cgtgccttcc ttgaccctgg   3060
aaggtgccac tcccactgtc ctttcctaat aaaatgagga aattgcatcg cattgtctga   3120
gtaggtgtca ttctattctg gggggtgggg tggggcagga cagcaagggg gaggattggg   3180
aagacaatag caggcatgct ggggatgcgg tgggctctat ggcttctgag gcggaaagaa   3240
ccagctgggg ctctaggggg tatccccacg cgccctgtag cggcgcatta agcgcggcgg   3300
```

```
gtgtggtggt tacgcgcagc gtgaccgcta cacttgccag cgccctagcgc ccgctccttt   3360
cgctttcttc ccttcctttc tcgccacgtt cgccggcttt ccccgtcaag ctctaaatcg   3420
ggggctccct ttagggttcc gatttagtgc tttacggcac ctcgacccca aaaaacttga   3480
ttagggtgat ggttcacgta gtgggccatc gccctgatag acggtttttc gccctttgac   3540
gttggagtcc acgttcttta atagtggact cttgttccaa actggaacaa cactcaaccc   3600
tatctcggtc tattcttttg atttataagg gattttgccg atttcggcct attggttaaa   3660
aaatgagctg atttaacaaa aatttaacgc gaattaattc tgtggaatgt gtgtcagtta   3720
gggtgtggaa agtccccagg ctccccagca ggcagaagta tgcaaagcat gcatctcaat   3780
tagtcagcaa ccaggtgtgg aaagtcccca ggctccccag caggcagaag tatgcaaagc   3840
atgcatctca attagtcagc aaccatagtc ccgcccctaa ctccgcccat cccgccccta   3900
actccgccca gttccgccca ttctccgccc catggctgac taattttttt tatttatgca   3960
gaggccgagg ccgcctctgc ctctgagcta ttccagaagt agtgaggagg cttttttgga   4020
ggcctaggct tttgcaaaaa gctcccggga gcttggatat ccattttcgg atctgatcaa   4080
gagacaggat gaggatcgtt tcgcatgatt gaacaagatg gattgcacgc aggttctccg   4140
gccgcttggg tggagaggct attcggctat gactgggcac aacagacaat cggctgctct   4200
gatgccgccg tgttccggct gtcagcgcag gggcgcccgg ttctttttgt caagaccgac   4260
ctgtccggtg ccctgaatga actgcaggac gaggcagcgc ggctatcgtg gctggccacg   4320
acgggcgttc cttgcgcagc tgtgctcgac gttgtcactg aagcgggaag ggactggctg   4380
ctattgggcg aagtgccggg gcaggatctc ctgtcatctc accttgctcc tgccgagaaa   4440
gtatccatca tggctgatgc aatgcggcgg ctgcatacgc ttgatccggc tacctgccca   4500
ttcgaccacc aagcgaaaca tcgcatcgag cgagcacgta ctcggatgga agccggtctt   4560
gtcgatcagg atgatctgga cgaagagcat caggggctcg cgccagccga actgttcgcc   4620
aggctcaagg cgcgcatgcc cgacggcgag gatctcgtcg tgacccatgg cgatgcctgc   4680
ttgccgaata tcatggtgga aaatggccgc ttttctggat tcatcgactg tggccggctg   4740
ggtgtggcgg accgctatca ggacatagcg ttggctaccc gtgatattgc tgaagagctt   4800
ggcggcgaat gggctgaccg cttcctcgtg ctttacggta tcgccgctcc cgattcgcag   4860
cgcatcgcct tctatcgcct tcttgacgag ttcttctgag cgggactctg gggttcggtg   4920
ctacgagatt tcgattccac cgccgccttc tatgaaaggt tgggcttcgg aatcgttttc   4980
cgggacgccg gctggatgat cctccagcgc ggggatctca tgctggagtt cttcgcccac   5040
cccaacttgt ttattgcagc ttataatggt tacaaataaa gcaatagcat cacaaatttc   5100
acaaataaag catttttttc actgcattct agttgtggtt tgtccaaact catcaatgta   5160
tcttatcatg tctgtatacc gtcgacctct agctagagct tggcgtaatc atggtcatag   5220
ctgtttcctg tgtgaaattg ttatccgctc acaattccac acaacatacg agccggaagc   5280
ataaagtgta aagcctgggg tgcctaatga gtgagctaac tcacattaat tgcgttgcgc   5340
tcactgcccg ctttccagtc gggaaacctg tcgtgccaga attgcatgaa gaatctgctt   5400
agggttaggc gttttgcgct gcttcgctag gtggtcaata ttggccatta gccatattat   5460
tcattggtta tatagcataa atcaatattg gctattggcc attgcatacg ttgtatccat   5520
atcataatat gtacatttat attggctcat gtccaacatt accgccatgt tgacattgat   5580
tattgactag ttattaatag taatcaatta cggggtcatt agttcatagc ccatatatgg   5640
agttccgcgt tacataactt acggtaaatg gcccgcctgg ctgaccgccc aacgaccccc   5700
```

```
gcccattgac gtcaataatg acgtatgttc ccatagtaac gccaataggg actttccatt   5760
gacgtcaatg ggtggagtat ttacggtaaa ctgcccactt ggcagtacat caagtgtatc   5820
atatgccaag tacgccccct attgacgtca atgacggtaa atggcccgcc tggcattatg   5880
cccagtacat gaccttatgg gactttccta cttggcagta catctacgta ttagtcatcg   5940
ctattaccat ggtgatgcgg ttttggcagt acatcaatgg gcgtggatag cggtttgact   6000
cacggggatt tccaagtctc caccccattg acgtcaatgg gagtttgttt tggcaccaaa   6060
atcaacggga ctttccaaaa tgtcgtaaca actccgcccc attgacgcaa atgggcggta   6120
ggcgtgtacg gtgggaggtc tatataagca gagctcgttt agtgaaccgt cagatcgcct   6180
ggagacgcca tccacgctgt tttgacctcc atagaagaca ccgggaccga tccagcctcc   6240
gcggccggga acggtgcatt ggaagcttgg taccggtgaa ttcggcgcgc cagatctgcg   6300
gccgctagga agaaactcaa aacatcaaga ttttaaatac gcttcttggt ctccttgcta   6360
taattatctg ggataagcat gctgttttct gtctgtccct aacatgccct gtgattatcc   6420
gcaaacaaca cacccaaggg cagaactttg ttacttaaac accatcctgt ttgcttcttt   6480
cctcaggaac tgtggctgca ccatctgtct tcatcttccc gccatctgat gagcagttga   6540
aatctggaac tgcctctgtt gtgtgcctgc tgaataactt ctatcccaga gaggccaaag   6600
tacagtggaa ggtggataac gccctccaat cgggtaactc ccaggagagt gtcacagagc   6660
aggacagcaa ggacagcacc tacagcctca gcagcaccct gacgctgagc aaagcagact   6720
acgagaaaca caaagtctac gcctgcgaag tcacccatca gggcctgagc tcgcccgtca   6780
caaagagctt caacagggga gagtgttagt taacggatcg atccgagctc ggtaccaagc   6840
ttaagtttaa accgctgatc agcctcgact gtgccttcta gttgccagcc atctgttgtt   6900
tgcccctccc ccgtgccttc cttgaccctg gaaggtgcca ctcccactgt cctttcctaa   6960
taaaatgagg aaattgcatc gcattgtctg agtaggtgtc attctattct ggggggtggg   7020
gtggggcagg acagcaaggg ggaggattgg gaagacaata gcaggcatgc tggggatgcg   7080
gtgggctcta tggcttctga ggcggaaaga accagctgca ttaatgaatc ggccaacgcg   7140
cggggagagg cggtttgcgt attgggcgct cttccgcttc ctcgctcact gactcgctgc   7200
gctcggtcgt tcggctgcgg cgagcggtat cagctcactc aaaggcggta atacggttat   7260
ccacagaatc aggggataac gcaggaaaga acatgtgagc aaaaggccag caaaaggcca   7320
ggaaccgtaa aaaggccgcg ttgctggcgt ttttccatag gctccgcccc cctgacgagc   7380
atcacaaaaa tcgacgctca agtcagaggt ggcgaaaccc gacaggacta taaagatacc   7440
aggcgtttcc ccctggaagc tccctcgtgc gctctcctgt tccgaccctg ccgcttaccg   7500
gatacctgtc cgcctttctc ccttcgggaa gcgtggcgct ttctcatagc tcacgctgta   7560
ggtatctcag ttcggtgtag gtcgttcgct ccaagctggg ctgtgtgcac gaaccccccg   7620
ttcagcccga ccgctgcgcc ttatccggta actatcgtct tgagtccaac ccggtaagac   7680
acgacttatc gccactggca gcagccactg gtaacaggat tagcagagcg aggtatgtag   7740
gcggtgctac agagttcttg aagtggtggc ctaactacgg ctacactaga agaacagtat   7800
ttggtatctg cgctctgctg aagccagtta ccttcggaaa aagagttggt agctcttgat   7860
ccggcaaaca aaccaccgct ggtagcggtg gtttttttgt ttgcaagcag cagattacgc   7920
gcagaaaaaa aggatctcaa gaagatcctt tgatcttttc tacggggtct gacgctcagt   7980
ggaacgaaaa ctcacgttaa gggattttgg tcatgagatt atcaaaaagg atcttcacct   8040
```

```
agatcctttt aaattaaaaa tgaagtttta aatcaatcta aagtatatat gagtaaactt   8100

ggtctgacag ttaccaatgc ttaatcagtg aggcacctat ctcagcgatc tgtctatttc   8160

gttcatccat agttgcctga ctccccgtcg tgtagataac tacgatacgg gagggcttac   8220

catctggccc cagtgctgca atgataccgc gagacccacg ctcaccggct ccagatttat   8280

cagcaataaa ccagccagcc ggaagggccg agcgcagaag tggtcctgca actttatccg   8340

cctccatcca gtctattaat tgttgccggg aagctagagt aagtagttcg ccagttaata   8400

gtttgcgcaa cgttgttgcc attgctacag gcatcgtggt gtcacgctcg tcgtttggta   8460

tggcttcatt cagctccggt tcccaacgat caaggcgagt tacatgatcc cccatgttgt   8520

gcaaaaaagc ggttagctcc ttcggtcctc cgatcgttgt cagaagtaag ttggccgcag   8580

tgttatcact catggttatg gcagcactgc ataattctct tactgtcatg ccatccgtaa   8640

gatgcttttc tgtgactggt gagtactcaa ccaagtcatt ctgagaatag tgtatgcggc   8700

gaccgagttg ctcttgcccg gcgtcaatac gggataatac cgcgccacat agcagaactt   8760

taaaagtgct catcattgga aaacgttctt cggggcgaaa actctcaagg atcttaccgc   8820

tgttgagatc cagttcgatg taacccactc gtgcacccaa ctgatcttca gcatctttta   8880

ctttcaccag cgtttctggg tgagcaaaaa caggaaggca aaatgccgca aaaaagggaa   8940

taagggcgac acggaaatgt tgaatactca                                    8970
```

```
<210> SEQ ID NO 128
<211> LENGTH: 8969
<212> TYPE: DNA
<213> ORGANISM: Artificial Sequence
<220> FEATURE:
<223> OTHER INFORMATION: pCP9-lambda sequence

<400> SEQUENCE: 128
```

```
tactcttcct ttttcaatat tattgaagca tttatcaggg ttattgtctc atgagcggat     60

acatatttga atgtatttag aaaaataaac aaataggggt tccgcgcaca tttccccgaa    120

aagtgccacc tgacgtcgac ggatcgggag atctcccgat cccctatggt gcactctcag    180

tacaatctgc tctgatgccg catagttaag ccagtatctg ctccctgctt gtgtgttgga    240

ggtcgctgag tagtgcgcga gcaaaattta agctacaaca aggcaaggct tgaccgacaa    300

ttgcatgaag aatctgctta gggttaggcg ttttgcgctg cttcgctagg tggtcaatat    360

tggccattag ccatattatt cattggttat atagcataaa tcaatattgg ctattggcca    420

ttgcatacgt tgtatccata tcataatatg tacatttata ttggctcatg tccaacatta    480

ccgccatgtt gacattgatt attgactagt tattaatagt aatcaattac ggggtcatta    540

gttcatagcc catatatgga gttccgcgtt acataactta cggtaaatgg cccgcctggc    600

tgaccgccca acgacccccg cccattgacg tcaataatga cgtatgttcc catagtaacg    660

ccaataggga ctttccattg acgtcaatgg gtggagtatt tacggtaaac tgcccacttg    720

gcagtacatc aagtgtatca tatgccaagt acgcccccta ttgacgtcaa tgacggtaaa    780

tggcccgcct ggcattatgc ccagtacatg accttatggg actttcctac ttggcagtac    840

atctacgtat tagtcatcgc tattaccatg gtgatgcggt tttggcagta catcaatggg    900

cgtggatagc ggtttgactc acggggattt ccaagtctcc accccattga cgtcaatggg    960

agtttgtttt ggcaccaaaa tcaacgggac tttccaaaat gtcgtaacaa ctccgcccca   1020

ttgacgcaaa tgggcggtag gcgtgtacgg tgggaggtct atataagcag agctcgttta   1080

gtgaaccgtc agatcgcctg gagacgccat ccacgctgtt ttgacctcca tagaagacac   1140
```

```
cgggaccgat ccagcctccg cggccgggaa cggtgcattg gaagcttggt accgagctcg   1200
gatccttaat taactcgagg cccgagcccg ggcgagccca gacactggac gctgaacctc   1260
gcggacagtt aagaacccag gggcctctgc gccctgggcc cagctctgtc ccacaccgcg   1320
gtcacatggc accacctctc ttgcagcctc caccaagggc ccatcggtct tccccctggc   1380
accctcctcc aagagcacct ctgggggcac agcggccctg ggctgcctgg tcaaggacta   1440
cttccccgaa ccggtgacgg tgtcgtggaa ctcaggcgcc ctgaccagcg gcgtgcacac   1500
cttcccggct gtcctacagt cctcaggact ctactccctc agcagcgtgg tgaccgtgcc   1560
ctccagcagc ttgggcaccc agacctacat ctgcaacgtg aatcacaagc ccagcaacac   1620
caaggtggac aagagagttg gtgagaggcc agcacaggga gggagggtgt ctgctggaag   1680
ccaggctcag cgctcctgcc tggacgcatc ccggctatgc agtcccagtc cagggcagca   1740
aggcaggccc cgtctgcctc ttcacccgga ggcctctgcc cgccccactc atgctcaggg   1800
agagggtctt ctggcttttt ccccaggctc tgggcaggca cgggctaggt gcccctaacc   1860
caggccctgc acacaaaggg gcaggtgctg ggctcagacc tgccaagagc catatccggg   1920
aggaccctgc ccctgaccta agcccacccc aaaggccaaa ctctccactc cctcagctcg   1980
gacaccttct ctcctcccag attccagtaa ctcccaatct tctctctgca gagcccaaat   2040
cttgtgacaa aactcacaca tgcccaccgt gcccaggtaa gccagcccag gcctcgccct   2100
ccagctcaag gcgggacagg tgccctagag tagcctgcat ccagggacag gccccagccg   2160
ggtgctgaca cgtccacctc catctcttcc tcagcacctg aactcctggg gggaccgtca   2220
gtcttcctct tccccccaaa acccaaggac accctcatga tctcccggac ccctgaggtc   2280
acatgcgtgg tggtggacgt gagccacgaa gaccctgagg tcaagttcaa ctggtacgtg   2340
gacggcgtgg aggtgcataa tgccaagaca aagccgcggg aggagcagta caacagcacg   2400
taccgtgtgg tcagcgtcct caccgtcctg caccaggact ggctgaatgg caaggagtac   2460
aagtgcaagg tctccaacaa agccctccca gcccccatcg agaaaaccat ctccaaagcc   2520
aaaggtggga cccgtggggt gcgagggcca catggacaga ggccggctcg gcccaccctc   2580
tgccctgaga gtgaccgctg taccaacctc tgtccctaca gggcagcccc gagaaccaca   2640
ggtgtacacc ctgcccccat cccgggagga gatgaccaag aaccaggtca gcctgacctg   2700
cctggtcaaa ggcttctatc ccagcgacat cgccgtggag tgggagagca atgggcagcc   2760
ggagaacaac tacaagacca cgcctcccgt gctggactcc gacggctcct tcttcctcta   2820
tagcaagctc accgtggaca agagcaggtg gcagcagggg aacgtcttct catgctccgt   2880
gatgcatgag gctctgcaca accactacac gcagaagagc ctctccctgt ctccgggtaa   2940
atgagctagc gaattcaccg gtaccaagct taagtttaaa ccgctgatca gcctcgactg   3000
tgccttctag ttgccagcca tctgttgttt gcccctcccc cgtgccttcc ttgaccctgg   3060
aaggtgccac tcccactgtc ctttcctaat aaaatgagga aattgcatcg cattgtctga   3120
gtaggtgtca ttctattctg gggggtgggg tggggcagga cagcaagggg gaggattggg   3180
aagacaatag caggcatgct ggggatgcgg tgggctctat ggcttctgag gcggaaagaa   3240
ccagctgggg ctctaggggg tatccccacg cgccctgtag cggcgcatta agcgcggcgg   3300
gtgtggtggt tacgcgcagc gtgaccgcta cacttgccag cgccctagcgc ccgctccttt   3360
cgctttcttc ccttcctttc tcgccacgtt cgccggcttt ccccgtcaag ctctaaatcg   3420
gggggctccct ttagggttcc gatttagtgc tttacggcac ctcgacccca aaaaacttga   3480
```

```
ttagggtgat ggttcacgta gtgggccatc gccctgatag acggtttttc gccctttgac   3540
gttggagtcc acgttcttta atagtggact cttgttccaa actggaacaa cactcaaccc   3600
tatctcggtc tattcttttg atttataagg gattttgccg atttcggcct attggttaaa   3660
aaatgagctg atttaacaaa aatttaacgc gaattaattc tgtggaatgt gtgtcagtta   3720
gggtgtggaa agtccccagg ctccccagca ggcagaagta tgcaaagcat gcatctcaat   3780
tagtcagcaa ccaggtgtgg aaagtcccca ggctccccag caggcagaag tatgcaaagc   3840
atgcatctca attagtcagc aaccatagtc ccgcccctaa ctccgcccat cccgccccta   3900
actccgccca gttccgccca ttctccgccc catggctgac taattttttt tatttatgca   3960
gaggccgagg ccgcctctgc ctctgagcta ttccagaagt agtgaggagg cttttttgga   4020
ggcctaggct tttgcaaaaa gctcccggga gcttggatat ccattttcgg atctgatcaa   4080
gagacaggat gaggatcgtt tcgcatgatt gaacaagatg gattgcacgc aggttctccg   4140
gccgcttggg tggagaggct attcggctat gactgggcac aacagacaat cggctgctct   4200
gatgccgccg tgttccggct gtcagcgcag gggcgcccgg ttctttttgt caagaccgac   4260
ctgtccggtg ccctgaatga actgcaggac gaggcagcgc ggctatcgtg gctggccacg   4320
acgggcgttc cttgcgcagc tgtgctcgac gttgtcactg aagcgggaag ggactggctg   4380
ctattgggcg aagtgccggg gcaggatctc ctgtcatctc accttgctcc tgccgagaaa   4440
gtatccatca tggctgatgc aatgcggcgg ctgcatacgc ttgatccggc tacctgccca   4500
ttcgaccacc aagcgaaaca tcgcatcgag cgagcacgta ctcggatgga agccggtctt   4560
gtcgatcagg atgatctgga cgaagagcat caggggctcg cgccagccga actgttcgcc   4620
aggctcaagg cgcgcatgcc cgacggcgag gatctcgtcg tgacccatgg cgatgcctgc   4680
ttgccgaata tcatggtgga aaatggccgc ttttctggat tcatcgactg tggccggctg   4740
ggtgtggcgg accgctatca ggacatagcg ttggctaccc gtgatattgc tgaagagctt   4800
ggcggcgaat gggctgaccg cttcctcgtg ctttacggta tcgccgctcc cgattcgcag   4860
cgcatcgcct tctatcgcct tcttgacgag ttcttctgag cgggactctg gggttcggtg   4920
ctacgagatt tcgattccac cgccgccttc tatgaaaggt tgggcttcgg aatcgttttc   4980
cgggacgccg gctggatgat cctccagcgc ggggatctca tgctggagtt cttcgcccac   5040
cccaacttgt ttattgcagc ttataatggt tacaaataaa gcaatagcat cacaaatttc   5100
acaaataaag catttttttc actgcattct agttgtggtt tgtccaaact catcaatgta   5160
tcttatcatg tctgtatacc gtcgacctct agctagagct tggcgtaatc atggtcatag   5220
ctgtttcctg tgtgaaattg ttatccgctc acaattccac acaacatacg agccggaagc   5280
ataaagtgta aagcctgggg tgcctaatga gtgagctaac tcacattaat tgcgttgcgc   5340
tcactgcccg ctttccagtc gggaaacctg tcgtgccaga attgcatgaa gaatctgctt   5400
agggttaggc gttttgcgct gcttcgctag gtggtcaata ttggccatta gccatattat   5460
tcattggtta tatagcataa atcaatattg gctattggcc attgcatacg ttgtatccat   5520
atcataatat gtacatttat attggctcat gtccaacatt accgccatgt tgacattgat   5580
tattgactag ttattaatag taatcaatta cggggtcatt agttcatagc ccatatatgg   5640
agttccgcgt tacataactt acggtaaatg gcccgcctgg ctgaccgccc aacgaccccc   5700
gcccattgac gtcaataatg acgtatgttc ccatagtaac gccaataggg actttccatt   5760
gacgtcaatg ggtggagtat ttacggtaaa ctgcccactt ggcagtacat caagtgtatc   5820
atatgccaag tacgccccct attgacgtca atgacggtaa atggcccgcc tggcattatg   5880
```

```
cccagtacat gaccttatgg gactttccta cttggcagta catctacgta ttagtcatcg   5940
ctattaccat ggtgatgcgg ttttggcagt acatcaatgg gcgtggatag cggtttgact   6000
cacggggatt tccaagtctc caccccattg acgtcaatgg gagtttgttt tggcaccaaa   6060
atcaacggga ctttccaaaa tgtcgtaaca actccgcccc attgacgcaa atgggcggta   6120
ggcgtgtacg gtgggaggtc tatataagca gagctcgttt agtgaaccgt cagatcgcct   6180
ggagacgcca tccacgctgt tttgacctcc atagaagaca ccgggaccga tccagcctcc   6240
gcggccggga acggtgcatt ggaagcttgg taccggtgaa ttcggcgcgc cagatctgcg   6300
gccgctagga agaaactcaa aacatcaaga ttttaaatac gcttcttggt ctccttgcta   6360
taattatctg ggataagcat gctgttttct gtctgtccct aacatgccct gtgattatcc   6420
gcaaacaaca cacccaaggg cagaactttg ttacttaaac accatcctgt ttgcttcttt   6480
cctcaggtca gcccaaggct gcccccctcgg tcactctgtt cccgccctcc tctgaggagc   6540
ttcaagccaa caaggccaca ctggtgtgtc tcataagtga cttctacccg ggagccgtga   6600
cagtggcctg gaaggcagat agcagccccg tcaaggcggg agtggagacc accacaccct   6660
ccaaacaaag caacaacaag tacgcggcca gcagctacct gagcctgacg cctgagcagt   6720
ggaagtccca cagaagctac agctgccagg tcacgcatga agggagcacc gtggagaaga   6780
cagtggcccc tacagaatgt tcatagagtt aacggatcga tccgagctcg gtaccaagct   6840
taagtttaaa ccgctgatca gcctcgactg tgccttctag ttgccagcca tctgttgttt   6900
gcccctcccc cgtgccttcc ttgaccctgg aaggtgccac tcccactgtc ctttcctaat   6960
aaaatgagga aattgcatcg cattgtctga gtaggtgtca ttctattctg gggggtgggg   7020
tggggcagga cagcaagggg gaggattggg aagacaatag caggcatgct ggggatgcgg   7080
tgggctctat ggcttctgag gcggaaagaa ccagctgcat taatgaatcg gccaacgcgc   7140
ggggagaggc ggtttgcgta ttgggcgctc ttccgcttcc tcgctcactg actcgctgcg   7200
ctcggtcgtt cggctgcggc gagcggtatc agctcactca aaggcggtaa tacggttatc   7260
cacagaatca ggggataacg caggaaagaa catgtgagca aaaggccagc aaaaggccag   7320
gaaccgtaaa aaggccgcgt tgctggcgtt tttccatagg ctccgccccc ctgacgagca   7380
tcacaaaaat cgacgctcaa gtcagaggtg gcgaaacccg acaggactat aaagatacca   7440
ggcgtttccc cctggaagct ccctcgtgcg ctctcctgtt ccgaccctgc cgcttaccgg   7500
atacctgtcc gcctttctcc cttcgggaag cgtggcgctt tctcatagct cacgctgtag   7560
gtatctcagt tcggtgtagg tcgttcgctc caagctgggc tgtgtgcacg aaccccccgt   7620
tcagcccgac cgctgcgcct tatccggtaa ctatcgtctt gagtccaacc cggtaagaca   7680
cgacttatcg ccactggcag cagccactgg taacaggatt agcagagcga ggtatgtagg   7740
cggtgctaca gagttcttga agtggtggcc taactacggc tacactagaa gaacagtatt   7800
tggtatctgc gctctgctga agccagttac cttcggaaaa agagttggta gctcttgatc   7860
cggcaaacaa accaccgctg gtagcggtgg tttttttgtt tgcaagcagc agattacgcg   7920
cagaaaaaaa ggatctcaag aagatccttt gatcttttct acggggtctg acgctcagtg   7980
gaacgaaaac tcacgttaag ggattttggt catgagatta tcaaaaagga tcttcaccta   8040
gatcctttta aattaaaaat gaagttttaa atcaatctaa agtatatatg agtaaacttg   8100
gtctgacagt taccaatgct taatcagtga ggcacctatc tcagcgatct gtctatttcg   8160
ttcatccata gttgcctgac tccccgtcgt gtagataact acgatacggg agggcttacc   8220
```

```
atctggcccc agtgctgcaa tgataccgcg agacccacgc tcaccggctc cagatttatc   8280

agcaataaac cagccagccg gaagggccga gcgcagaagt ggtcctgcaa ctttatccgc   8340

ctccatccag tctattaatt gttgccggga agctagagta agtagttcgc cagttaatag   8400

tttgcgcaac gttgttgcca ttgctacagg catcgtggtg tcacgctcgt cgtttggtat   8460

ggcttcattc agctccggtt cccaacgatc aaggcgagtt acatgatccc ccatgttgtg   8520

caaaaaagcg gttagctcct tcggtcctcc gatcgttgtc agaagtaagt tggccgcagt   8580

gttatcactc atggttatgg cagcactgca taattctctt actgtcatgc catccgtaag   8640

atgcttttct gtgactggtg agtactcaac caagtcattc tgagaatagt gtatgcggcg   8700

accgagttgc tcttgcccgg cgtcaatacg ggataatacc gcgccacata gcagaacttt   8760

aaaagtgctc atcattggaa aacgttcttc ggggcgaaaa ctctcaagga tcttaccgct   8820

gttgagatcc agttcgatgt aacccactcg tgcacccaac tgatcttcag catcttttac   8880

tttcaccagc gtttctgggt gagcaaaaac aggaaggcaa aatgccgcaa aaaagggaat   8940

aagggcgaca cggaaatgtt gaatactca                                     8969
```

<210> SEQ ID NO 129
<211> LENGTH: 57
<212> TYPE: PRT
<213> ORGANISM: Artificial Sequence
<220> FEATURE:
<223> OTHER INFORMATION: Sym-1705

<400> SEQUENCE: 129

```
Lys Gln Arg Gln Asn Lys Pro Pro Asn Lys Pro Asn Asn Asp Phe His
1               5                   10                  15

Phe Glu Val Phe Asn Phe Val Pro Cys Ser Ile Cys Ser Asn Asn Pro
            20                  25                  30

Thr Cys Trp Ala Ile Cys Lys Arg Ile Pro Asn Lys Lys Pro Gly Lys
        35                  40                  45

Lys Thr Thr Thr Lys Pro Thr Lys Lys
    50                  55
```

<210> SEQ ID NO 130
<211> LENGTH: 57
<212> TYPE: PRT
<213> ORGANISM: Artificial Sequence
<220> FEATURE:
<223> OTHER INFORMATION: Sym-1788

<400> SEQUENCE: 130

```
Lys Pro Arg Pro Lys Ser Pro Pro Lys Lys Pro Lys Asp Asp Tyr His
1               5                   10                  15

Phe Glu Val Phe Asn Phe Val Pro Cys Ser Ile Cys Gly Asn Asn Gln
            20                  25                  30

Leu Cys Lys Ser Ile Cys Lys Thr Ile Pro Ser Asn Lys Pro Lys Lys
        35                  40                  45

Lys Pro Thr Ile Lys Pro Thr Asn Lys
    50                  55
```

<210> SEQ ID NO 131
<211> LENGTH: 40
<212> TYPE: PRT
<213> ORGANISM: Artificial Sequence
<220> FEATURE:
<223> OTHER INFORMATION: Sym-1789

<400> SEQUENCE: 131

```
Lys Pro Arg Pro Lys Ser Pro Pro Lys Lys Pro Lys Asp Asp Tyr His
1               5                   10                  15

Phe Glu Val Phe Asn Phe Val Pro Cys Ser Ile Cys Gly Asn Asn Gln
            20                  25                  30

Leu Cys Lys Ser Ile Cys Lys Thr
        35                  40


<210> SEQ ID NO 132
<211> LENGTH: 14
<212> TYPE: PRT
<213> ORGANISM: Artificial Sequence
<220> FEATURE:
<223> OTHER INFORMATION: PEPTIDE sequence

<400> SEQUENCE: 132

Phe His Phe Glu Val Phe Asn Phe Val Pro Cys Ser Ile Cys
1               5                   10


<210> SEQ ID NO 133
<211> LENGTH: 6
<212> TYPE: PRT
<213> ORGANISM: Artificial Sequence
<220> FEATURE:
<223> OTHER INFORMATION: Synthesized sequence
<220> FEATURE:
<221> NAME/KEY: MISC_FEATURE
<222> LOCATION: (2)..(5)
<223> OTHER INFORMATION: Xaa is any amino acid

<400> SEQUENCE: 133

Cys Xaa Xaa Xaa Xaa Cys
1               5


<210> SEQ ID NO 134
<211> LENGTH: 63
<212> TYPE: DNA
<213> ORGANISM: Artificial Sequence
<220> FEATURE:
<223> OTHER INFORMATION: HAVT20 leader synthesized sequence

<400> SEQUENCE: 134

atggcctgcc ctggctttct ctgggcactt gtgatctcca cctgtcttga attttccatg     60

gct                                                                    63


<210> SEQ ID NO 135
<211> LENGTH: 21
<212> TYPE: PRT
<213> ORGANISM: Artificial Sequence
<220> FEATURE:
<223> OTHER INFORMATION: HAVT20 leader synthesized sequence

<400> SEQUENCE: 135

Met Ala Cys Pro Gly Phe Leu Trp Ala Leu Val Ile Ser Thr Cys Leu
1               5                   10                  15

Glu Phe Ser Met Ala
            20


<210> SEQ ID NO 136
<211> LENGTH: 31
<212> TYPE: PRT
<213> ORGANISM: respiratory syncytial virus
<220> FEATURE:
<221> NAME/KEY: MISC_FEATURE
<222> LOCATION: (13)..(13)
<223> OTHER INFORMATION: Xaa can be S (Ser) or N (Asn)
```

```
<220> FEATURE:
<221> NAME/KEY: MISC_FEATURE
<222> LOCATION: (19)..(19)
<223> OTHER INFORMATION: Xaa can be W (Trp) or R (Arg)
<220> FEATURE:
<221> NAME/KEY: MISC_FEATURE
<222> LOCATION: (20)..(20)
<223> OTHER INFORMATION: Xaa can be A (Ala), D (Asp), or T (Thr)
<220> FEATURE:
<221> NAME/KEY: MISC_FEATURE
<222> LOCATION: (24)..(24)
<223> OTHER INFORMATION: Xaa can be R (Arg) or K (Lys)
<220> FEATURE:
<221> NAME/KEY: MISC_FEATURE
<222> LOCATION: (25)..(25)
<223> OTHER INFORMATION: Xaa can be I (Ile) or M (Met)
<220> FEATURE:
<221> NAME/KEY: MISC_FEATURE
<222> LOCATION: (26)..(26)
<223> OTHER INFORMATION: Xaa can be P (Pro) or S (Ser)
<220> FEATURE:
<221> NAME/KEY: MISC_FEATURE
<222> LOCATION: (27)..(27)
<223> OTHER INFORMATION: Xaa can be K (Lys), N (Asn) or S (Ser)
<220> FEATURE:
<221> NAME/KEY: MISC_FEATURE
<222> LOCATION: (29)..(29)
<223> OTHER INFORMATION: Xaa can be P (Pro), L (Leu), or T (Thr)
<220> FEATURE:
<221> NAME/KEY: MISC_FEATURE
<222> LOCATION: (30)..(30)
<223> OTHER INFORMATION: Xaa can be G (Gly), A (Ala), E (Glu), R (Arg),
      or V (Val)
<220> FEATURE:
<221> NAME/KEY: MISC_FEATURE
<222> LOCATION: (31)..(31)
<223> OTHER INFORMATION: Xaa can be K (Lys) or R (Arg)

<400> SEQUENCE: 136

Phe Glu Val Phe Asn Phe Val Pro Cys Ser Ile Cys Xaa Asn Asn Pro
1               5                   10                  15

Thr Cys Xaa Xaa Ile Cys Lys Xaa Xaa Xaa Xaa Lys Xaa Xaa Xaa
            20                  25                  30


<210> SEQ ID NO 137
<211> LENGTH: 32
<212> TYPE: PRT
<213> ORGANISM: respiratory syncytial virus
<220> FEATURE:
<221> NAME/KEY: MISC_FEATURE
<222> LOCATION: (10)..(10)
<223> OTHER INFORMATION: Xaa can be S (Ser), C (Cys), or G (Gly)
<220> FEATURE:
<221> NAME/KEY: MISC_FEATURE
<222> LOCATION: (11)..(11)
<223> OTHER INFORMATION: Xaa can be I (Ile), T (Thr), or V (Val)
<220> FEATURE:
<221> NAME/KEY: MISC_FEATURE
<222> LOCATION: (16)..(16)
<223> OTHER INFORMATION: Xaa can be Q (Gln), K (Lys), or R (Arg)
<220> FEATURE:
<221> NAME/KEY: MISC_FEATURE
<222> LOCATION: (19)..(19)
<223> OTHER INFORMATION: Xaa can be K (Lys), or R (Arg)
<220> FEATURE:
<221> NAME/KEY: MISC_FEATURE
<222> LOCATION: (21)..(21)
<223> OTHER INFORMATION: Xaa can be I (Ile) or F (Phe)
<220> FEATURE:
<221> NAME/KEY: MISC_FEATURE
<222> LOCATION: (24)..(24)
<223> OTHER INFORMATION: Xaa can be T (Thr), A (Ala), K (Lys), I (Ile)
<220> FEATURE:
<221> NAME/KEY: MISC_FEATURE
<222> LOCATION: (27)..(27)
<223> OTHER INFORMATION: Xaa can be S (Ser) or N (Asn)
```

<220> FEATURE:
<221> NAME/KEY: MISC_FEATURE
<222> LOCATION: (30)..(30)
<223> OTHER INFORMATION: Xaa can be P (Pro) or L (Leu)

<400> SEQUENCE: 137

```
Phe Glu Val Phe Asn Phe Val Pro Cys Xaa Xaa Cys Gly Asn Asn Xaa
1               5                   10                  15

Leu Cys Xaa Ser Xaa Cys Lys Xaa Ile Pro Xaa Asn Lys Xaa Lys Lys
            20                  25                  30
```

<210> SEQ ID NO 138
<211> LENGTH: 21
<212> TYPE: PRT
<213> ORGANISM: respiratory syncytial virus

<400> SEQUENCE: 138

```
Phe His Phe Glu Val Phe Asn Phe Val Pro Cys Ser Cys Asn Cys Ala
1               5                   10                  15

Ile Cys Lys Ile Pro
            20
```

<210> SEQ ID NO 139
<211> LENGTH: 16
<212> TYPE: PRT
<213> ORGANISM: respiratory syncytial virus

<400> SEQUENCE: 139

```
Tyr His Phe Glu Val Phe Asn Phe Val Pro Cys Ser Cys Cys Ile Cys
1               5                   10                  15
```

<210> SEQ ID NO 140
<211> LENGTH: 21
<212> TYPE: PRT
<213> ORGANISM: respiratory syncytial virus

<400> SEQUENCE: 140

```
Phe His Phe Glu Val Phe Asn Phe Val Pro Cys Cys Asn Asn Cys Ala
1               5                   10                  15

Ile Cys Lys Asn Pro
            20
```

<210> SEQ ID NO 141
<211> LENGTH: 18
<212> TYPE: PRT
<213> ORGANISM: respiratory syncytial virus

<400> SEQUENCE: 141

```
Tyr His Phe Glu Val Phe Asn Phe Val Pro Cys Ser Cys Asn Cys Ile
1               5                   10                  15

Cys Lys
```

<210> SEQ ID NO 142
<211> LENGTH: 15
<212> TYPE: PRT
<213> ORGANISM: respiratory syncytial virus

<400> SEQUENCE: 142

```
Phe His Phe Glu Val Phe Asn Phe Val Pro Cys Ser Ile Cys Gly
1               5                   10                  15
```

<210> SEQ ID NO 143
<211> LENGTH: 15

<212> TYPE: PRT
<213> ORGANISM: respiratory syncytial virus

<400> SEQUENCE: 143

Tyr His Phe Glu Val Phe Asn Phe Val Pro Cys Ser Ile Gln Cys
1 5 10 15

<210> SEQ ID NO 144
<211> LENGTH: 15
<212> TYPE: PRT
<213> ORGANISM: respiratory syncytial virus

<400> SEQUENCE: 144

Phe Glu Val Phe Asn Phe Val Pro Cys Ser Ile Cys Cys Ala Ile
1 5 10 15

<210> SEQ ID NO 145
<211> LENGTH: 13
<212> TYPE: PRT
<213> ORGANISM: respiratory syncytial virus

<400> SEQUENCE: 145

Phe Glu Val Phe Asn Phe Val Pro Cys Ser Ile Cys Cys
1 5 10

<210> SEQ ID NO 146
<211> LENGTH: 12
<212> TYPE: PRT
<213> ORGANISM: respiratory syncytial virus

<400> SEQUENCE: 146

Phe Glu Val Phe Asn Phe Val Pro Cys Cys Cys Cys
1 5 10

<210> SEQ ID NO 147
<211> LENGTH: 10
<212> TYPE: PRT
<213> ORGANISM: respiratory syncytial virus

<400> SEQUENCE: 147

Phe Glu Val Phe Asn Phe Val Pro Cys Cys
1 5 10

<210> SEQ ID NO 148
<211> LENGTH: 10
<212> TYPE: PRT
<213> ORGANISM: respiratory syncytial virus

<400> SEQUENCE: 148

Phe His Phe Glu Val Phe Asn Phe Val Pro
1 5 10

<210> SEQ ID NO 149
<211> LENGTH: 20
<212> TYPE: PRT
<213> ORGANISM: respiratory syncytial virus

<400> SEQUENCE: 149

Tyr His Phe Glu Val Phe Asn Phe Val Pro Ser Ile Gly Asn Gln Leu
1 5 10 15

Cys Ile Cys Thr
20

<210> SEQ ID NO 150

-continued

```
<211> LENGTH: 9
<212> TYPE: PRT
<213> ORGANISM: respiratory syncytial virus

<400> SEQUENCE: 150

His Phe Glu Val Phe Asn Phe Val Pro
1               5


<210> SEQ ID NO 151
<211> LENGTH: 25
<212> TYPE: PRT
<213> ORGANISM: respiratory syncytial virus

<400> SEQUENCE: 151

His Phe Glu Val Phe Asn Phe Val Pro Cys Ser Ile Cys Gly Asn Asn
1               5                   10                  15

Gln Leu Cys Lys Ile Cys Thr Ile Pro
            20                  25
```